(12) United States Patent
Denzer et al.

(10) Patent No.: US 10,918,805 B2
(45) Date of Patent: *Feb. 16, 2021

(54) AUTOINJECTOR APPARATUS

(71) Applicant: AMGEN INC., Thousand Oaks, CA (US)

(72) Inventors: Michael Denzer, Ringoes, NJ (US);
Robert W. Swift, Fillmore, CA (US);
Neal Johnston, Dallas, TX (US);
Gabriele Ganzitti, Milan (IT);
Kenneth R. Ewing, Fremont, CA (US);
Suhas Krishna, Simi Valley, CA (US)

(73) Assignee: AMGEN INC., Thousand Oaks, CA (US)

( * ) Notice: Subject to any disclaimer, the term of this patent is extended or adjusted under 35 U.S.C. 154(b) by 197 days.

This patent is subject to a terminal disclaimer.

(21) Appl. No.: 16/026,294

(22) Filed: Jul. 3, 2018

(65) Prior Publication Data

US 2019/0201632 A1    Jul. 4, 2019

Related U.S. Application Data

(63) Continuation of application No. 14/112,479, filed as application No. PCT/US2012/034535 on Apr. 20, 2012, now Pat. No. 10,092,706.

(Continued)

(51) Int. Cl.
*A61M 5/32* (2006.01)
*A61M 5/20* (2006.01)
(Continued)

(52) U.S. Cl.
CPC ............ *A61M 5/3204* (2013.01); *A61J 1/065* (2013.01); *A61M 5/20* (2013.01); *A61M 5/50* (2013.01);
(Continued)

(58) Field of Classification Search
CPC .... A61M 5/50; A61M 5/20; A61M 2205/121; A61M 2205/123; A61M 5/3271;
(Continued)

(56) References Cited

U.S. PATENT DOCUMENTS 2,525,398 A   10/1950  Collins
2,565,081 A    8/1951  Maynes
(Continued)

FOREIGN PATENT DOCUMENTS

AU    2009249027 B2    8/2014
CA       2074565 A1    1/1993
(Continued)

OTHER PUBLICATIONS

Australian Patent Application No. 2019202863, Examination Report No. 1, dated Sep. 13, 2019.
(Continued)

*Primary Examiner* — Bradley J Osinski
(74) *Attorney, Agent, or Firm* — Marshall, Gerstein & Borun LLP

(57) ABSTRACT

An autoinjector apparatus is disclosed which comprises a single-use cassette and an autoinjector. The cassette comprises a housing and a sleeve movably disposed in the housing. A syringe may be disposed in the sleeve and secured therein with a lock cap. The lock cap is affixed to a distal end of the sleeve and contacts the distal end of the syringe. A shield remover extends through an opening in a proximal end of the housing for removing a needle shield which covers a needle of the syringe. A cassette identification arrangement is provided on a surface of the housing to enable the autoinjector to identify the cassette. The autoinjector is provided with a detector for reading the cassette identification arrangement.

20 Claims, 21 Drawing Sheets

Related U.S. Application Data

(60) Provisional application No. 61/477,553, filed on Apr. 20, 2011.

(51) Int. Cl.
*A61J 1/06* (2006.01)
*A61M 5/50* (2006.01)
*A61M 5/24* (2006.01)

(52) U.S. Cl.
CPC ........... *A61M 5/326* (2013.01); *A61M 5/3271* (2013.01); *A61M 2005/206* (2013.01); *A61M 2005/208* (2013.01); *A61M 2005/2407* (2013.01); *A61M 2005/2496* (2013.01); *A61M 2005/3247* (2013.01); *A61M 2205/0216* (2013.01); *A61M 2205/121* (2013.01); *A61M 2205/123* (2013.01); *A61M 2205/14* (2013.01); *A61M 2205/502* (2013.01); *A61M 2205/581* (2013.01); *A61M 2205/583* (2013.01); *A61M 2205/586* (2013.01); *A61M 2205/6018* (2013.01); *A61M 2205/6036* (2013.01); *A61M 2205/6045* (2013.01); *A61M 2205/8206* (2013.01)

(58) Field of Classification Search
CPC .. A61M 2005/3247; A61M 2205/6045; A61M 5/3204
See application file for complete search history.

(56) References Cited

U.S. PATENT DOCUMENTS

| | | |
|---|---|---|
| 2,701,566 A | 2/1955 | Krug |
| 2,702,547 A | 2/1955 | Glass |
| 3,051,173 A | 8/1962 | Johnson et al. |
| 3,064,650 A | 11/1962 | Lewis |
| 3,203,269 A | 8/1965 | Perrine |
| 3,212,685 A | 10/1965 | James et al. |
| 3,623,474 A | 11/1971 | Heilman et al. |
| 3,720,211 A | 3/1973 | Kyrias |
| 3,859,996 A | 1/1975 | Mizzy et al. |
| 3,964,481 A | 6/1976 | Gourlandt et al. |
| 4,108,177 A | 8/1978 | Pistor |
| 4,231,368 A | 11/1980 | Becker |
| 4,273,122 A | 6/1981 | Whitney et al. |
| 4,276,879 A | 7/1981 | Yiournas |
| 4,373,526 A | 2/1983 | Kling |
| 4,421,107 A | 12/1983 | Estes et al. |
| 4,465,478 A | 8/1984 | Sabelman et al. |
| 4,502,488 A | 3/1985 | Degironimo et al. |
| 4,504,263 A | 3/1985 | Steuer et al. |
| 4,515,590 A | 5/1985 | Daniel |
| 4,573,975 A | 3/1986 | Frist et al. |
| 4,585,439 A | 4/1986 | Michel |
| 4,613,328 A | 9/1986 | Boyd |
| 4,617,016 A | 10/1986 | Blomberg |
| 4,636,201 A | 1/1987 | Ambrose et al. |
| 4,685,903 A | 8/1987 | Cable et al. |
| 4,758,227 A | 7/1988 | Lancaster, Jr. et al. |
| 4,787,893 A | 11/1988 | Villette |
| 4,790,823 A | 12/1988 | Charton et al. |
| 4,838,857 A | 6/1989 | Strowe et al. |
| 4,877,034 A | 10/1989 | Atkins et al. |
| 4,902,279 A | 2/1990 | Schmidtz et al. |
| 4,919,596 A | 4/1990 | Slate et al. |
| 4,986,818 A | 1/1991 | Imbert et al. |
| 5,013,299 A | 5/1991 | Clark |
| 5,024,616 A | 6/1991 | Ogle, II |
| 5,034,003 A | 7/1991 | Denance |
| 5,080,104 A | 1/1992 | Marks et al. |
| 5,085,641 A | 2/1992 | Sarnoff et al. |
| 5,092,843 A | 3/1992 | Monroe et al. |
| 5,098,400 A | 3/1992 | Crouse et al. |
| 5,112,317 A | 5/1992 | Michel |
| 5,114,404 A | 5/1992 | Paxton et al. |
| 5,114,406 A | 5/1992 | Gabriel et al. |
| 5,176,643 A | 1/1993 | Kramer et al. |
| 5,180,371 A | 1/1993 | Spinello |
| 5,200,604 A | 4/1993 | Rudko et al. |
| 5,221,268 A | 6/1993 | Barton et al. |
| 5,271,413 A | 12/1993 | Dalamagas et al. |
| 5,300,029 A | 4/1994 | Denance |
| 5,318,522 A | 6/1994 | D'Antonio |
| 5,352,196 A | 10/1994 | Haber et al. |
| 5,354,286 A | 10/1994 | Mesa et al. |
| 5,354,287 A | 10/1994 | Wacks |
| 5,382,785 A | 1/1995 | Rink |
| 5,393,497 A | 2/1995 | Haber et al. |
| 5,425,715 A | 6/1995 | Dalling et al. |
| 5,431,627 A | 7/1995 | Pastrone et al. |
| 5,451,210 A | 9/1995 | Kramer et al. |
| 5,456,670 A | 10/1995 | Neer et al. |
| 5,458,263 A | 10/1995 | Ciammitti et al. |
| 5,478,316 A | 12/1995 | Bitdinger et al. |
| 5,540,664 A | 7/1996 | Wyrick |
| 5,569,190 A | 10/1996 | D'Antonio |
| 5,569,197 A | 10/1996 | Helmus et al. |
| 5,569,212 A | 10/1996 | Brown |
| 5,578,014 A | 11/1996 | Erez et al. |
| 5,584,815 A | 12/1996 | Pawelka et al. |
| 5,593,390 A | 1/1997 | Castellano et al. |
| 5,599,302 A | 2/1997 | Lilley et al. |
| 5,616,132 A | 4/1997 | Newman |
| 5,647,851 A | 7/1997 | Pokras |
| 5,647,853 A | 7/1997 | Feldmann et al. |
| 5,665,071 A | 9/1997 | Wyrick |
| 5,681,291 A | 10/1997 | Galli |
| 5,690,618 A | 11/1997 | Smith et al. |
| 5,695,472 A | 12/1997 | Wyrick |
| 5,698,189 A | 12/1997 | Rowe et al. |
| 5,709,662 A | 1/1998 | Olive et al. |
| 5,720,729 A | 2/1998 | Kriesel |
| 5,728,074 A | 3/1998 | Castellano et al. |
| 5,746,714 A | 5/1998 | Salo et al. |
| 5,779,683 A | 7/1998 | Meyer |
| 5,807,346 A | 9/1998 | Frezza |
| 5,843,036 A | 12/1998 | Olive et al. |
| 5,868,711 A | 2/1999 | Kramer et al. |
| 5,911,703 A | 6/1999 | Slate et al. |
| 5,919,159 A | 7/1999 | Lilley et al. |
| 5,921,963 A | 7/1999 | Erez et al. |
| 5,921,966 A | 7/1999 | Bendek et al. |
| 5,928,158 A | 7/1999 | Aristides |
| 5,945,046 A | 8/1999 | Hehl et al. |
| 5,957,897 A | 9/1999 | Jeffrey |
| 5,968,063 A | 10/1999 | Chu et al. |
| 5,993,423 A | 11/1999 | Choi |
| 6,019,745 A | 2/2000 | Gray |
| 6,019,747 A | 2/2000 | McPhee |
| 6,051,896 A | 4/2000 | Shibuya et al. |
| 6,090,082 A | 7/2000 | King et al. |
| 6,099,503 A | 8/2000 | Stradella |
| 6,104,941 A | 8/2000 | Huey et al. |
| 6,149,626 A | 11/2000 | Bachynsky et al. |
| 6,159,184 A | 12/2000 | Perez et al. |
| 6,171,276 B1 | 1/2001 | Lippe et al. |
| 6,171,283 B1 | 1/2001 | Perez et al. |
| 6,183,442 B1 | 2/2001 | Athanasiou et al. |
| 6,190,361 B1 | 2/2001 | Gettig et al. |
| 6,203,530 B1 | 3/2001 | Stewart, Sr. |
| 6,210,369 B1 | 4/2001 | Wilmot et al. |
| 6,213,987 B1 | 4/2001 | Hirsch et al. |
| 6,241,709 B1 | 6/2001 | Bechtold et al. |
| 6,245,043 B1 | 6/2001 | Villette |
| 6,248,093 B1 | 6/2001 | Moberg |
| 6,270,479 B1 | 8/2001 | Bergens et al. |
| 6,270,481 B1 | 8/2001 | Mason et al. |
| 6,280,421 B1 | 8/2001 | Kirchhofer et al. |
| 6,290,683 B1 | 9/2001 | Erez et al. |
| 6,344,030 B1 | 2/2002 | Duchon et al. |
| 6,344,032 B1 | 2/2002 | Perez et al. |
| 6,371,939 B2 | 4/2002 | Bergens et al. |
| 6,387,078 B1 | 5/2002 | Gillespie, III |

(56) References Cited

U.S. PATENT DOCUMENTS

| | | |
|---|---|---|
| 6,406,456 B1 | 6/2002 | Slate et al. |
| 6,447,482 B1 | 9/2002 | Ronborg et al. |
| 6,454,743 B1 | 9/2002 | Weber |
| 6,503,454 B1 | 1/2003 | Hadimioglu et al. |
| 6,520,928 B1 | 2/2003 | Junior |
| 6,540,672 B1 | 4/2003 | Simonsen et al. |
| 6,544,234 B1 | 4/2003 | Gabriel |
| 6,547,755 B1 | 4/2003 | Lippe et al. |
| 6,562,006 B1 | 5/2003 | Hjertman et al. |
| 6,569,123 B2 | 5/2003 | Alchas et al. |
| 6,569,127 B1 | 5/2003 | Fago et al. |
| 6,599,272 B1 | 7/2003 | Hjertman et al. |
| 6,641,561 B1 | 11/2003 | Hill et al. |
| 6,645,169 B1 | 11/2003 | Slate et al. |
| 6,645,177 B1 | 11/2003 | Shearn |
| 6,648,858 B2 | 11/2003 | Asbaghi |
| 6,652,483 B2 | 11/2003 | Slate et al. |
| D483,116 S | 12/2003 | Castellano |
| 6,656,163 B1 | 12/2003 | Marshall et al. |
| 6,656,164 B1 | 12/2003 | Smith |
| 6,669,664 B2 | 12/2003 | Slate et al. |
| 6,692,469 B1 | 2/2004 | Weekes et al. |
| 6,743,202 B2 | 6/2004 | Hirschman et al. |
| 6,746,427 B2 | 6/2004 | Duchon et al. |
| 6,752,787 B1 | 6/2004 | Causey, III et al. |
| 6,767,336 B1 | 7/2004 | Kaplan |
| 6,770,052 B2 | 8/2004 | Hill et al. |
| 6,796,957 B2 | 9/2004 | Carpenter et al. |
| 6,805,686 B1 | 10/2004 | Fathallah et al. |
| 6,808,507 B2 | 10/2004 | Roser |
| 6,817,986 B2 | 11/2004 | Slate et al. |
| 6,835,193 B2 | 12/2004 | Epstein et al. |
| 6,854,620 B2 | 2/2005 | Ramey |
| 6,890,319 B1 | 5/2005 | Crocker |
| 6,932,793 B1 | 8/2005 | Marshall et al. |
| 6,979,316 B1 | 12/2005 | Rubin et al. |
| 6,986,760 B2 | 1/2006 | Giambattista et al. |
| 7,008,399 B2 | 3/2006 | Larsen et al. |
| 7,011,649 B2 | 3/2006 | De La Serna et al. |
| 7,025,774 B2 | 4/2006 | Freeman et al. |
| 7,041,085 B2 | 5/2006 | Perez et al. |
| 7,066,909 B1 | 6/2006 | Peter et al. |
| 7,094,230 B2 | 8/2006 | Flaherty et al. |
| 7,104,400 B2 | 9/2006 | Kiehne |
| 7,118,553 B2 | 10/2006 | Scherer |
| 7,226,450 B2 | 6/2007 | Athanasiou et al. |
| 7,255,684 B2 | 8/2007 | Zubry |
| 7,273,469 B1 | 9/2007 | Chan et al. |
| 7,290,573 B2 | 11/2007 | Py et al. |
| 7,291,132 B2 | 11/2007 | Deruntz et al. |
| 7,297,135 B2 | 11/2007 | Jeffrey |
| 7,297,136 B2 | 11/2007 | Wyrick |
| 7,357,790 B2 | 4/2008 | Hommann et al. |
| 7,361,160 B2 | 4/2008 | Hommann et al. |
| 7,370,759 B2 | 5/2008 | Hommann |
| 7,381,201 B2 | 6/2008 | Gilbert et al. |
| 7,390,319 B2 | 6/2008 | Friedman |
| 7,442,185 B2 | 10/2008 | Amark et al. |
| 7,449,012 B2 | 11/2008 | Young et al. |
| 7,476,217 B2 | 1/2009 | Martin et al. |
| 7,500,963 B2 | 3/2009 | Westbye et al. |
| 7,500,966 B2 | 3/2009 | Hommann |
| 7,553,294 B2 | 6/2009 | Lazzaro et al. |
| 7,597,685 B2 | 10/2009 | Olson |
| 7,635,348 B2 | 12/2009 | Raven et al. |
| 7,635,350 B2 | 12/2009 | Scherer |
| 7,648,483 B2 | 1/2010 | Edwards et al. |
| 7,654,987 B2 | 2/2010 | Hommann et al. |
| 7,670,314 B2 | 3/2010 | Wall et al. |
| 7,686,789 B2 | 3/2010 | Nemoto et al. |
| 7,731,686 B2 | 6/2010 | Edwards et al. |
| D619,706 S | 7/2010 | Schon et al. |
| 7,749,195 B2 | 7/2010 | Hommann |
| 7,760,099 B2 | 7/2010 | Knight |
| 7,785,292 B2 | 8/2010 | Harrison |
| D625,015 S | 10/2010 | Hansen et al. |
| 7,828,776 B2 | 11/2010 | Nemoto et al. |
| D628,690 S | 12/2010 | Galbraith |
| 7,857,791 B2 | 12/2010 | Jacobs et al. |
| 7,887,513 B2 | 2/2011 | Nemoto et al. |
| 7,901,377 B1 | 3/2011 | Harrison et al. |
| 7,909,796 B2 | 3/2011 | Weber |
| 7,918,823 B2 | 4/2011 | Edwards et al. |
| 7,922,695 B2 | 4/2011 | Wiegel et al. |
| D637,713 S | 5/2011 | Nord et al. |
| 7,938,803 B2 | 5/2011 | Mernoe et al. |
| D642,261 S | 7/2011 | York et al. |
| 7,976,499 B2 | 7/2011 | Grunhut et al. |
| 8,012,120 B2 | 9/2011 | Slate et al. |
| 8,012,125 B1 | 9/2011 | Fago et al. |
| 8,016,797 B2 | 9/2011 | Gratwohl et al. |
| 8,043,262 B2 | 10/2011 | Streit et al. |
| 8,048,037 B2 | 11/2011 | Kohlbrenner et al. |
| 8,052,645 B2 | 11/2011 | Slate et al. |
| D650,070 S | 12/2011 | Mori |
| 8,088,096 B2 | 1/2012 | Lauchard et al. |
| 8,105,271 B2 | 1/2012 | Matusch |
| 8,141,417 B2 | 3/2012 | Gibson et al. |
| 8,152,779 B2 | 4/2012 | Cabiri |
| 8,177,749 B2 | 5/2012 | Slate et al. |
| 8,221,356 B2 | 7/2012 | Enggaard et al. |
| 8,226,610 B2 | 7/2012 | Edwards et al. |
| 8,277,414 B2 | 10/2012 | Barrow-Williams et al. |
| 8,298,171 B2 | 10/2012 | Ishikawa et al. |
| 8,308,687 B2 | 11/2012 | Carrel et al. |
| 8,337,472 B2 | 12/2012 | Edginton et al. |
| D673,677 S | 1/2013 | Noda et al. |
| 8,343,103 B2 | 1/2013 | Moser |
| 8,376,985 B2 | 2/2013 | Pongpairochana et al. |
| D679,008 S | 3/2013 | Schroeder et al. |
| D679,391 S | 4/2013 | Chinowsky et al. |
| 8,491,538 B2 | 7/2013 | Kohlbrenner et al. |
| 8,523,803 B1 | 9/2013 | Favreau |
| 8,591,465 B2 | 11/2013 | Hommann |
| D694,879 S | 12/2013 | Julian et al. |
| 8,603,026 B2 | 12/2013 | Favreau |
| 8,603,027 B2 | 12/2013 | Favreau |
| 8,609,621 B2 | 12/2013 | Bedzyk et al. |
| 8,628,723 B2 | 1/2014 | Vandergaw |
| D702,343 S | 4/2014 | Dale et al. |
| D702,835 S | 4/2014 | Vinchon |
| 8,690,827 B2 | 4/2014 | Edwards et al. |
| 8,696,628 B2 | 4/2014 | Grunhut |
| 8,716,711 B2 | 5/2014 | Iwasaki |
| D718,439 S | 11/2014 | Woehr et al. |
| 8,900,204 B2 | 12/2014 | Geertsen |
| 8,911,410 B2 | 12/2014 | Ekman et al. |
| 8,960,827 B2 | 2/2015 | McMillin et al. |
| 8,961,473 B2 | 2/2015 | Heald |
| 8,968,255 B2 | 3/2015 | Oakland |
| 9,011,386 B2 | 4/2015 | Kronestedt et al. |
| 9,138,542 B2 | 9/2015 | Smith |
| D748,783 S | 2/2016 | Zhang et al. |
| 9,278,177 B2 | 3/2016 | Edwards et al. |
| D757,254 S | 5/2016 | Wohlfahrt et al. |
| D765,241 S | 8/2016 | Holland |
| D768,851 S | 10/2016 | Rozwadowski et al. |
| D768,852 S | 10/2016 | Rozwadowski et al. |
| 9,616,173 B2 | 4/2017 | Slate et al. |
| 9,649,443 B2 | 5/2017 | Klintenstedt et al. |
| 9,925,336 B2 | 3/2018 | Slate et al. |
| 9,974,904 B2 | 5/2018 | Burk et al. |
| 10,092,703 B2 | 10/2018 | Mounce et al. |
| 10,092,706 B2 | 10/2018 | Denzer et al. |
| 2001/0005781 A1 | 6/2001 | Bergens et al. |
| 2001/0018937 A1 | 9/2001 | Nemoto |
| 2001/0034502 A1 | 10/2001 | Moberg et al. |
| 2001/0047153 A1 | 11/2001 | Trocki et al. |
| 2002/0016569 A1 | 2/2002 | Critchlow et al. |
| 2002/0022066 A1 | 2/2002 | Matsubayashi et al. |
| 2002/0029018 A1 | 3/2002 | Jeffrey |
| 2002/0095120 A1 | 7/2002 | Larsen et al. |
| 2002/0099334 A1 | 7/2002 | Hanson et al. |
| 2002/0133113 A1 | 9/2002 | Madsen et al. |

(56) References Cited

U.S. PATENT DOCUMENTS

| | | |
|---|---|---|
| 2002/0151855 A1 | 10/2002 | Douglas et al. |
| 2002/0156426 A1 | 10/2002 | Gagnieux et al. |
| 2003/0036725 A1 | 2/2003 | Lavi et al. |
| 2003/0050592 A1 | 3/2003 | Slate et al. |
| 2003/0065536 A1 | 4/2003 | Hansen et al. |
| 2003/0105430 A1 | 6/2003 | Lavi et al. |
| 2003/0236502 A1 | 12/2003 | De La Serna et al. |
| 2004/0019326 A1 | 1/2004 | Gilbert et al. |
| 2004/0039336 A1 | 2/2004 | Amark et al. |
| 2004/0054327 A1 | 3/2004 | Gillespie |
| 2004/0068266 A1 | 4/2004 | Delmotte |
| 2004/0116861 A1 | 6/2004 | Trocki et al. |
| 2004/0129803 A1 | 7/2004 | Dolder et al. |
| 2004/0133154 A1 | 7/2004 | Flaherty et al. |
| 2004/0133162 A1 | 7/2004 | Trocki et al. |
| 2004/0153008 A1 | 8/2004 | Sharf et al. |
| 2004/0208845 A1 | 10/2004 | Michal et al. |
| 2004/0225262 A1 | 11/2004 | Fathallah et al. |
| 2004/0258756 A1 | 12/2004 | McLoughlin |
| 2005/0020979 A1 | 1/2005 | Westbye et al. |
| 2005/0027255 A1 | 2/2005 | Lavi et al. |
| 2005/0033242 A1 | 2/2005 | Perez et al. |
| 2005/0049561 A1 | 3/2005 | Hommann et al. |
| 2005/0054987 A1 | 3/2005 | Perez et al. |
| 2005/0080377 A1 | 4/2005 | Sadowski et al. |
| 2005/0148869 A1 | 7/2005 | Masuda |
| 2005/0165404 A1 | 7/2005 | Miller |
| 2005/0171476 A1 | 8/2005 | Judson et al. |
| 2005/0171477 A1 | 8/2005 | Rubin et al. |
| 2005/0197650 A1 | 9/2005 | Sugimoto et al. |
| 2005/0203466 A1 | 9/2005 | Hommann et al. |
| 2005/0209569 A1 | 9/2005 | Ishikawa et al. |
| 2005/0261693 A1 | 11/2005 | Miller et al. |
| 2005/0277885 A1 | 12/2005 | Scherer |
| 2006/0022363 A1 | 2/2006 | Konno et al. |
| 2006/0030819 A1 | 2/2006 | Young et al. |
| 2006/0157064 A1 | 7/2006 | Davison et al. |
| 2006/0173408 A1 | 8/2006 | Wyrick |
| 2006/0251646 A1 | 11/2006 | Utku |
| 2006/0270985 A1 | 11/2006 | Hommann et al. |
| 2007/0021720 A1 | 1/2007 | Guillermo |
| 2007/0025879 A1 | 2/2007 | Vandergaw |
| 2007/0027430 A1 | 2/2007 | Hommann |
| 2007/0066938 A1 | 3/2007 | Lio et al. |
| 2007/0100281 A1 | 5/2007 | Morris et al. |
| 2007/0112301 A1 | 5/2007 | Preuthun et al. |
| 2007/0112310 A1 | 5/2007 | Lavi et al. |
| 2007/0118081 A1 | 5/2007 | Daily et al. |
| 2007/0135767 A1 | 6/2007 | Gillespie et al. |
| 2007/0142787 A1 | 6/2007 | Scherer |
| 2007/0149925 A1 | 6/2007 | Edwards et al. |
| 2007/0167920 A1 | 7/2007 | Hommann |
| 2007/0173770 A1 | 7/2007 | Stamp |
| 2007/0197954 A1 | 8/2007 | Keenan |
| 2007/0197968 A1 | 8/2007 | Pongpairochana et al. |
| 2007/0219498 A1 | 9/2007 | Malone et al. |
| 2007/0233001 A1 | 10/2007 | Burroughs et al. |
| 2007/0239114 A1 | 10/2007 | Edwards et al. |
| 2007/0250010 A1 | 10/2007 | Hohlfelder et al. |
| 2007/0265568 A1 | 11/2007 | Tsals et al. |
| 2008/0015510 A1 | 1/2008 | Sandoz et al. |
| 2008/0039795 A1 | 2/2008 | Slate et al. |
| 2008/0051711 A1 | 2/2008 | Mounce et al. |
| 2008/0051714 A1 | 2/2008 | Moberg et al. |
| 2008/0051715 A1 | 2/2008 | Young et al. |
| 2008/0097325 A1 | 4/2008 | Tanaka et al. |
| 2008/0132841 A1 | 6/2008 | Chiwanga et al. |
| 2008/0140007 A1 | 6/2008 | Glynn |
| 2008/0262434 A1 | 10/2008 | Vaillancourt |
| 2008/0312602 A1 | 12/2008 | Barrow-Williams et al. |
| 2009/0018494 A1 | 1/2009 | Nemoto et al. |
| 2009/0018505 A1 | 1/2009 | Arguedas et al. |
| 2009/0024112 A1 | 1/2009 | Edwards et al. |
| 2009/0043253 A1 | 2/2009 | Podaima |
| 2009/0076383 A1 | 3/2009 | Toews et al. |
| 2009/0149744 A1 | 6/2009 | Nemoto et al. |
| 2009/0254060 A1 | 10/2009 | Hetherington |
| 2009/0270672 A1 | 10/2009 | Fago |
| 2009/0281505 A1 | 11/2009 | Hansen et al. |
| 2009/0292246 A1 | 11/2009 | Slate et al. |
| 2009/0299288 A1 | 12/2009 | Sie et al. |
| 2009/0299290 A1 | 12/2009 | Moberg |
| 2009/0312705 A1 | 12/2009 | Grunhut et al. |
| 2009/0322545 A1 | 12/2009 | Gibson et al. |
| 2009/0326459 A1 | 12/2009 | Shipway et al. |
| 2010/0016793 A1 | 1/2010 | Jennings et al. |
| 2010/0016795 A1 | 1/2010 | McLoughlin |
| 2010/0021456 A1 | 1/2010 | Miossec et al. |
| 2010/0022955 A1 | 1/2010 | Slate et al. |
| 2010/0036318 A1 | 2/2010 | Raday et al. |
| 2010/0042054 A1 | 2/2010 | Elahi et al. |
| 2010/0112679 A1 | 5/2010 | Vandergaw |
| 2010/0152655 A1 | 6/2010 | Stamp |
| 2010/0152659 A1 | 6/2010 | Streit et al. |
| 2010/0160894 A1 | 6/2010 | Julian et al. |
| 2010/0198060 A1 | 8/2010 | Fago et al. |
| 2010/0268170 A1 | 10/2010 | Carrel et al. |
| 2010/0312195 A1 | 12/2010 | Johansen et al. |
| 2011/0004165 A1 | 1/2011 | Iio et al. |
| 2011/0023281 A1 | 2/2011 | Schraga |
| 2011/0044998 A1 | 2/2011 | Bedian et al. |
| 2011/0047153 A1 | 2/2011 | Betz |
| 2011/0092915 A1 | 4/2011 | Olson et al. |
| 2011/0097229 A1 | 4/2011 | Cauley, III et al. |
| 2011/0098655 A1 | 4/2011 | Jennings et al. |
| 2011/0137286 A1 | 6/2011 | Mudd et al. |
| 2011/0144594 A1 | 6/2011 | Sund et al. |
| 2011/0152781 A1 | 6/2011 | Brunnberg et al. |
| 2011/0160580 A1 | 6/2011 | Perkins et al. |
| 2011/0166512 A1 | 7/2011 | Both et al. |
| 2011/0184383 A1 | 7/2011 | Hasegawa |
| 2011/0190693 A1 | 8/2011 | Takatsuka et al. |
| 2011/0190702 A1 | 8/2011 | Stumber |
| 2011/0196339 A1 | 8/2011 | Hirschel et al. |
| 2011/0202011 A1 | 8/2011 | Wozencroft |
| 2011/0213315 A1 | 9/2011 | Sweeney et al. |
| 2011/0224616 A1 | 9/2011 | Slate et al. |
| 2011/0224620 A1 | 9/2011 | Johansen et al. |
| 2011/0224621 A1 | 9/2011 | Johansen et al. |
| 2011/0230833 A1 | 9/2011 | Landman et al. |
| 2011/0245761 A1 | 10/2011 | Jennings et al. |
| 2011/0257596 A1 | 10/2011 | Gaudet |
| 2011/0257604 A1 | 10/2011 | Banik |
| 2011/0264046 A1 | 10/2011 | Nyholm et al. |
| 2011/0270220 A1 | 11/2011 | Genosar |
| 2012/0035472 A1 | 2/2012 | Bruce et al. |
| 2012/0035538 A1 | 2/2012 | Elmen et al. |
| 2012/0056019 A1 | 3/2012 | Renz et al. |
| 2012/0059319 A1 | 3/2012 | Segal |
| 2012/0089119 A1 | 4/2012 | Slate et al. |
| 2012/0101439 A9 | 4/2012 | Slate et al. |
| 2012/0172815 A1 | 7/2012 | Holmqvist |
| 2012/0238961 A1 | 9/2012 | Julian et al. |
| 2012/0253314 A1 | 10/2012 | Harish et al. |
| 2012/0265142 A1 | 10/2012 | Slate et al. |
| 2012/0296286 A1 | 11/2012 | Raab et al. |
| 2012/0323176 A1 | 12/2012 | Watanabe et al. |
| 2013/0018313 A1 | 1/2013 | Kramer et al. |
| 2013/0018315 A1 | 1/2013 | Blomquist |
| 2013/0030383 A1 | 1/2013 | Keitel |
| 2013/0035647 A1 | 2/2013 | Veasey et al. |
| 2013/0046248 A1 | 2/2013 | Raab |
| 2013/0110049 A1 | 5/2013 | Cronenberg et al. |
| 2013/0110054 A1 | 5/2013 | Raab et al. |
| 2013/0112521 A1 | 5/2013 | Ekman et al. |
| 2013/0131595 A1 | 5/2013 | Ekman et al. |
| 2013/0131601 A1 | 5/2013 | Pommereau et al. |
| 2013/0190719 A1 | 7/2013 | Smith et al. |
| 2013/0190721 A1 | 7/2013 | Kemp et al. |
| 2013/0204198 A1 | 8/2013 | Burnell et al. |
| 2013/0204204 A1 | 8/2013 | Butler et al. |
| 2013/0218092 A1 | 8/2013 | Davies et al. |
| 2013/0226091 A1 | 8/2013 | Nzike et al. |
| 2013/0261558 A1 | 10/2013 | Hourmand et al. |

(56) References Cited

U.S. PATENT DOCUMENTS

| | | |
|---|---|---|
| 2013/0274668 A1 | 10/2013 | Barrow-Williams et al. |
| 2013/0289491 A1 | 10/2013 | Kramer et al. |
| 2013/0310744 A1 | 11/2013 | Brereton et al. |
| 2013/0310761 A1 | 11/2013 | Plumptre |
| 2013/0317430 A1 | 11/2013 | Brereton et al. |
| 2013/0317480 A1 | 11/2013 | Reber et al. |
| 2013/0324935 A1 | 12/2013 | Brereton et al. |
| 2013/0338601 A1 | 12/2013 | Cowe |
| 2014/0046259 A1 | 2/2014 | Reber et al. |
| 2014/0148784 A1 | 5/2014 | Anderson et al. |
| 2014/0194854 A1 | 7/2014 | Tsals |
| 2014/0236087 A1 | 8/2014 | Alderete et al. |
| 2014/0257197 A1 | 9/2014 | Madsen et al. |
| 2014/0276448 A1 | 9/2014 | Muller-Pathle et al. |
| 2014/0296825 A1 | 10/2014 | Lemaire et al. |
| 2014/0303556 A1 | 10/2014 | Travanty |
| 2014/0316369 A1 | 10/2014 | Centeno et al. |
| 2014/0330203 A1 | 11/2014 | McLoughlin et al. |
| 2014/0330216 A1 | 11/2014 | Weaver et al. |
| 2014/0336590 A1 | 11/2014 | Hourmand et al. |
| 2014/0364808 A1 | 12/2014 | Niklaus et al. |
| 2015/0045729 A1 | 2/2015 | Denzer et al. |
| 2015/0080809 A1 | 3/2015 | Dasbach et al. |
| 2015/0136809 A1 | 5/2015 | Hamann et al. |
| 2015/0141923 A1 | 5/2015 | Wurmbauer et al. |
| 2015/0151046 A1 | 6/2015 | Nagel et al. |
| 2015/0165130 A1 | 6/2015 | Butler et al. |
| 2015/0217057 A1 | 8/2015 | Hogdahl |
| 2016/0022914 A1 | 1/2016 | Mounce et al. |
| 2016/0120751 A1 | 5/2016 | Mounce et al. |
| 2016/0271326 A1 | 9/2016 | Slate et al. |
| 2017/0043105 A1 | 2/2017 | Elmen |
| 2017/0157326 A1 | 6/2017 | Slate et al. |

FOREIGN PATENT DOCUMENTS

| | | |
|---|---|---|
| CA | 2594627 | 8/2006 |
| DE | 102007061775 A1 | 7/2009 |
| EP | 1227423 A1 | 7/2002 |
| EP | 1518575 A1 | 3/2005 |
| ES | 2121536 A1 | 11/1998 |
| FR | 2390175 A2 | 12/1978 |
| FR | 2581548 A1 | 11/1986 |
| FR | 2592307 A1 | 7/1987 |
| FR | 2622457 A1 | 5/1989 |
| FR | 2716375 A1 | 8/1995 |
| IL | 87559 A | 6/1993 |
| IL | 877559 | 6/1993 |
| JP | S63139563 A | 6/1988 |
| JP | 2008157 | 1/1990 |
| JP | H07503384 A | 4/1995 |
| JP | H07185000 A | 7/1995 |
| JP | H11-276583 A | 10/1999 |
| JP | 2000-237309 A | 9/2000 |
| JP | 2001518366 A | 10/2001 |
| JP | 20020531228 A | 9/2002 |
| JP | 2002543931 A | 12/2002 |
| JP | 2003220142 A | 8/2003 |
| JP | 2005-131007 A | 5/2005 |
| JP | 2005514082 A | 5/2005 |
| JP | 2005-287676 A | 10/2005 |
| JP | 2006507061 A | 3/2006 |
| JP | 2006-523507 A | 10/2006 |
| JP | 2006528040 A | 12/2006 |
| JP | 2007500561 A | 1/2007 |
| JP | 2007-507260 A | 3/2007 |
| JP | 2007111518 A | 5/2007 |
| JP | 2007529243 A | 10/2007 |
| JP | 2008508961 A | 3/2008 |
| JP | 2010-051828 A | 3/2010 |
| JP | 2010511414 A | 4/2010 |
| JP | 2015186876 A | 10/2015 |
| JP | 2017-023813 A | 2/2017 |
| TW | 200833383 A | 8/2008 |
| TW | 200833387 A | 8/2008 |
| TW | 200836787 A | 9/2008 |
| TW | 200840606 A | 10/2008 |
| TW | 201004667 A | 2/2010 |
| TW | 201004668 A | 2/2010 |
| WO | WO-1986006967 A1 | 12/1986 |
| WO | WO-1987003494 A1 | 6/1987 |
| WO | WO-1987007160 A1 | 12/1987 |
| WO | WO-1991018634 A1 | 12/1991 |
| WO | WO-1992006725 A1 | 4/1992 |
| WO | WO-1992008506 A1 | 5/1992 |
| WO | WO-1992021392 A1 | 12/1992 |
| WO | WO-1993002728 A1 | 2/1993 |
| WO | WO-1993013817 A1 | 7/1993 |
| WO | WO-1993024160 A1 | 12/1993 |
| WO | WO-1993025256 A1 | 12/1993 |
| WO | WO-1994006494 A1 | 3/1994 |
| WO | 94/07553 A1 | 4/1994 |
| WO | WO-1995021645 A1 | 8/1995 |
| WO | WO-1995025555 A1 | 9/1995 |
| WO | WO-1995031235 A1 | 11/1995 |
| WO | WO-1995034333 A2 | 12/1995 |
| WO | WO-1996000594 A1 | 1/1996 |
| WO | WO-1996021482 A2 | 7/1996 |
| WO | WO-1996026754 A2 | 9/1996 |
| WO | WO-1996038190 A1 | 12/1996 |
| WO | WO-1997007839 A1 | 3/1997 |
| WO | WO-1997031665 A1 | 9/1997 |
| WO | WO-1998013077 A2 | 4/1998 |
| WO | WO-1998017332 A2 | 4/1998 |
| WO | WO-1998021408 A1 | 5/1998 |
| WO | 98/28032 A1 | 7/1998 |
| WO | WO-99/17823 A1 | 4/1999 |
| WO | WO-1999017823 A1 | 4/1999 |
| WO | WO-1999020327 A2 | 4/1999 |
| WO | WO-1999021600 A2 | 5/1999 |
| WO | WO-99/65548 A1 | 12/1999 |
| WO | WO-2000002605 | 1/2000 |
| WO | WO-2000009186 A2 | 2/2000 |
| WO | WO-2000024441 | 5/2000 |
| WO | WO-2000025846 | 5/2000 |
| WO | WO-2001000261 | 1/2001 |
| WO | WO-2001037903 | 5/2001 |
| WO | WO-01/41835 A2 | 6/2001 |
| WO | WO-2001041835 | 6/2001 |
| WO | WO-01/089634 A2 | 11/2001 |
| WO | WO-2001089634 | 11/2001 |
| WO | WO-02/07812 A2 | 1/2002 |
| WO | WO-2002007812 | 1/2002 |
| WO | WO-2002/11792 A1 | 2/2002 |
| WO | WO-02/49691 A2 | 6/2002 |
| WO | WO-2002049691 | 6/2002 |
| WO | WO-2002/060513 A2 | 8/2002 |
| WO | WO-02/092153 A2 | 11/2002 |
| WO | WO-2002092153 | 11/2002 |
| WO | 03/03934 A1 | 1/2003 |
| WO | WO-03/006099 A1 | 1/2003 |
| WO | WO-03/008023 A1 | 1/2003 |
| WO | WO-2003006099 | 1/2003 |
| WO | WO-2003008023 | 1/2003 |
| WO | WO-2003/024385 A1 | 3/2003 |
| WO | WO-03/039634 A1 | 5/2003 |
| WO | WO-03/047663 A2 | 6/2003 |
| WO | WO-2003/047659 A1 | 6/2003 |
| WO | WO-2003047663 | 6/2003 |
| WO | WO-03/90509 A2 | 11/2003 |
| WO | WO-2003090509 | 11/2003 |
| WO | WO-03/103749 A2 | 12/2003 |
| WO | WO-2003103749 | 12/2003 |
| WO | WO-2004/004809 A1 | 1/2004 |
| WO | WO-2004/004825 A2 | 1/2004 |
| WO | WO-2004/069303 A2 | 8/2004 |
| WO | 2004/084795 A1 | 10/2004 |
| WO | WO-2004/108193 A1 | 12/2004 |
| WO | WO-2005/032449 A1 | 4/2005 |
| WO | WO-2005/053771 A2 | 6/2005 |
| WO | WO-2005/070481 A1 | 8/2005 |
| WO | WO-2005/079440 A2 | 9/2005 |
| WO | WO-2005089831 A1 | 9/2005 |
| WO | WO-2005/094923 A1 | 10/2005 |

(56) References Cited

FOREIGN PATENT DOCUMENTS

| | | |
|---|---|---|
| WO | WO-2006015501 A1 | 2/2006 |
| WO | WO-2006017732 A2 | 2/2006 |
| WO | WO-2006020609 A1 | 2/2006 |
| WO | WO-2006062788 A2 | 6/2006 |
| WO | WO-2006063015 A2 | 6/2006 |
| WO | WO-2006084821 A2 | 8/2006 |
| WO | WO-2006086774 A2 | 8/2006 |
| WO | WO-2007002053 A2 | 1/2007 |
| WO | WO-2007044980 A2 | 4/2007 |
| WO | WO-2007047200 A1 | 4/2007 |
| WO | WO-2007053779 A2 | 5/2007 |
| WO | WO-2007/075677 A2 | 7/2007 |
| WO | WO-2007099044 A1 | 9/2007 |
| WO | WO-2007/126851 A2 | 11/2007 |
| WO | WO-2007/138313 A1 | 12/2007 |
| WO | WO-2007138299 A1 | 12/2007 |
| WO | WO-2007140610 A1 | 12/2007 |
| WO | WO-2008/004670 A1 | 1/2008 |
| WO | WO-2008021776 A2 | 2/2008 |
| WO | WO-2008024810 A2 | 2/2008 |
| WO | WO-2008048750 A2 | 4/2008 |
| WO | WO-2008064092 A2 | 5/2008 |
| WO | WO-2008075033 A1 | 6/2008 |
| WO | WO-2008083313 A2 | 7/2008 |
| WO | WO-2008093063 A2 | 8/2008 |
| WO | WO-2008094984 A2 | 8/2008 |
| WO | WO-2008095124 A1 | 8/2008 |
| WO | WO-2008/113772 A1 | 9/2008 |
| WO | WO-2008107670 A2 | 9/2008 |
| WO | WO-2008139458 A2 | 11/2008 |
| WO | WO-2008139460 A2 | 11/2008 |
| WO | WO-2008146021 A1 | 12/2008 |
| WO | WO-2009006725 A1 | 1/2009 |
| WO | WO-2009019437 A1 | 2/2009 |
| WO | WO-2009097325 A1 | 8/2009 |
| WO | WO-2009/125879 A1 | 10/2009 |
| WO | WO-2009143255 A1 | 11/2009 |
| WO | WO-2010023481 A1 | 3/2010 |
| WO | WO-2010026414 A1 | 3/2010 |
| WO | WO-2010076275 A1 | 7/2010 |
| WO | WO-2010091133 A2 | 8/2010 |
| WO | WO-2010/099850 A1 | 9/2010 |
| WO | WO-2010100213 A1 | 9/2010 |
| WO | WO-2010127449 A1 | 11/2010 |
| WO | WO-2011/014525 A2 | 2/2011 |
| WO | 2011/056888 A2 | 5/2011 |
| WO | WO-2011057065 A1 | 5/2011 |
| WO | WO-2011/089206 A2 | 7/2011 |
| WO | WO-2012000871 A1 | 1/2012 |
| WO | WO-2012000940 A2 | 1/2012 |
| WO | 2012/022771 A2 | 2/2012 |
| WO | 2012/080481 A1 | 6/2012 |
| WO | WO-2012/103140 A1 | 8/2012 |
| WO | WO-2012145685 A1 | 10/2012 |
| WO | WO-2012164389 A2 | 12/2012 |
| WO | WO-2012164394 A2 | 12/2012 |
| WO | WO-2012164397 A1 | 12/2012 |
| WO | WO-2013001378 A2 | 1/2013 |
| WO | WO-2013034984 A2 | 3/2013 |
| WO | WO-2013034986 A2 | 3/2013 |
| WO | WO-2013065055 A1 | 5/2013 |
| WO | WO-2014143815 A2 | 9/2014 |
| WO | WO-2014144096 A1 | 9/2014 |

OTHER PUBLICATIONS

"Final Office Action" dated Oct. 18, 2016 issued related U.S. Appl. No. 13/269,150.
"Office Action", dated Mar. 8, 2015, issued in related U.S. Appl. No. 13/269,750.
Australian Patent Application No. 2017202210, Examination Report No. 1, dated Oct. 25, 2018.
Canadian Patent Application No. 2724641, Office Action, dated May 27, 2019.
European Search Report and Search Opinion Received for EP Application No. 19154409.7, dated Oct. 31, 2019, 9 pages.
International Application No. PCT/US09/44693, filed May 20, 2009, entitled, "Autoinjector System", Slate, et al.
International Patent Application No. PCT/US09/44693, Written Opinion of the International Searching Authority, dated May 20, 2009.
Japanese Patent Application No. 2017-089529, Notice of Reasons for Rejection, dated Apr. 2, 2018.
Japanese Patent Application No. 2017-089529, Notice of Reasons for Rejection, dated Sep. 14, 2018.
Michael Denzer et al., related copending U.S. Appl. No. 14/112,479, 371(c) dated Sep. 17, 2014.
Non-Final Office Action issued in related U.S. Appl. No. 12/993,163, dated Sep. 11, 2014.
Office Action received for European Patent Application No. 14765760.5, dated Jul. 9, 2019, 4 pages.
Related International Patent Application No. PCT/US2014/028363, dated Mar. 14, 2014.
Search Report for Taiwan Patent Application No. 106100512, Office Action, dated Dec. 4, 2017.
U.S. Appl. filed Apr. 24, 2012, John B. Slate et al., U.S. Appl. No. 13/454,531.
U.S. Appl. filed Feb. 23, 2017, John B. Slate et al., U.S. Appl. No. 15/440,420.
U.S. Appl. filed Jul. 23, 2008, John B. Slate et al., U.S. Appl. No. 12/178,447.
U.S. Appl. filed May 27, 2011, entitled, "Autoinjector System," of Slate et al., U.S. Appl. No. 12/993,163.
U.S. Appl. filed May 27, 2016, John B. Slate et al., U.S. Appl. No. 15/167,068.
U.S. Appl. filed Oct. 10, 2011, John B. Slate et al., U.S. Appl. No. 13/269,750.
U.S. Appl. No. 15/167,068, Final Office Action, dated Apr. 24, 2019.
Unpublished related U.S. Appl. No. 14/777,255.
U.S. Appl. No. 15/167,068, Non-final Office Action, dated Oct. 18, 2018.
U.S. Appl. No. 15/167,068, Nonfinal Office Action, dated Oct. 9, 2019.
U.S. Appl. No. 15/782,925, Final Office Action, dated Oct. 11, 2019.
Japanese Patent Application No. 2018-188224, Notice of Reasons for Rejection, dated Aug. 5, 2019.
Canadian Patent Application No. 3021845, Examiner's Report, dated Aug. 19, 2019.
Australian Patent Application No. 2009249027, Notice of Acceptance, dated Aug. 7, 2014.
Australian Patent Application No. 2009249027, Office Action, dated Jul. 24, 2013.
Australian Patent Application No. 2012245231, Notice of Allowance, dated Oct. 4, 2016.
Australian Patent Application No. 2012245231, Office Action, dated Jul. 5, 2016.
Australian Patent Application No. 2012245231, Office Action, dated Oct. 19, 2015.
Australian Patent Application No. 2014268139, Office Action, dated Jul. 19, 2016.
Australian Patent Application No. 2014268140, Office Action, dated Jul. 22, 2016.
Australian Patent Application No. 2014268140, Office Action, dated Sep. 2, 2016.
Australian Patent Application No. 2017200125, Examination Report No. 1, dated Sep. 18, 2017.
Canadian patent application No. 2724641, Examination Report, dated Dec. 15, 2016.
Canadian patent application No. 2724641, Examination Report, dated Sep. 29, 2017.
Canadian Patent Application No. 2724641, Office Action, dated Jun. 4, 2015.
Canadian patent application No. 2833748, Examination Report, dated May 2, 2017.
Canadian Patent Application No. 2833748, Office Action, dated Aug. 12, 2016.

(56) References Cited

OTHER PUBLICATIONS

Canadian Patent Application No. 2833748, Office Action, dated Nov. 23, 2015.
European patent application No. 09751483.0, Extended Search Report, dated Aug. 1, 2013.
European Patent Application No. 09751483.0, Office Action, dated Apr. 10, 2015.
European patent application No. 09751483.0, Office Action, dated Aug. 1, 2016.
European Patent Application No. 09751483.0, Office Action, dated May 14, 2014.
European Patent Application No. 09751483.0, Office Action, dated Nov. 16, 2015.
European patent application No. 12774589.1, Extended Search Report, dated Feb. 23, 2015.
European Patent Application No. 12774589.1, Extended Search Report, dated Jul. 8, 2015.
European patent application No. 14763010.7, Extended Search Report and Opinion, dated Jan. 10, 2017.
European patent application No. 14763010.7, Partial Supplementary Search Report, dated Oct. 24, 2016.
European patent application No. 14765760.5, Extended Search Report, dated Jan. 11, 2017.
European patent application No. 14765760.5, Partial Supplementary Search Report, dated Oct. 24, 2016.
European Patent Application No. 9751483.0, Office Action, dated Aug. 1, 2016.
International Patent Application No. PCT/US2014/027950, International Preliminary Report on Patentability, dated Jun. 15, 2015.
International Patent Application No. PCT/US09/44693, International Preliminary Report on Patentability, dated Nov. 23, 2010.
International Patent Application No. PCT/US09/44693, International Search Report, dated Jul. 21, 2009.
International Patent Application No. PCT/US14/27950, International Preliminary Report on Patentability, dated Sep. 15, 2015.
International Patent Application No. PCT/US2012/034535, International Preliminary Report on Patentability, dated Oct. 22, 2013.
International Patent Application No. PCT/US2012/34535, International Search Report and Written Opinion, dated Aug. 17, 2012.
International Patent Application No. PCT/US2014/027950, International Search Report and Written Opinion, dated Oct. 7, 2014.
International Patent Application No. PCT/US2014/028363, International Search Report and Written Opinion, dated Aug. 18, 2014.
Japanese Patent Application No. 2011-510683, Notice of Allowance, dated Oct. 5, 2015.
Japanese Patent Application No. 2011-510683, Office Action, dated Jul. 30, 2013.
Japanese Patent Application No. 2011-510683, Office Action, dated Jun. 30, 2014.
Japanese Patent Application No. 2014-021052, Notice of Allowance, dated Aug. 24, 2015.
Japanese Patent Application No. 2014-021052, Office Action, dated Jan. 5, 2015.
Japanese Patent Application No. 2014-506591, Notice of Allowance, dated Oct. 3, 2016.
Japanese Patent Application No. 2014-506591, Office Action, dated Jan. 4, 2016.
Japanese Patent Application No. 2014021052, Final Office Action, dated Apr. 20, 2015.
Japanese Patent Application No. 2015-171851, Decision of Rejection, dated Feb. 6, 2017.
Japanese Patent Application No. 2015-186876, Office Action, dated Jul. 15, 2016.
Japanese Patent Application No. 2016-214237, Notice of Reasons for Rejection, dated Sep. 4, 2017.
Mexican Application No. 2010012691, Office Action, dated Sep. 24, 2014.
Mexican Patent Application No. 2010012691, Office Action, dated Feb. 10, 2014.
Taiwan Patent Application No. 103109332, Office Action, dated Aug. 22, 2016.
Taiwan Patent Application No. 103109475, Office Action, dated Aug. 26, 2016.
U.S. Appl. No. 12/123,888, Final Office Action, dated Apr. 8, 2010.
U.S. Appl. No. 12/123,888, Final Office Action, dated Jun. 8, 2011.
U.S. Appl. No. 12/123,888, Non-Final Office Action, dated Dec. 22, 2010.
U.S. Appl. No. 12/123,888, Notice of Allowance, dated Jan. 12, 2012.
U.S. Appl. No. 12/123,888, Office Action, dated Oct. 5, 2009.
U.S. Appl. No. 12/178,447, Final Office Action, dated Mar. 30, 2010.
U.S. Appl. No. 12/178,447, Non-Final Office Action, dated Dec. 22, 2010.
U.S. Appl. No. 12/178,447, Non-Final Office Action, dated Oct. 15, 2009.
U.S. Appl. No. 12/178,447, Notice of Allowance, dated Apr. 6, 2011.
U.S. Appl. No. 12/178,447, Notice of Allowance, dated Jun. 24, 2011.
U.S. Appl. No. 12/454,531, Non-Final Office Action, dated Sep. 13, 2013.
U.S. Appl. No. 12/993,163, Final Office Action, dated Feb. 22, 2016.
U.S. Appl. No. 12/993,163, Non-Final Office Action, dated Dec. 27, 2013.
U.S. Appl. No. 12/993,163, Non-Final Office Action, dated Jul. 28, 2016.
U.S. Appl. No. 12/993,163, Office Action, dated May 8, 2015.
U.S. Appl. No. 13/269,740, Restriction Requirement, dated Apr. 2, 2013.
U.S. Appl. No. 13/269,740, Office Action, dated May 20, 2013.
U.S. Appl. No. 13/269,750, Final Office Action, dated Dec. 26, 2013.
U.S. Appl. No. 13/269,750, Final Office Action, dated Oct. 18, 2016.
U.S. Appl. No. 13/269,750, Non Final Office Action, dated May 3, 2016.
U.S. Appl. No. 13/269,750, Non-Final Office Action, dated Aug. 21, 2014.
U.S. Appl. No. 13/269,750, Non-final Office Action, dated Jun. 21, 2013.
U.S. Appl. No. 13/269,750, Notice of Allowance, dated Feb. 8, 2017.
U.S. Appl. No. 13/269,750, Office Action, dated Aug. 10, 2015.
U.S. Appl. No. 13/269,750, Office Action, dated Mar. 12, 2015.
U.S. Appl. No. 13/269,750, Office Action, dated Nov. 18, 2015.
U.S. Appl. No. 13/454,531, Final Office Action, dated Sep. 23, 2016.
U.S. Appl. No. 13/454,531, Non-Final Office Action, dated Dec. 28, 2012.
U.S. Appl. No. 13/454,531, Non-Final Office Action, dated Mar. 17, 2016.
U.S. Appl. No. 13/454,531, Notice of Allowance, dated Oct. 5, 2015.
U.S. Appl. No. 13/454,531, Office Action, dated Apr. 21, 2015.
U.S. Appl. No. 13/454,531, Office Action, dated Oct. 7, 2014.
U.S. Appl. No. 14/112,479, Final Office Action, dated Feb. 27, 2017.
U.S. Appl. No. 14/112,479, Nonfinal Office Action, dated Jul. 12, 2017.
U.S. Appl. No. 14/112,479, Nonfinal Office Action, dated Jul. 29, 2016.
U.S. Appl. No. 29/548,507, Denzer et al., dated Dec. 14, 2015.
U.S. Appl. No. 29/548,508, Denzer et al., dated Feb. 14, 2015.
European patent application No. 12774589.1, Examination Report, dated Oct. 31, 2017.
International Patent Application No. PCT/US2012/34535, International Search Report, dated Aug. 17, 2012.
Japanese Patent Application No. 2019-070580, Notice of Reasons for Rejection, dated Feb. 25, 2020.
Australian Patent Application No. 2018253467, Examination Report No. 1, dated Dec. 6, 2019.

(56) References Cited

OTHER PUBLICATIONS

European Patent Application No. 19191313.6, European Search Report, dated Dec. 16, 2019.
Japanese Patent Application No. 2016-502669, Notice of Reasons for Rejection, dated Jan. 14, 2020., Jan 14, 2020.
Japanese Patent Application No. 2018-086731, Decision of Rejection, dated Feb. 3, 2020.
Japanese Patent Application No. 2018-228060, Notice of Reasons for Rejection, dated Oct. 21, 2019.
U.S. Appl. No. 15/167,068, Nonfinal Office Action, dated Feb. 14, 2020.
U.S. Appl. No. 15/952,296, Nonfinal Office Action, dated Jan. 14, 2020.

AUTOINJECTOR APPARATUS

RELATED APPLICATIONS

This is a continuation of U.S. patent application Ser. No. 14/112,479, filed Sep. 17, 2014, which is the U.S. national phase of International Patent Application No. PCT/US2012/034535, filed Apr. 20, 2012, which claims the priority benefit of U.S. Provisional Application No. 61/477,553, filed Apr. 20, 2011, the entire contents of each of which are incorporated herein by reference.

FIELD

The present disclosure relates to an autoinjector apparatus. More particularly, the present disclosure relates to an autoinjector apparatus having a reusable autoinjector and a single-use cassette useable with the autoinjector, which conceals the injection needle of a hypodermic syringe before and after an injection.

BACKGROUND

Pre-filled hypodermic syringes provide several advantages for the home-use market. These advantages include that pre-filled syringes may be prepared for each medicament with exactly the required dosage. Further, they are easily operated, by merely advancing the stopper of the syringe. Aside from the costs of the particular medication used, pre-filled syringes are also economically manufactured. Consequently, all these advantages make pre-filled syringes commercially appealing.

Nevertheless, pre-filled syringes also have a significant drawback in the marketplace. Specifically, many users are either frightened by an exposed needle or feel they are inherently incapable of performing an injection. Because of aversions to exposed needles, as well as health and safety issues that may be involved, various types of injectors and other devices have been developed for the specific purpose of concealing needles from the user and automating the injection task to assist the user in performing the injection.

In order to inject a fluid medicament into a patient when using a hypodermic syringe, generally three separate and distinct tasks must be performed. These are: 1) insertion of the needle into the patient; 2) injection of the fluid medicament from the syringe into the patient; and 3) withdrawal of the needle after the injection has been completed. For each task, the magnitude and direction of forces on the syringe, as well as the location of their application, are different from the other tasks. For instance, compare the task of inserting the needle, with the task of injecting the fluid medicament. Insertion of the needle requires that only minimal forces be applied on the syringe, and that they be applied for only a very short period of time. On the other hand, injection of the medicament requires a much greater force be applied. Further, this force must be applied on the plunger of the syringe for what will typically be a relatively longer period of time. In comparison with both of these tasks, needle withdrawal requires the application of a force in the opposite direction. These, and other similar considerations, become important when the injection process is to be automated.

Springs for generating forces on a syringe in an automated process have been used heretofore for various purposes. A characteristic of springs, however, is that the magnitude and direction of a spring force are not variable. Consequently, springs do not lend themselves to multi-tasking operations. This limitation is particularly notable in a syringe injection, which requires precise control of sequential forces of different magnitude (needle insertion and medicament injection). This limitation can be particularly problematic where it may be desirable to use the same device, at different times, to inject different medications with different fluid viscosities.

In addition to these mechanical considerations, the design of an autoinjector requires user-friendly considerations. In particular, it is desirable that the injection needle of a syringe be operationally concealed from the view of a user. Preferably, this concealment is maintained before, during and after an injection procedure. Further, it is desirable that operation of the syringe be limited to only those times when the syringe is properly positioned for an injection.

Accordingly, an improved autoinjector apparatus is needed.

SUMMARY

The present disclosure relates to a single-use cassette for use with an autoinjector. The cassette comprises: a housing; an inner sleeve disposed in the housing and movable between first and second positions, wherein the inner sleeve is capable of having a syringe disposed therein; and a lock cap for securing the syringe in the inner sleeve, the lock cap affixed to a distal end of the inner sleeve and capable of contact with the distal end of the syringe.

In one embodiment of the cassette, the lock cap comprises an elastomeric bumper that is capable of contact with the distal end of the syringe.

In one embodiment of the cassette, the inner sleeve comprises at least one receptacle at the distal end thereof and the lock cap comprises at least one arm member inserted into the receptacle.

In one embodiment of the cassette, the at least one arm member of the lock cap comprises a barb arrangement for gripping an inner surface of the receptacle of the inner sleeve.

In one embodiment of the cassette, the cassette further comprises a syringe having a barrel and an injection needle disposed in the inner sleeve.

In one embodiment of the cassette, the cassette further comprises a shield remover extending through an opening in a proximal end of the housing for removing a needle shield from the syringe.

In one embodiment of the cassette, the shield remover comprises a spring-biased tab, the tab disposed within an aperture defined in a wall of the housing.

In one embodiment of the cassette, the shield remover comprises an elongated body having a proximal end and a distal end, the distal end comprising at least one flexible tongue that expands outwardly when the shield remover is removed from the cassette to prevent the shield remover from being reinserted into the cassette.

In one embodiment of the cassette, the cassette further comprises a syringe having a barrel and an injection needle.

In one embodiment of the cassette, the cassette further comprises a therapeutic product in the syringe.

In one embodiment of the cassette, the therapeutic product is selected from the group consisting of Epogen®, Aranesp®, Enbrel® Neulasta®, Neupogen®, Nplate®, Vectibix®, Sensipar®, Xgeva® and Prolia®.

In one embodiment of the cassette, the therapeutic product is an antibody to IL-17 Receptor A.

In one embodiment of the cassette, the therapeutic product is an antagonist of angiopoietin-2 (e.g., AMG 36).

In one embodiment of the cassette, the therapeutic product is a TNF blocker or inhibitor.

In one embodiment of the cassette, the TNF blocker or inhibitor is etanercept.

In one embodiment of the cassette, the TNF blocker or inhibitor is adalimumab, certolizumab, golimumab or infliximab.

In one embodiment of the cassette, the cassette further comprises a cassette identification arrangement on a surface of the housing to enable the autoinjector to identify the cassette.

In one embodiment of the cassette, the cassette identification arrangement comprises at least one projection.

The present disclosure further relates to an apparatus for injection of a therapeutic product. The apparatus comprises: an autoinjector; and a single-use cassette for use with the injector, the cassette comprising: a housing; an inner sleeve disposed in the housing and movable between first and second positions; a syringe disposed in the inner sleeve; and a lock cap for securing the syringe in the inner sleeve, the lock cap affixed to a distal end of the inner sleeve and in contact with the distal end of the syringe.

In one embodiment of the apparatus, the lock cap comprises an elastomeric bumper that contacts the distal end of the syringe.

In one embodiment of the apparatus, the inner sleeve comprises at least one receptacle at the distal end thereof and the lock cap comprises at least one arm member inserted into the receptacle.

In one embodiment of the apparatus, the at least one arm member of the lock cap comprises a barb arrangement for gripping an inner surface of the receptacle of the inner sleeve.

In one embodiment of the apparatus, the cassette further comprises a shield remover extending through an opening in a proximal end of the housing for removing a needle shield from the syringe.

In one embodiment of the apparatus, the shield remover comprises a spring-biased tab, the tab disposed within an aperture defined in a wall of the housing to prevent removal of the shield remover from the cassette.

In one embodiment of the apparatus, the autoinjector comprises a pin for pushing the tab out of the aperture defined in the wall of the housing when the cassette is placed in the injector to thereby allow the shield remover to be removed from the cassette.

In one embodiment of the apparatus, the shield remover comprises an elongated body having a proximal end and a distal end, the distal end comprising at least one flexible tongue that expands outwardly when the shield remover is removed from the cassette to prevent the shield remover from being reinserted into the cassette.

In one embodiment of the apparatus, the apparatus further comprises a therapeutic product in the syringe.

In one embodiment of the apparatus, the therapeutic product is selected from the group consisting of Epogen®, Aranesp®, Enbrel® Neulasta®, Neupogen®, Nplate®, Vectibix®, Sensipar®, Xgeva®, and Prolia®.

In one embodiment of the apparatus, the therapeutic product is an antibody to IL-17 Receptor A.

In one embodiment of the apparatus, the therapeutic product is an antagonist to angiopoietin-2 (e.g., AMG 386).

In one embodiment of the apparatus, the therapeutic product is a TNF blocker or inhibitor.

In one embodiment of the apparatus, the TNF blocker or inhibitor is etanercept.

In one embodiment of the apparatus, the TNF blocker or inhibitor is adalimumab, certolizumab, golimumab or infliximab.

In one embodiment of the apparatus, the cassette further comprising a cassette identification arrangement on a surface of the housing to enable the autoinjector to identify the cassette.

In one embodiment of the apparatus, the cassette identification arrangement comprises at least one projection.

In one embodiment of the apparatus, the autoinjector comprises a detector for reading the cassette identification arrangement to identify the cassette.

The present disclosure further relates to an apparatus for injection of a therapeutic product. The apparatus comprises: an autoinjector; and a single-use cassette for use with the injector, the cassette comprising: a housing; a sleeve disposed in the housing and movable between first and second positions; a syringe disposed in the sleeve; and a shield remover extending through an opening in a proximal end of the housing for removing a needle shield from the syringe.

The present disclosure further relates to a single-use cassette for use with an autoinjector. The cassette comprises: a housing; a sleeve disposed in the housing and movable between first and second positions, wherein the sleeve is capable of having a syringe disposed therein; and a shield remover extending through an opening in a proximal end of the housing for removing a needle shield from the syringe.

BRIEF DESCRIPTION OF THE FIGURES

The accompanying figures show a preferred embodiment according to the present disclosure and are exemplary rather than limiting.

DETAILED DESCRIPTION

Figure 1:
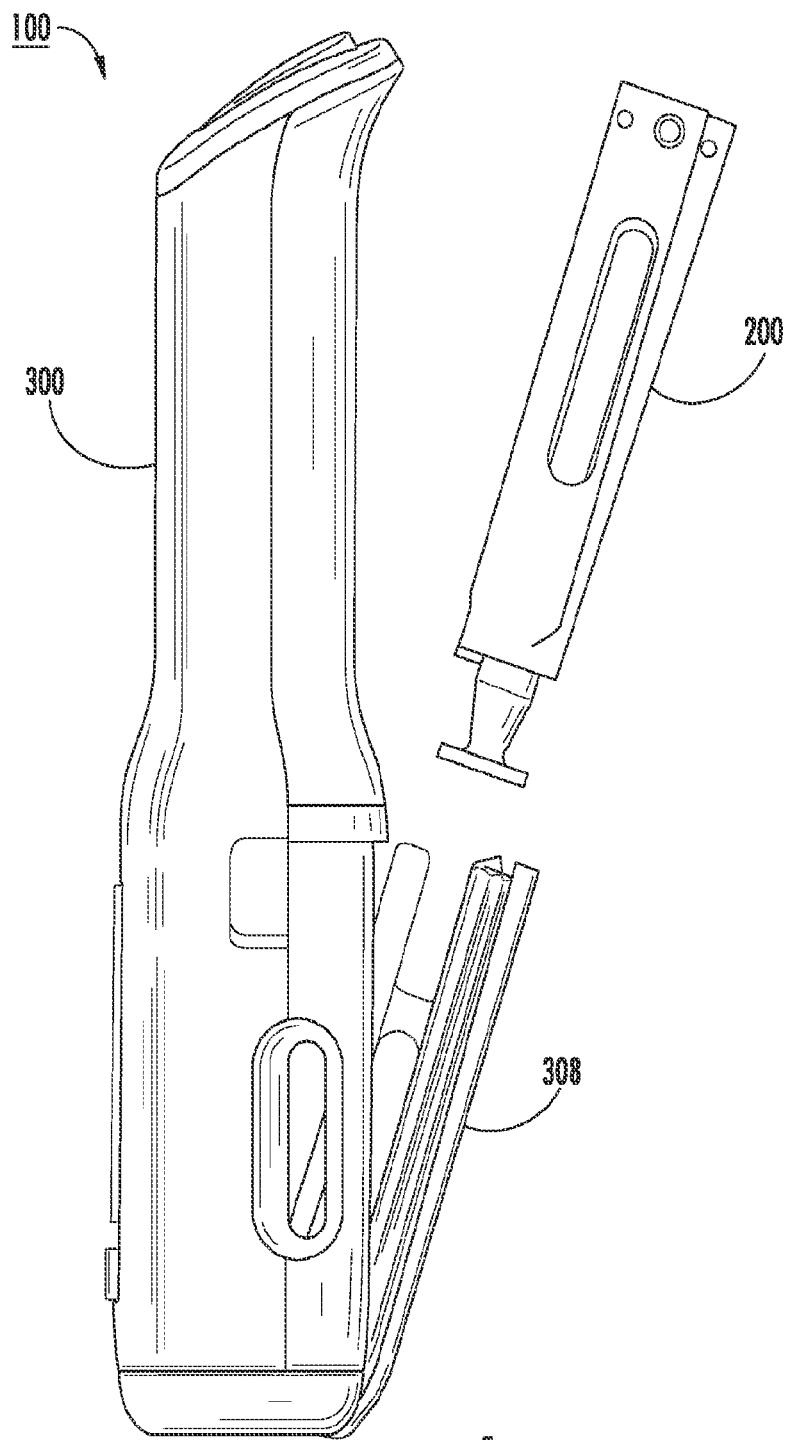
FIG. 1 is an elevational side view of an exemplary embodiment of an autoinjector apparatus 100 comprising an autoinjector 300 and a cassette 200.
Figure 6A:
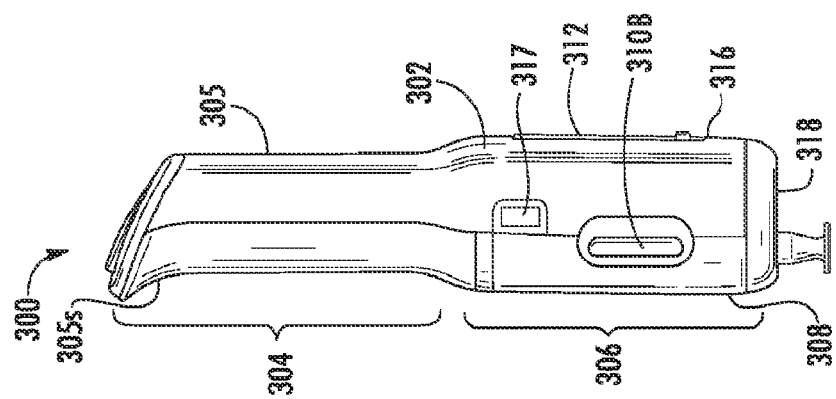
FIG. 6A is a front elevational view of an exemplary embodiment of the autoinjector 300 which may comprise a casing 302, a handle section 304, a handle 305, a cassette receiving section 306, a cassette door 308, a user interface 312, a speaker aperture 314, a speed selector switch 316, and an end wall 318.
Figure 6B:
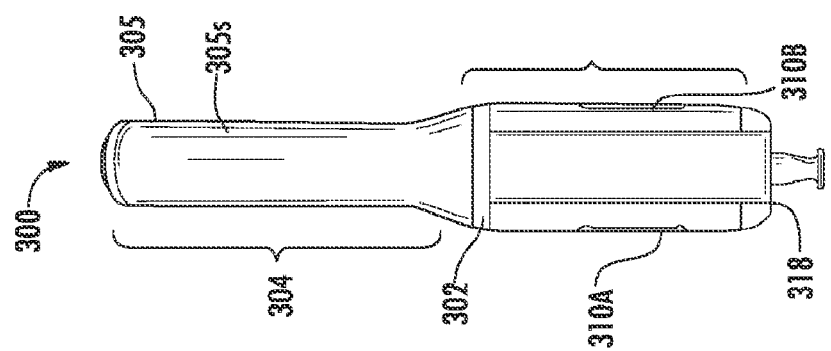
FIG. 6B is an elevational view of a first side of the autoinjector 300 of FIG. 6A illustrating the casing 302, the handle section 304, the handle 305, a soft grip area 305S, the cassette receiving section 306, the cassette door 308, a window 310A, the user interface 312, a settings/mute switch 315, the speed selector switch 316, and the end wall 318.
Figure 6C:
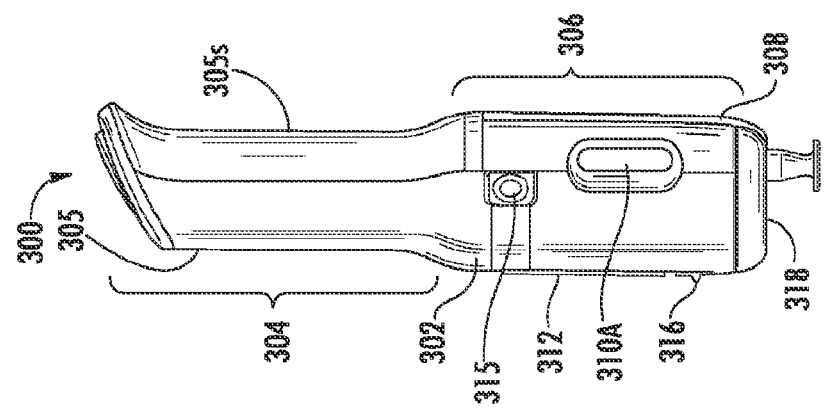
FIG. 6C is a rear elevational view of the autoinjector 300 of FIG. 6A illustrating the casing 302, the handle section 304, the handle 305, the soft grip area 305S, the cassette receiving section 306, windows 310A and 310B, and the end wall 318.
Figure 6D:
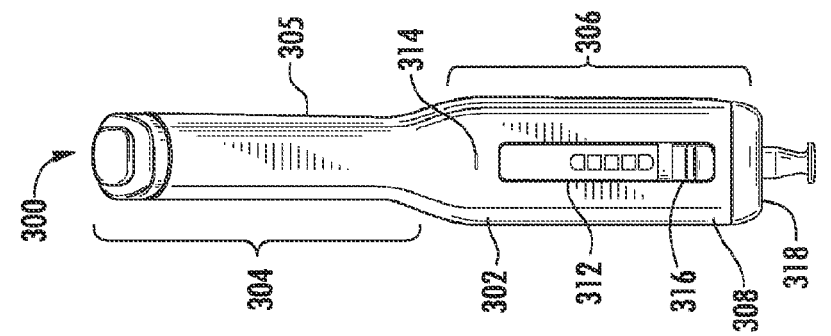
FIG. 6D is an elevational view of a second side of the autoinjector 300 of FIG. 6A illustrating the casing 302, the handle section 304, the handle 305, the soft grip area 305S, the cassette receiving section 306, the cassette door 308, a window 310B, the user interface 312, an eject button 317, the speed selector switch 316, and the end wall 318.

FIG. 1 illustrates an elevational view of an exemplary embodiment of an autoinjector apparatus 100 according to the present disclosure. The autoinjector apparatus 100 comprises an autoinjector 300 and a cassette 200. The autoinjector 300 may comprise a cassette door 308, which in an open position, (as shown) allows insertion therein of the cassette 200, and which in a closed position (e.g., FIG. 6B), aligns the cassette 200 with insertion and extrusion drives 330 and 340, respectively (FIG. 8) of the autoinjector 300. The autoinjector 300 may be constructed and adapted for hand-held operation and be reusable. The cassette 200 may be constructed and adapted to house and protect a syringe 260 (e.g., FIG. 2A), which may be prefilled with a predetermined dose of a pharmaceutical product. The cassette 200 facilitates and enables easy use of the syringe with the autoinjector 300 and helps prevent needle sticks before and after use. Moreover, the cassette 200 may be constructed and adapted for single, disposable use.

Figure 2A:
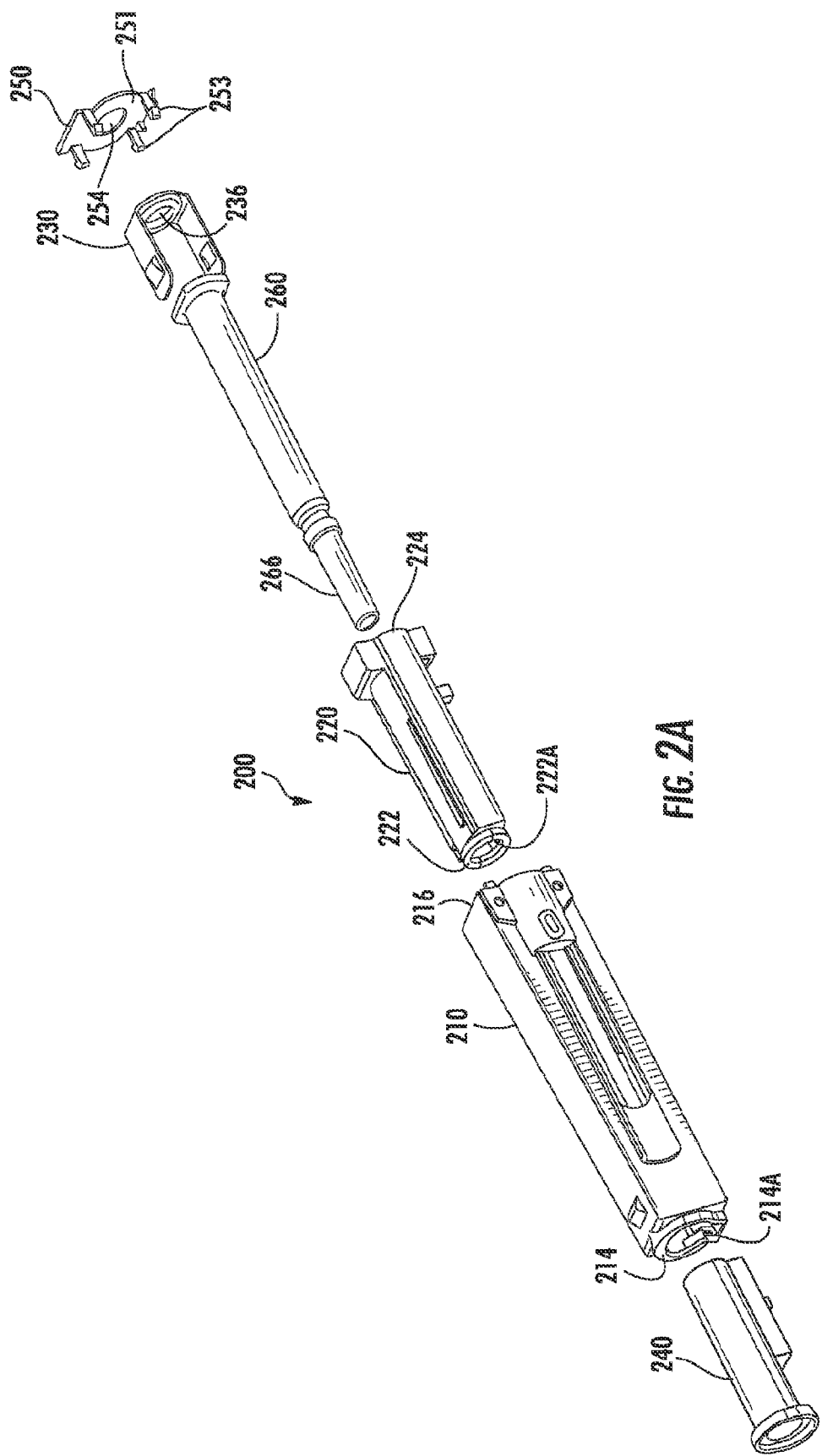
FIG. 2A is an exploded perspective view of an exemplary embodiment of the cassette 200 comprising an outer housing 210; an inner sleeve 220; a syringe 260; a lock cap 230; a cover 250 and a shield remover 240.

FIG. 2A illustrates an exploded perspective view of an exemplary embodiment of the cassette 200, according to the present disclosure. The cassette 200 may comprise an outer housing 210, an inner sleeve 220 slidably moveable within the outer housing 210, a syringe 260 disposed within or held by the inner sleeve 220, and a shield remover 240 for removing a protective needle shield 266 of the syringe 260. The outer housing 210 may comprise a proximal end wall 214 and an open distal end 216. The proximal end wall 214 of the outer housing 210 may include an aperture 214A having a size and shape for receiving therethrough the shield remover 240. The inner sleeve 220 may comprise a proximal end wall 222 and an open distal end 224. The proximal end wall 222 of the inner sleeve 220 may include an aperture 222A having a size and shape for receiving therethrough the protective needle shield 266 of the syringe 260. The cassette 200 may further comprise a lock cap 230 for closing the open distal end 224 of the inner sleeve 220 and locking the syringe 260 within the inner sleeve 220. The cassette 200 may further comprise a cover 250 for closing the open distal end 216 of the outer housing 210. The cover 250 provides for tamper resistance by encasing the inner sleeve 220 and the syringe 260 containing a pharmaceutical product 267, within the outer housing 210 of the cassette 200, and also completes the cosmetic appearance of the cassette 200.

Figure 2B:
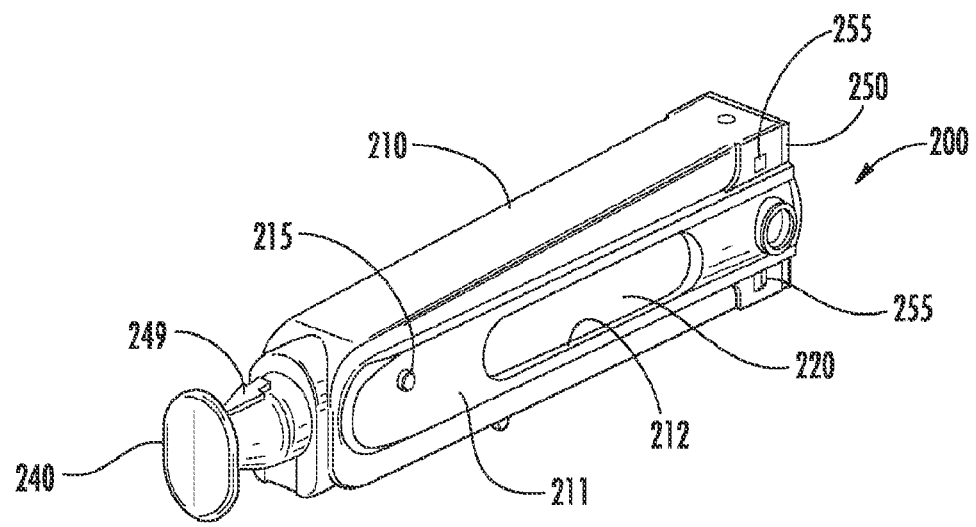
FIG. 2B is a top down front perspective view of the cassette 200 illustrating a side wall 211 of the outer housing 210; a window 212 of the outer housing 210; a pin 215 of the outer housing 210; and the shield remover 240.
Figure 2C:
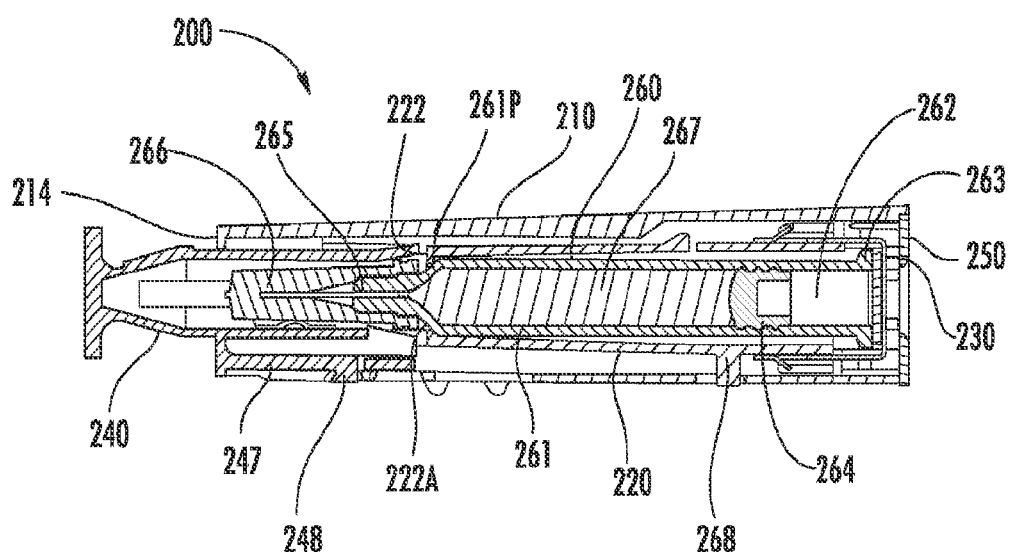
FIG. 2C is a sectional side view of the cassette 200 illustrating the syringe 260 which may comprise a barrel 261, a fluid chamber 262, a predetermined dose of a pharmaceutical product 267, an injection needle 265, an outwardly extending flange 263, a non-rigid protective needle shield 266, and a moveable plunger-stopper 264; and illustrating the shield remover 240 which may comprise a cantilever spring member 247 and a projection or tab 248.

FIG. 2B illustrates a top down front perspective view of the cassette 200. The outer housing 210 of the cassette 200 may comprise an elongated opening or window 212 in each side wall 211 thereof. The windows 212 may be disposed opposite to and aligned with one another. Further, the inner sleeve 220 of the cassette 200 may be made from a transparent, rigid material, such as a clear polycarbonate. The windows 212 in the side walls 211 of the outer housing 210 in combination with the transparent inner sleeve 220, allow viewing of the syringe 260 housed within the inner sleeve 220 (FIG. 2C). The wall portions of the inner sleeve 220 viewable through the windows 212 of the outer housing 210 may comprise fill volume indicia (not shown). The outer housing 210 of the cassette 200 may also include a pin 215 or any other suitable mechanical structure that prevents the cassette 200 from being inserted into the cassette door 308 in the wrong direction and/or orientation. An "arrow" icon may be provided on the shield remover 240 or the outer housing 210 (not shown) to indicate the proper direction and orientation of cassette insertion into the cassette door 308.

FIG. 2C illustrates a sectional side view of the cassette 200. As can be seen, the inner sleeve 220 may comprise an inner sleeve pin 268, which may be engaged by an insertion drive 330 of the autoinjector 300 (FIG. 8) during the operation thereof. When driven by the insertion drive 330, the pin 268 moves the inner sleeve 220 within the outer housing 210 of the cassette 200. The inner sleeve 220 may be sized and shaped to receive the syringe 260 therein.

Referring still to FIG. 2C, the syringe 260 may comprise a barrel 261 that defines a fluid chamber 262. The fluid chamber 262 may be prefilled with a predetermined dose of a pharmaceutical product 267. The pharmaceutical product 267 may have a viscosity that depends on the temperature of the product 267. The syringe 260 may further comprise an injection needle 265 removably or fixedly disposed at a proximal end of the barrel 261, and an outwardly extending flange 263 disposed at a distal end of the barrel 261. The injection needle 265 may communicate with the fluid chamber 262 to allow dispensing of the predetermined dose of a pharmaceutical product 267 expelled from the fluid chamber 262 of the syringe barrel 261. The syringe 260 may further comprise a moveable plunger-stopper 264, disposed within the fluid chamber 262 of the barrel 260, for expelling the predetermined dose of the pharmaceutical product 267 from the chamber 261 so that it may be dispensed through the injection needle 265. The protective needle shield 266 mentioned earlier, covers the injection needle 265 and may be made of a non-rigid material. In one exemplary embodiment, the syringe 260 may comprise a standard 1-mL long glass syringe. The lock cap 230 closes the distal end 224 of the inner sleeve 220 and fixedly secures a proximal end 261P of the syringe barrel 261 against an inner edge surface formed at the junction of the interior surface of the proximal end wall 222 and the aperture 222A of the inner sleeve 220, so that the syringe 260 moves with the inner sleeve 220 as it travels within the outer housing 210, during the operation of the autoinjector 300.

Figure 3A:
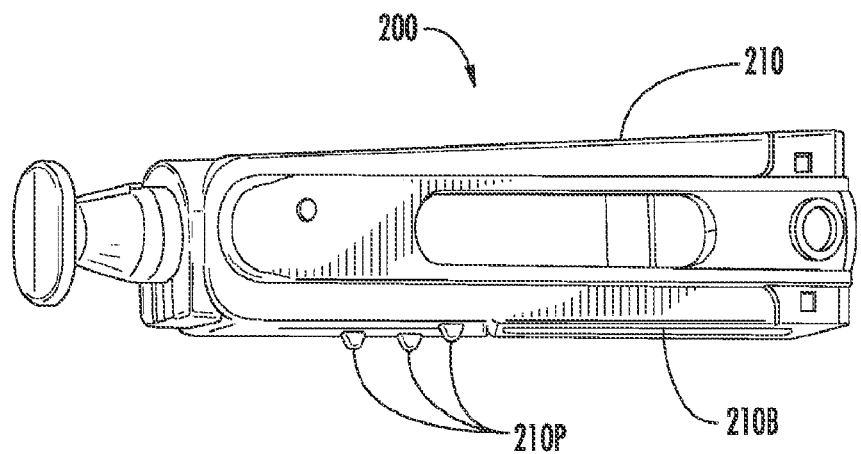
FIG. 3A is a bottom up, front perspective view of the cassette 200 illustrating the cassette outer housing 210 which may comprise a bottom surface 210B with projections 210P.
Figure 3B:
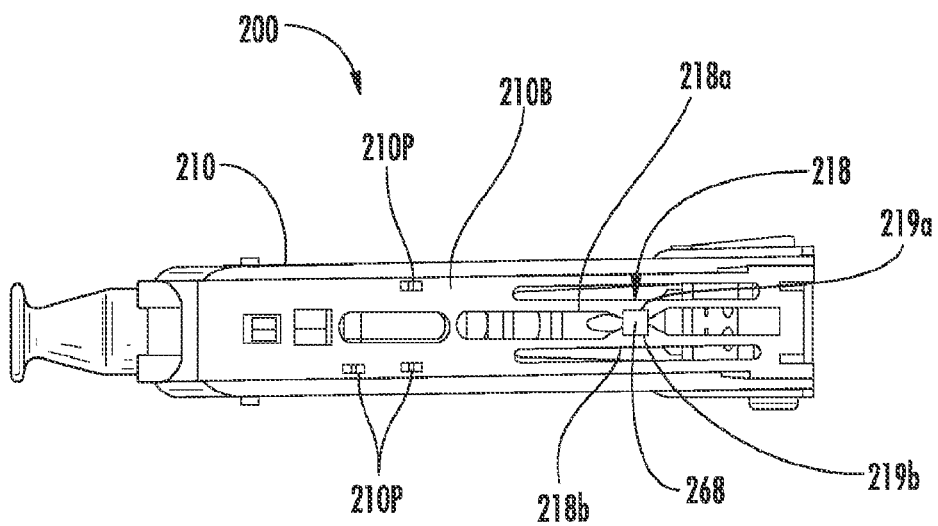
FIG. 3B is a bottom view of the cassette of FIG. 3A illustrating the cassette outer housing 210; the projections 210P; the bottom surface 210B; a latch mechanism 218 which may comprise a pair of parallel extending, resilient locking arms 218a, 218b, and locking detent slots 219a and 219b; and an inner sleeve pin 268.

Referring to FIGS. 3A and 3B, the outer housing 210 of the cassette 200 may comprise a cassette identification arrangement which provides information that identifies the cassette 200, e.g., information about the contents of the syringe 260 contained within the cassette 200 and/or other cassette/syringe characteristics. In one exemplary embodiment, the cassette identification arrangement may comprise one or more bumps or projections 210P provided on a bottom surface 210B of the outer housing 210 of the cassette 200. As illustrated in FIGS. 4G and 4H, the projection(s) 210P may be sensed by or engage a detector 370 in the autoinjector 300 when the cassette 200 is inserted into the door 308 of the autoinjector 300 and the door 308 is closed. The detector 370 may be electrically coupled to a microprocessor (e.g. microprocessor 350 illustrated in FIG. 8) contained within the autoinjector 300, which enables the autoinjector 300 to read the cassette identification arrangement to thereby identify the cassette 200. In one exemplary embodiment, a predetermined number of projections 210P may be located on the bottom surface 210B of the outer housing 210 in predetermined locations, and the detector 370 may comprise a key pad of plural keys (not shown). Certain ones of the plural keys may be actuated by the cassette projections 210P when the cassette 200 is installed in the autoinjector 300, depending upon the location and number of the projections 210P. Each key actuated by one of the projections 210P may provide information that allows the autoinjector 300 to identify the cassette 200. In some embodiments, the cassette identification arrangement identifies the drug delivery profile of the pharmaceutical product provided in the cassette 200. Therefore, upon insertion and recognition of a valid cassette and the information provided by cassette identification arrangement, available preset drug extrusion speed ranges commensurate with the drug delivery profile of the pharmaceutical product provided in the cassette 200 may be automatically registered by the autoinjector 300. Available speed ranges are dependent upon the syringe fill volume and pharmaceutical product characteristics, such as viscosity. For example, but not limitation, if the cassette identification arrangement comprises plural projections 210P, one projection may indicate a 1 mL fill and two projections may indicate a 0.5 mL fill and additional projections may be provided to identify the pharmaceutical product and/or characteristics.

FIG. 3B also illustrates a latch mechanism 218 that may be provided on the bottom wall 210B of the outer housing 210 of the cassette 200. The latch mechanism 218 may include a pair of parallel extending, resilient locking arms 218a, 218b. The locking arms 218a and 218b may each define a locking detent slot 219a and 219b, respectively. The pin 268 of the inner sleeve 220 may engage the detent slots 219a, 219b of the latch mechanism 218 when the syringe 260 is in a home position with the injection needle 265 of the syringe 260 concealed in the cassette 260 in a needle concealed position, thereby locking of latching the inner sleeve 220 into place within the outer housing 210 of the cassette 200. During an injection cycle, the insertion drive 330 of the autoinjector 300 (FIG. 8) may spread the resilient locking arms 218a, 218b apart to unlatch or release the inner sleeve pin 268 from the detent slots 219a, 219b of the latch mechanism 218, thereby allowing the unlatched inner sleeve 220 containing the syringe 260 to be freely moved by the insertion drive 330, which pushes on the inner sleeve pin 268 to move the inner sleeve 220 relative to the outer housing 210 from the home position, where the injection needle 265 is in the needle concealed position, to an injection position, where the injection needle 265 is in a needle extended position that allows it to penetrate the skin at the injection site. At the end of the injection, cycle, the insertion drive 330 pulls the inner sleeve pin 268 back into the detent slots 219a, 219b, thereby returning the inner sleeve 220 (which contains the syringe 260) to the home position, where the injection needle 265 is in the needle concealed position.

Cassettes of similar structure and operation are described in greater detail in the following patent applications, each of which is incorporated herein by reference in its entirety: US Publ. Nos. 2009/0292246 and 20100022955; and PCT Publ. No. WO 2009/143255.

The shield remover 240, illustrated in detail in FIGS. 4A-4F, grips the protective needle shield 266 covering the injection needle 265 of the syringe 260 (FIG. 2C) thereby allowing the shield remover 240 to be used for removing the needle shield 266. Further, the shield remover 240 engages the cassette 200 in a locking manner so that it can not be easily withdrawn from the cassette 200 unless the cassette 200 is properly installed in the autoinjector 300. This feature prevents the needle shield 266 from being inadvertently removed from the syringe 260 when, for example, the cassette is handled by the user. In addition, the presence of the shield remover 240 provides an indication that the cassette 200 has not been previously used or tampered with.

Figure 4A:
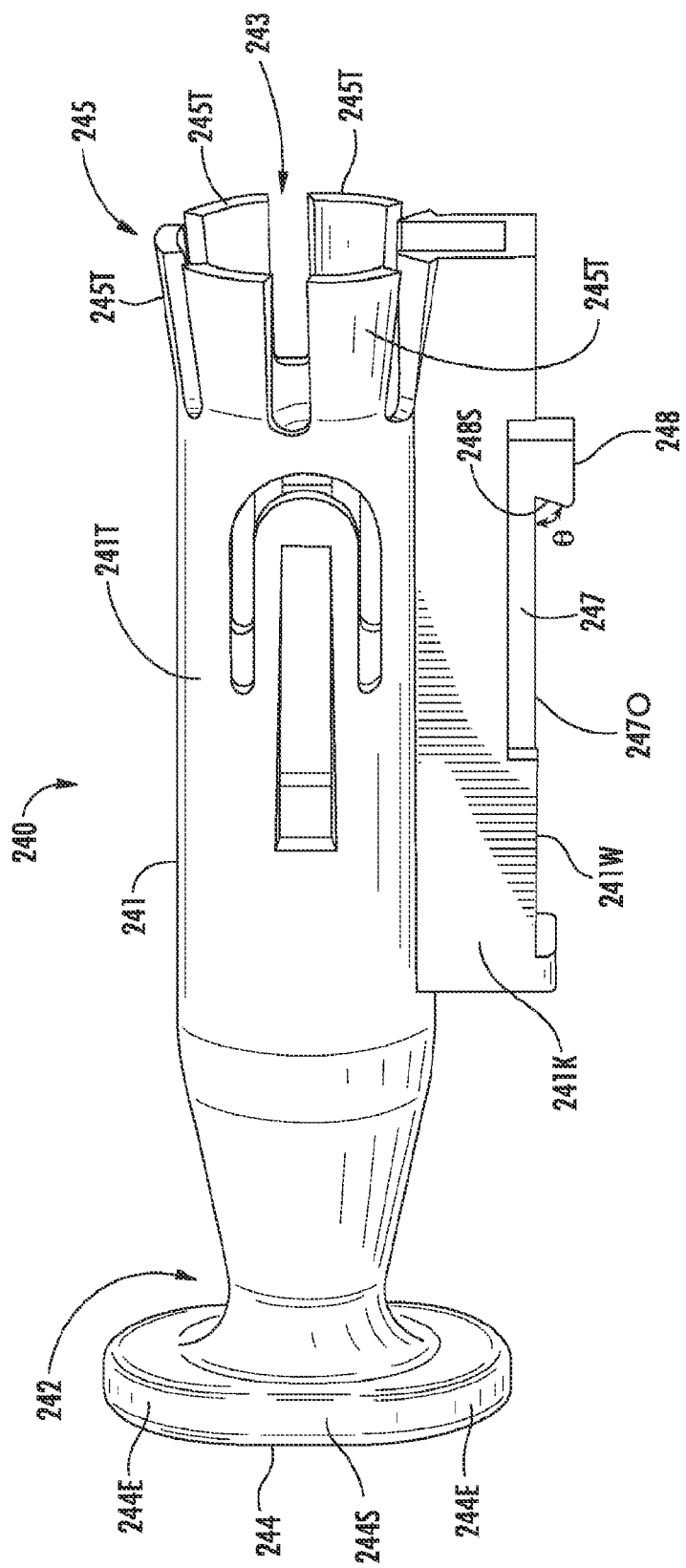
FIG. 4A is a rear perspective view of an exemplary embodiment of the shield remover 240 illustrating the cantilever spring member 247 and the projection or tab 248, wherein the shield remover 240 may comprise a hollow body 241; a closed end 242; an open end 243; a generally cylindrical portion 241T of the body 241; a generally rectangular key portion 241K of the body 241; an expandable partial collar structure 245 having a plurality of flexible, outwardly flared tongues 245T; an outwardly extending flange or gripping member 244 having parallel sides 244S and opposing ends 244E; a bottom wall 241W of the key portion 241K; and an inclined locking surface 248S of the projection or tab 248.

As illustrated in FIG. 4A, the shield remover 240 in one exemplary embodiment may comprise a hollow body 241 having a closed end 242 and an open end 243. The hollow body 241 may comprise a generally cylindrical portion 241T and a generally rectangular, key-like portion 241K extending outwardly from one side of the cylindrical portion 241T. The open end 243 of the cylindrical body portion 241T may define an expandable partial collar structure 245 formed, for example, by a plurality of flexible, outwardly flared tongues 245T. The cylindrical portion 241T of the body 241 may taper down toward the closed end 242 thereof. An outwardly extending flange that functions as a gripping member 244 may be defined at the closed end 242 of the cylindrical body portion 241T. The gripping member 244 may comprise flat, parallel sides 244S connecting rounded opposing ends 244E. The gripping member 244 allows users with manual dexterity issues to easily remove the needle shield 266 from the syringe 260, after the cassette 200 is properly installed in the autoinjector 300.

Figure 4B:
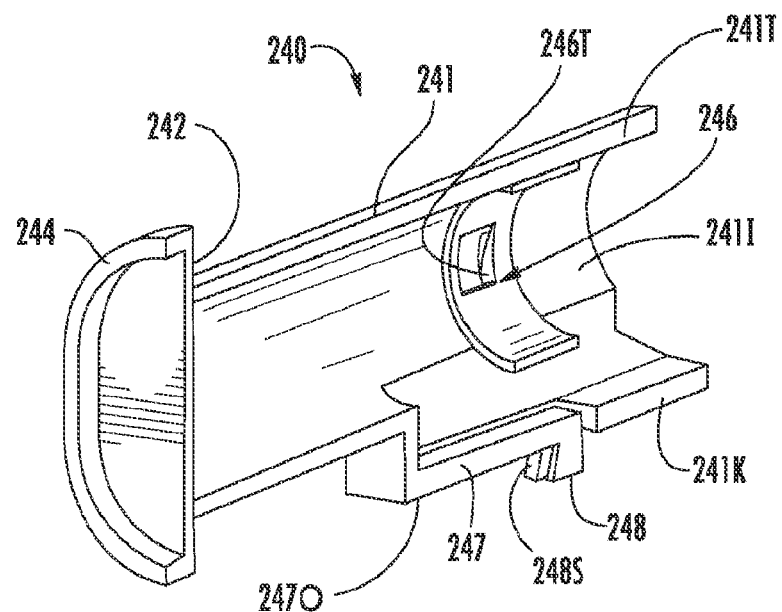
FIG. 4B is a sectional front perspective view of another exemplary embodiment of the shield remover 240 illustrating the gripping member 244; the closed end 242 of the body 241; the cantilever spring member 247; the projection or tab 248; the inclined locking surface 248S of the projection or tab 248; and the key portion 241K of the body 241, wherein the shield remover 240 may comprise a metal tubular insert 246 having needle shield gripping teeth 246T; and an interior surface 241I of the cylindrical body portion 241T.

As illustrated in FIG. 4B, the shield remover 240 in some embodiments may comprise a metal tubular insert 246 frictionally engaged with an interior surface 241I of the cylindrical body portion 241T of the body 241. The metal insert 246 may have a slit along its length (not visible) and may comprise two or more spaced-apart needle shield gripping teeth 246T projecting inwardly into the interior of the cylindrical body portion 241T and generally toward the closed end 242 thereof. In another exemplary embodiment, as shown in FIG. 4C, needle shield gripping teeth 246T' may be formed on the interior surface 241I of the cylindrical body portion 241T.

Figure 4C:
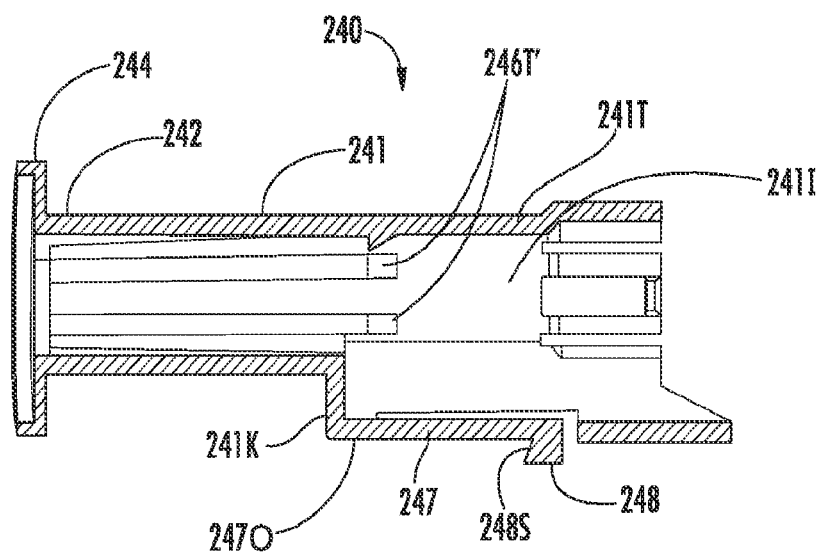
FIG. 4C is a sectional side view of another exemplary embodiment of the shield remover 240 illustrating the gripping member 244; the closed end 242 of the body 241; the cantilever spring member 247; the projection or tab 248; the inclined locking surface 248S of the projection or tab 248; the key portion 241K of the body 241; and the interior surface 241I of the cylindrical body portion 241T, wherein the shield remover 240 alternatively comprises needle shield gripping teeth 246T'.
Figure 4D:
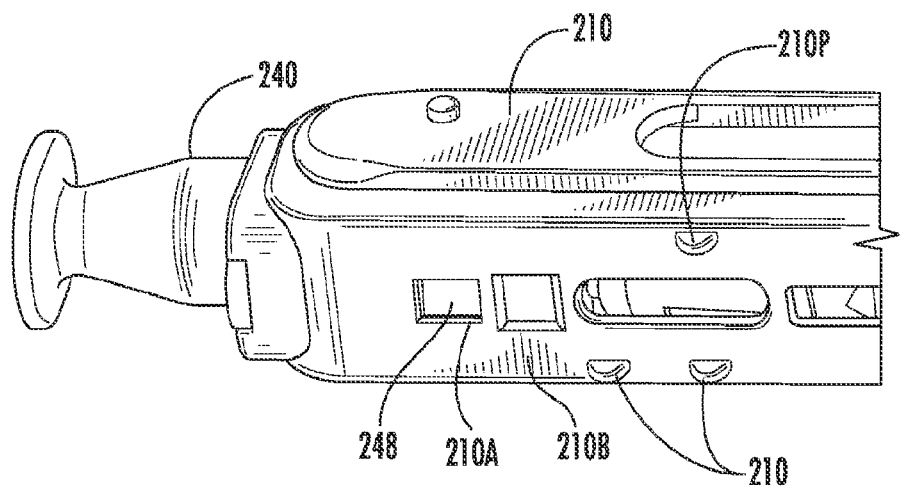
FIG. 4D is a bottom up rear perspective view of a portion of the cassette 200 of FIG. 2B illustrating the shield remover 240; the cassette outer housing 210; the projections 210P; the outer housing bottom surface 210B; the outer housing aperture 210A; and the shield remover projection or tab 248.

As illustrated in FIGS. 4A-4C, the key-like body portion 241K of the shield remover 240 prevents rotation of the shield remover 240 within the proximal end wall 214 of the outer housing 210 of the cassette 200. The key-like body portion 241K may comprise a bottom wall 241W that includes a locking structure formed by a cantilever spring member 247 and a downwardly extending projection or lock tab 248 provided at the free end of the spring member 247. The lock tab 248 may comprise an undercut formed by an inclined surface 248S that faces the closed end 242 of the cylindrical body portion 241T and defines an acute angle 0 with the outer surface 247O of the cantilever member 247.

Figure 4E:
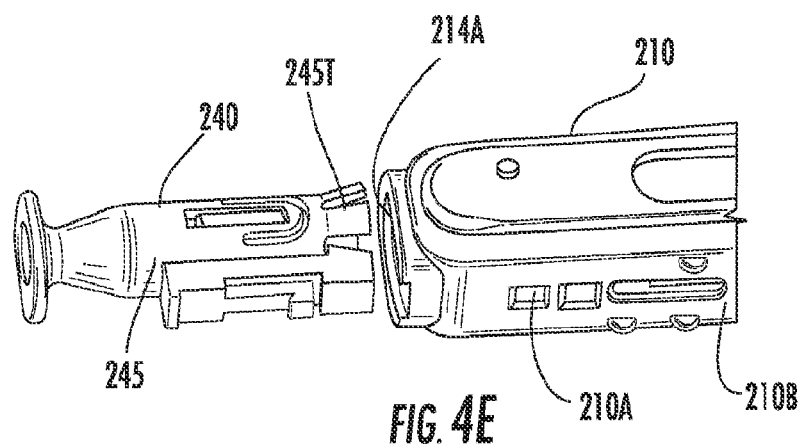
FIG. 4E is a bottom up front perspective view of a portion of the cassette 200 with the shield remover 240 removed from the cassette 200, illustrating the expandable partial collar structure 245 of the shield remover 240; aperture 214A of the cassette outer housing 210, the outer housing bottom wall 210B; and aperture 210A of the outer housing 210.
Figure 4F:
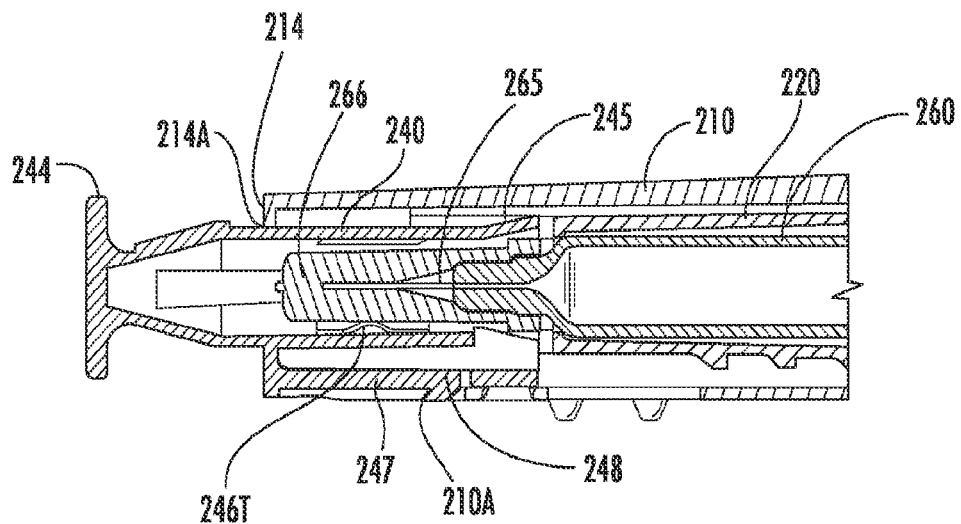
FIG. 4F is a sectional side view of a portion of the cassette 200 illustrating the inner sleeve 220; the outer housing 210; the outer housing end wall 214; the outer housing aperture 214A; the shield remover 240; the injection needle 265; the needle shield 266; the cantilever spring member 247; the projection or tab 248; the outer housing aperture 210A.
Figure 4G:
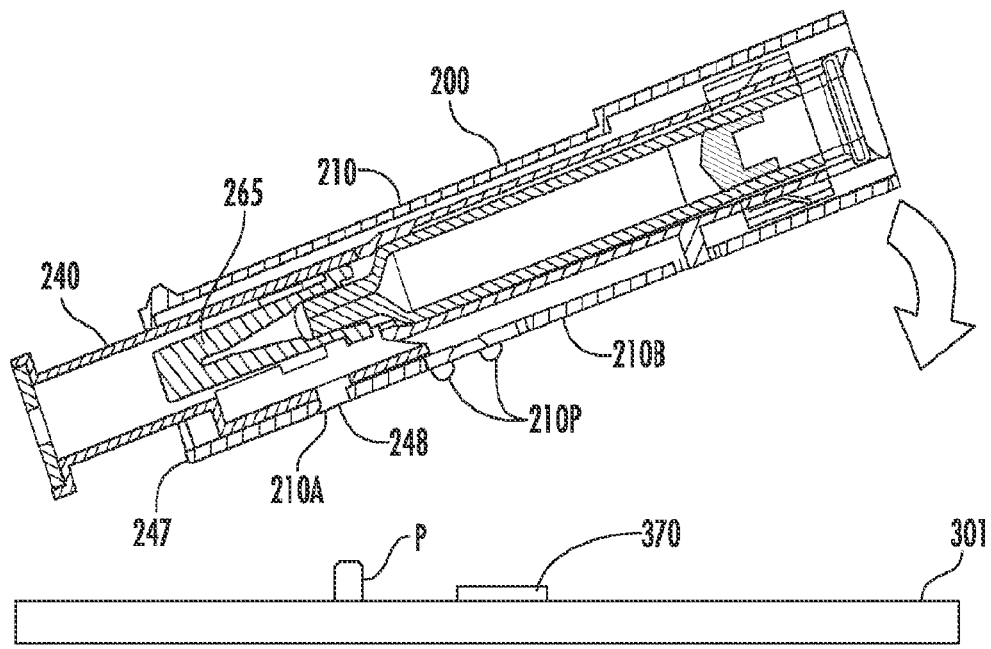
FIG. 4G is a sectional side view of the cassette 200 installed in the autoinjector 300 illustrating the shield remover 240; the tab 248 of the shield remover 240; the needle shield 265; the outer cassette housing 210; the outer housing bottom wall 210B; the aperture 210A of the outer cassette housing 210; a chassis 301 of the autoinjector 300 and a pin P provided by the chassis 301.
Figure 4H:
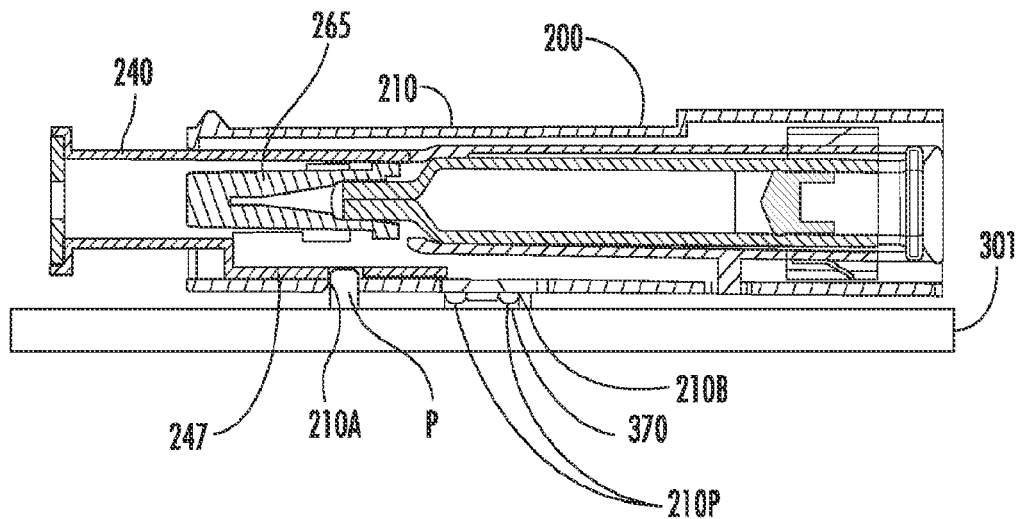
FIG. 4H is a sectional side view of the cassette 200 installed in the autoinjector 300 illustrating the shield remover 240; the needle shield 265; the outer cassette housing 210; the outer housing bottom wall 210B; and the aperture 210A of the outer cassette housing 210; the projections 210P; the detector 370; the chassis 301 of the autoinjector; and the pin P.

FIG. 4F illustrates a sectional side view of a proximal portion of the cassette 200. As illustrated, the needle cover 266 of the syringe 260 may be disposed within the cylindrical body portion 241T (FIG. 4A) of the shield remover 240 such that the needle gripping teeth 246T (or teeth 246T' illustrate in FIG. 4C) of the shield remover 240 grip the outer surface of the needle cover 266. The body 241 of the shield remover 240 may extend through the aperture 214A formed in the proximal end wall 214 of the outer housing 210 of the cassette 200, which locates the gripping member 244 of the shield remover 240 outside of the cassette 200. The locking structure of the shield remover 240, formed by the cantilever spring member 247 and lock tab, may be disposed within the marginal proximal portion of the outer cassette housing 210, such that it locks the shield remover 240 in place in the cassette 200, in a tamper-resistant manner. Locking may be facilitated by the cantilever spring member 247, which forces or biases the tab 248 into a lock aperture 210A (best illustrated in FIGS. 4D and 4E) that may be defined in the bottom surface 210B of the outer housing 210 of the cassette 200. The lock tab 248 engaged with the lock aperture 210A of the cassette outer housing 210, substantially prevents withdrawal of the shield remover 240 from the cassette 200, unless the cassette 200 is properly installed within the autoinjector 300. Because the shield remover 240 is attached to the needle shield 266 and locked within the cassette 200, the needle shield 266 may not be inadvertently removed from the syringe 260, prior to proper installation in the autoinjector 300. The presence of the shield remover 240 also provides an indication that the cassette 200 has not been previously used or tampered with.

FIG. 4G is a sectional side view illustrating the cassette 200 installed in the access door of the autoinjector (both not visible) prior to closing of the door, and FIG. 4H illustrates a sectional side view of the cassette 200 after the access door of the autoinjector (both not visible) has been closed. As illustrated in FIGS. 4G and 4H, the autoinjector 300 may include a chassis 301 (also see FIG. 8) for holding the cassette 200 within the autoinjector 300. The chassis 301 may include a pin P, and the cassette identification detector 370 described earlier. As illustrated in FIG. H, closure of the access door positions the cassette 200 in or on the chassis 301 of the autoinjector 300 so that the cassette identification projections 210P can be read by the detector 370, thereby allowing automatic identification of the cassette 200. In addition, the pin P presses the locking structure tab 248 of the shield remover 240 up, thereby overcoming the biasing force provided by the cantilever spring member 247. As the lock tab 248 moves up, it releases from the tab receiving aperture 210A in the bottom wall 210B of the outer cassette housing 210 (FIG. 4F), thereby unlocking the shield remover 240 from the outer housing 210 of the cassette 200. With the locking structure of the shield remover 240 unlocked, a user can now grasp the gripping member 244 of the shield remover 240 and withdraw it from the cassette 200 and the autoinjector 300, thereby removing the needle shield 266 and uncovering the injection needle 265.

FIG. 4E illustrates a bottom up, front perspective view of the proximal portion of the cassette 200 with the shield remover 240 removed from the cassette 200. As can be seen, once the shield remover 240 is removed, the tongues 245T of the expandable partial collar structure 245 expand or spread outwardly to prevent the shield remover 240 and the needle shield 266 attached thereto (not visible) from being re-inserted into the aperture 214A formed in the proximal end wall 214 of the cassette outer housing 210. The absence of the shield remover 240, therefore, provides an indication to the user that the cassette 200 has already been used or has been tampered with.

Figure 5A:
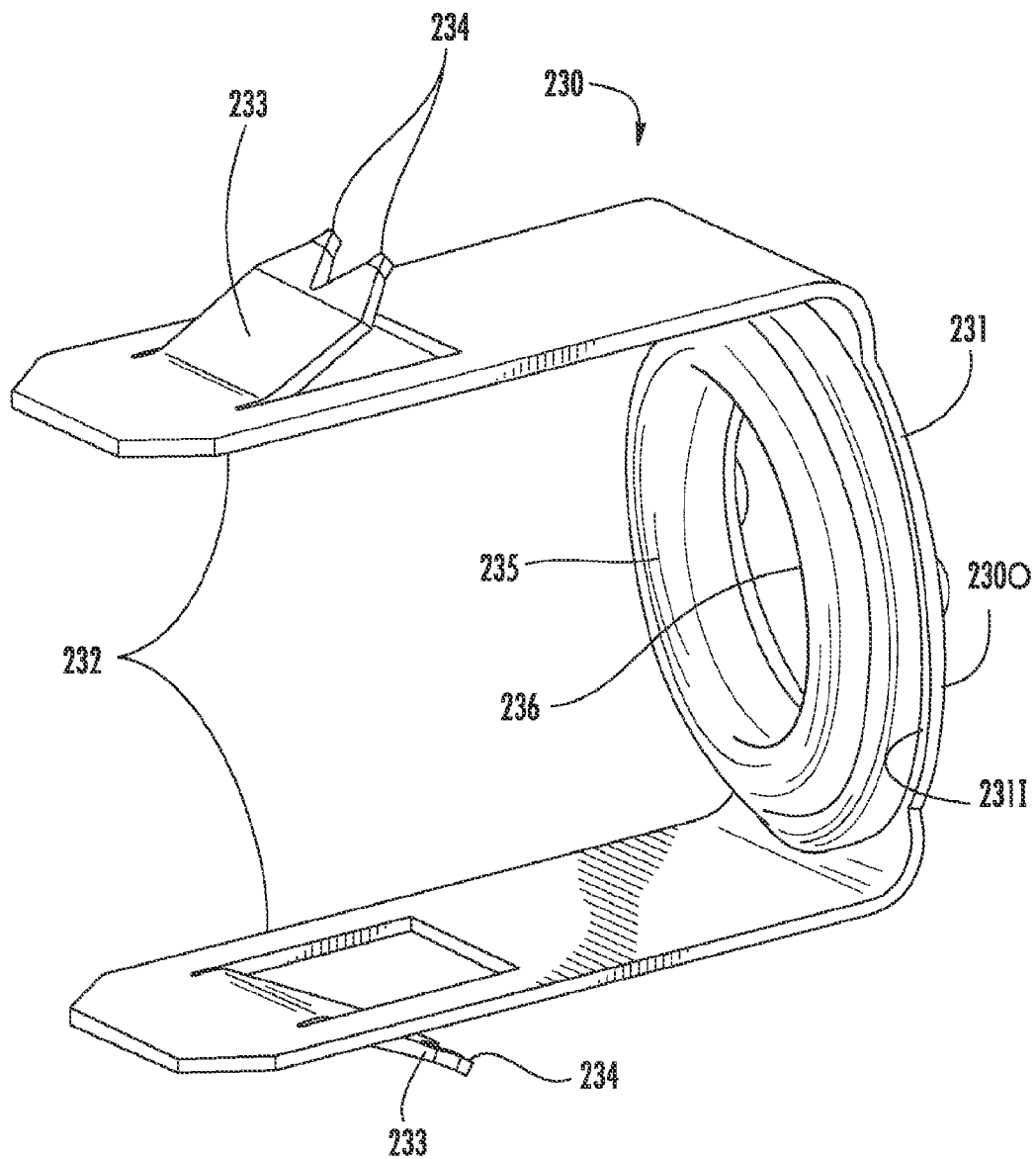
FIG. 5A is a front perspective view of an exemplary embodiment of the lock cap 230 which may comprise an annular body 231; an outer surface 2310; an inner surface 2311, opposing arms 232; cut-out members 233; a barbed ends 234; a soft elastomeric ring-shape bumper 235; and an opening 236.
Figure 5B:
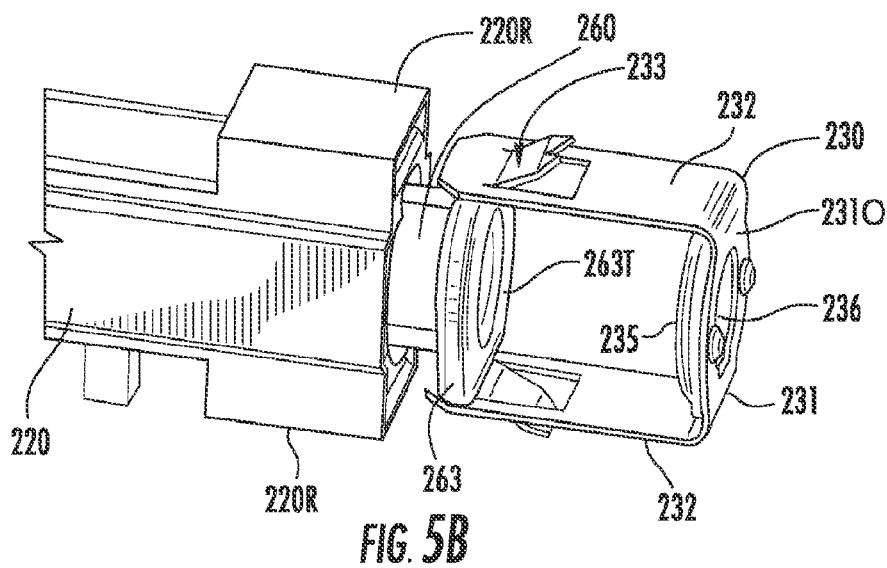
FIG. 5B is a rear perspective view of a portion of an inner sleeve 220 of the cassette 200 illustrating the syringe 260; the inner sleeve 220; the lock cap 230; the lock cap annular body 231; the lock cap outer surface 2310; the lock cap opposing arms 232; the lock cap cut-out members 233; the lock cap soft elastomeric ring-shape bumper 235; the lock cap opening 236; the flange 263 of the prefilled syringe 260 and opposing receiving receptacles 220R of the inner sleeve 220.
Figure 5C:
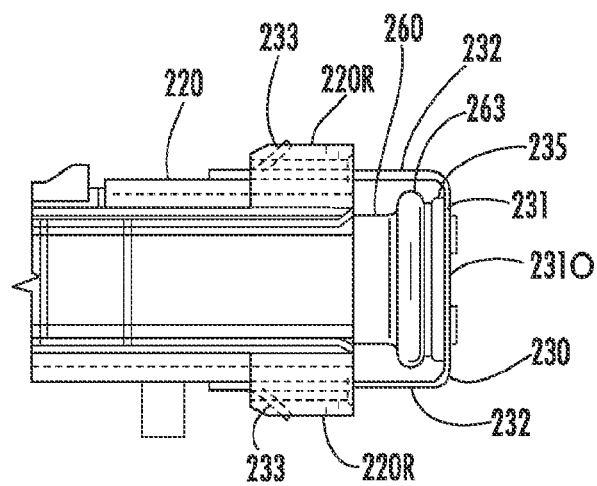
FIG. 5C is a side view of a portion of the inner sleeve with 220 the syringe 260 inserted therein and locked in place with the lock cap 230, and illustrating the lock cap annular body 231; the lock cap outer surface 2310; the lock cap opposing arms 232; the lock cap cut-out members 233; the lock cap soft elastomeric ring-shape bumper 235; the flange 263 of the prefilled syringe 260 and opposing receiving receptacles 220R of the inner sleeve 220.

The lock cap 230, illustrated in FIGS. 5A-5C, locks the syringe 260 in the inner sleeve 220 with a predetermined force which may be set during assembly of the cassette 200. The lock cap 230 may comprise a generally flat, annular body 231 having outer and inner surfaces 2310 and 2311, and opposing arms 232 depending from the body 231, away from the inner surface 2311 thereof. Each of the arms 232 may comprise a cut-out member 233 with a barbed end 234. In some embodiments, the cut-out members 233 may be spring-like. The members 233 may extend outwardly from the arms 232 and toward the body 231. The body 231 can be made from a metal or rigid plastic material. A soft elastomeric ring-shape bumper 235 may be affixed to the inner surface 2311 of the body 231. The body 231 and bumper 235 may define an opening 236 which can be dimensioned to allow a plunger rod 343 actuated by a motorized extrusion drive 340 of the autoinjector 300 (FIG. 11C), to pass through the lock cap 230 and engage and move the plunger-stopper 264 through the fluid chamber 262 of the syringe barrel 261 during the operation of the autoinjector 300. The lock cap 230 may be dimensioned to receive the flange 263 of the syringe 260 between the opposing arms 232 thereof, in a slip-fit manner with the bumper 235 engaging a top surface 263T of the flange 263 as illustrated in FIGS. 5B and 5C. The arms 232 of the lock cap 230 may be inserted into opposing receiving receptacles 220R formed at a distal end of the inner sleeve 220 when the syringe 260 is assembled into the inner sleeve 220. The barbs 234 of the arms 232 grip the inner surfaces of the receiving receptacles 220R to lock the lock cap 230 into position, thereby lockingly holding the syringe 260 in the inner sleeve 220. The arms 232 of the lock cap 230 may be inserted into the receptacles 220R of the inner sleeve 220 a selected distance to limit the amount of force (to a predetermined value) applied to the syringe 260 during assembly into the cassette 200 and during usage.

Figure 5D:
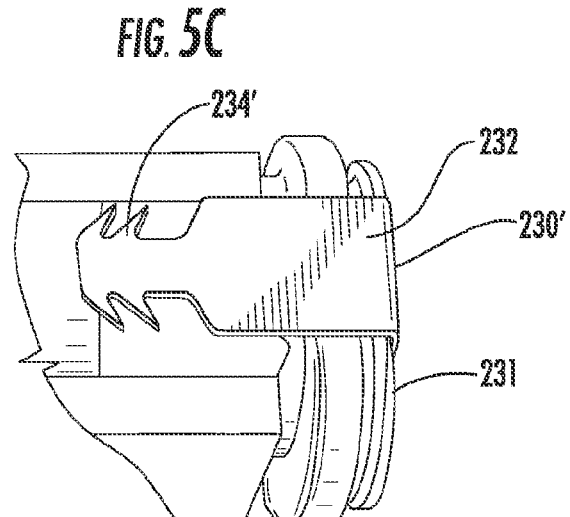
FIG. 5D is a front perspective view of a portion of the inner sleeve 220 and another embodiment of the lock cap numbered 230' comprising an annular body 231; opposing arms 232; and a barb arrangement 234'.

FIG. 5D illustrates an alternate embodiment of the lock cap numbered 230'. The lock cap 230' is similar to the lock cap 230 of FIGS. 5A-5C, but omits the cut-out members 233 and instead, provides a barb arrangement 234' at the end of each arm 262.

Referring again to FIGS. 2A-2C, the cover 250 attaches to a distal end of the outer housing 210 of the cassette 200 to close a distal end of the cassette 200. The cover 250 may be a generally planar member having a shape which matches that of the distal end 216 of the outer housing 210. The cover 250 may comprise two or more locking arms 253 that extend from an inner surface 251 of the cover 250 and lockingly engage corresponding receptacles 255 extending through the side walls 211 of the outer housing 210. In addition, any detent structure or other suitable locking arrangement (not shown) formed in, on, or through the outer housing 210, adjacent to the distal end 216 thereof may be used for attaching the cover 250. The cover 250 may further comprise an opening 254 which axially aligns with the opening 236 defined by the lock cap 230. The opening 254 in the cover 250, like the opening 236 of the lock cap 230, may be dimensioned to allow the plunger rod 342 actuated by the motorized extrusion drive 340 of the autoinjector 300 (FIG. 8), to pass through the cover 250 and engage and move the plunger-stopper 264 through the fluid chamber 262 of the syringe barrel 261 during the operation of the autoinjector 300.

Referring now to FIGS. 6A-6F, the autoinjector 300 may comprise a casing 302 having a handle section 304 and a cassette receiving section 306 inline with the handle section 304. To aid patients with manual dexterity issues, the handle section 304 of the autoinjector casing 302 may define an ergonomically shaped handle 305 with a soft grip area 305S. The cassette receiving section 306 comprises the cassette door 308 (FIGS. 6B and 6D) described earlier. The cassette door receives the cassette 200 in an open position (FIG. 1) and aligns the cassette 200 with insertion and extrusion drives, and other structures and components of the autoinjector 300 in a closed position. The cassette door 308 may include a "cassette" icon that indicates the insertion entry point for the cassette 200. The cassette receiving section 306 of the casing 302 may comprise windows 310A, 310B on opposing sides thereof that align with the windows 212 (FIG. 2B) of the cassette 200 when the cassette door 308 is closed with the cassette 200 correctly installed therein. In one or more embodiments, the windows 310A, 310B may be double-layered. One or more lights (not shown) may be provided inside the casing 302 to evenly backlight illuminate the cassette windows 212 and the syringe 260 disposed within the inner sleeve 220 of the cassette 200, so that the user can observe the injection cycle through the windows 310A, 310B of the autoinjector 300, i.e., observe the initial and end positions of the plunger-stopper 264 of the syringe 260 during the syringe content (hereinafter "drug") extrusion process, as well as syringe movements within the cassette 200.

Referring still to FIGS. 6A, 6B, 6D, and 6F, the autoinjector 300 may further comprise a user interface 312 and an audio speaker (not shown). The user interface 312 (best illustrated in FIG. 6A) may be located in the cassette receiving section 306 of the casing 302, and provides various visual indicators. The audio speaker may be disposed inside the casing 302 and provides various audible indicators. The audio speaker may audibly communicate with the external environment via a speaker aperture 314 formed in the casing 302 in the cassette receiving section 306. The visual and audible indicators generated by the user interface 312 and the audio speaker can tell the user when the autoinjector 300 is ready for use, the progress of the injection process, injection completion, the occurrence of any errors, and other information. The autoinjector 300 may further comprise one or more of a settings/mute switch 315, a speed selector switch 316, a start button 307, and an eject button 317. The settings/mute switch 315 (FIG. 6B) may be located in the cassette receiving section 306 of the casing 302. The mute switch 315 may be constructed and adapted allow the user to turn on and off all synthesized sounds, except error sounds, and to respond in real-time so that if the user begins the injection process and changes the mute switch to off, the sounds are immediately muted. The mute switch 315 may also be constructed and adapted to slide toward a "mute" icon to mute the audio speaker. A light indicator may be provided to confirm the "mute" state. The speed selector switch 316 (FIGS. 6A and 6B) may be located in the cassette receiving section 306 of the casing 302. The speed selector switch 316 may be constructed and adapted to allow the user to select among a plurality of preset drug delivery (extrusion) speeds to accommodate personal patient preference. The speed selector switch 316 may comprise a three switch positions. Other embodiments of the speed selector switch may comprise two switch positions, or 4 or more switch positions. In still other embodiments, the speed selector switch may be of the infinitely variable type. In some embodiments, changing the position of the switch 316 prior to injection changes the speed of drug extrusion during injection while changing the position of the speed selector switch 316 during injection, does not change the speed of the injection in real time. The autoinjector 300 may also be provided with one or more demo cassettes to allow the user to experiment with different speeds of drug delivery. The start button 307 at a free end of the handle 305. The button 307 may include an indentation 307T for optimizing thumb placement on the button 307. The button 307 may be made of a translucent material that allows a lighting effect to illuminate the button as signals. The eject button 317 (FIG. 6D) may be located in the cassette receiving section 306 of the casing 302. The eject button 317 may include an indentation 317I for optimizing finger placement on the button 317. In some embodiments, the eject button 317 may be controlled by the microprocessor (e.g. microprocessor 350 illustrated in FIG. 8) of the autoinjector 300, which may be programmed to eliminate accidental inputs during the injection process.

Referring again to FIG. 6E, the cassette receiving section 306 of the casing 302 and the cassette door 308 may form a proximal end wall 318 of the autoinjector 300. The proximal end wall 318 may be configured as a broad, flat and stable base for easily positioning the autoinjector 300 on a support surface, after removal of the shield remover 240 or when the autoinjector 300 does not contain the cassette 240. The portion of the proximal end wall 318 formed by the cassette door 308 may include an aperture 308A that is sized and shaped to allow the shield remover 240 to be removed from the cassette 200 and withdrawn through the aperture 308A, when the cassette 200 is installed in the autoinjector 300. As soon as the shield remover 240 passes out through the aperture 308A, the tongues 245T of the expandable partial collar structure 245 expand or spread outwardly, thereby preventing the shield remover 240 and the needle shield 266 attached thereto from being re-inserted into the aperture 308A of the cassette door 308. The proximal end wall of the autoinjector 300 may further comprise a target light 320. The target light 320 may be constructed and adapted to turn on when the shield remover 240 is removed from the cassette 200 and withdrawn through the aperture 308A, thereby visually indicating that the shield remover 240 has been removed. Once turned on, the target light aids the user in visualizing and selecting an injection site.

Figure 6E:
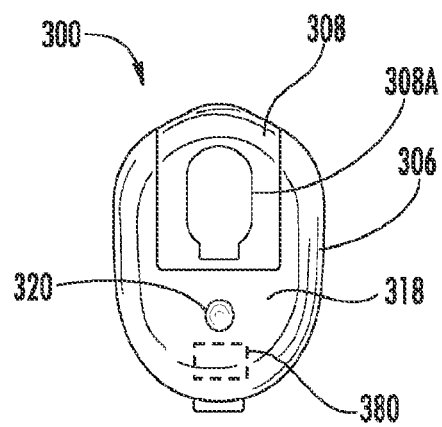
FIG. 6E is an elevational view of a first end of the autoinjector 300 of FIG. 6A illustrating the end wall 318, a target light 320, a cassette door aperture 308A, a skin sensor 380.
Figure 6F:
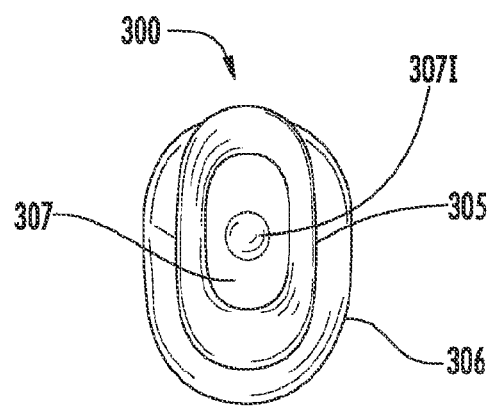
FIG. 6F is an elevational view of a second end of the autoinjector 300 of FIG. 6A illustrating a start button 307.

Referring still to FIG. 6E, the autoinjector 300 may further comprise a capacitance-based skin sensor 380 (shown with broken lines). The skin sensor 380 determines when the proximal end wall 318 of the autoinjector 300 touches or contacts skin without the need to provide downward pressure on the injection-site area. The skin sensor 380 may also be constructed and adapted to inform the user through audible and visual indicators generated by the speaker and user interface, when skin contact is detected. In some embodiments, the skin sensor 380 may comprise two pads or electrodes (not shown) imbedded in the proximal end wall 318 of the autoinjector 300. When an electrode is touched, its capacitance signal increases. If the increase is sufficient as determined by the microprocessor (e.g. microprocessor 350 illustrated in FIG. 8), which is programmed with sensor decision logic, that electrode will become activated. To determine whether skin contact has been made, the microprocessor reads the capacitance of the electrodes. The microprocessor then processes the capacitance information to determine when the electrodes are both making proper contact with the skin.

Figure 7:
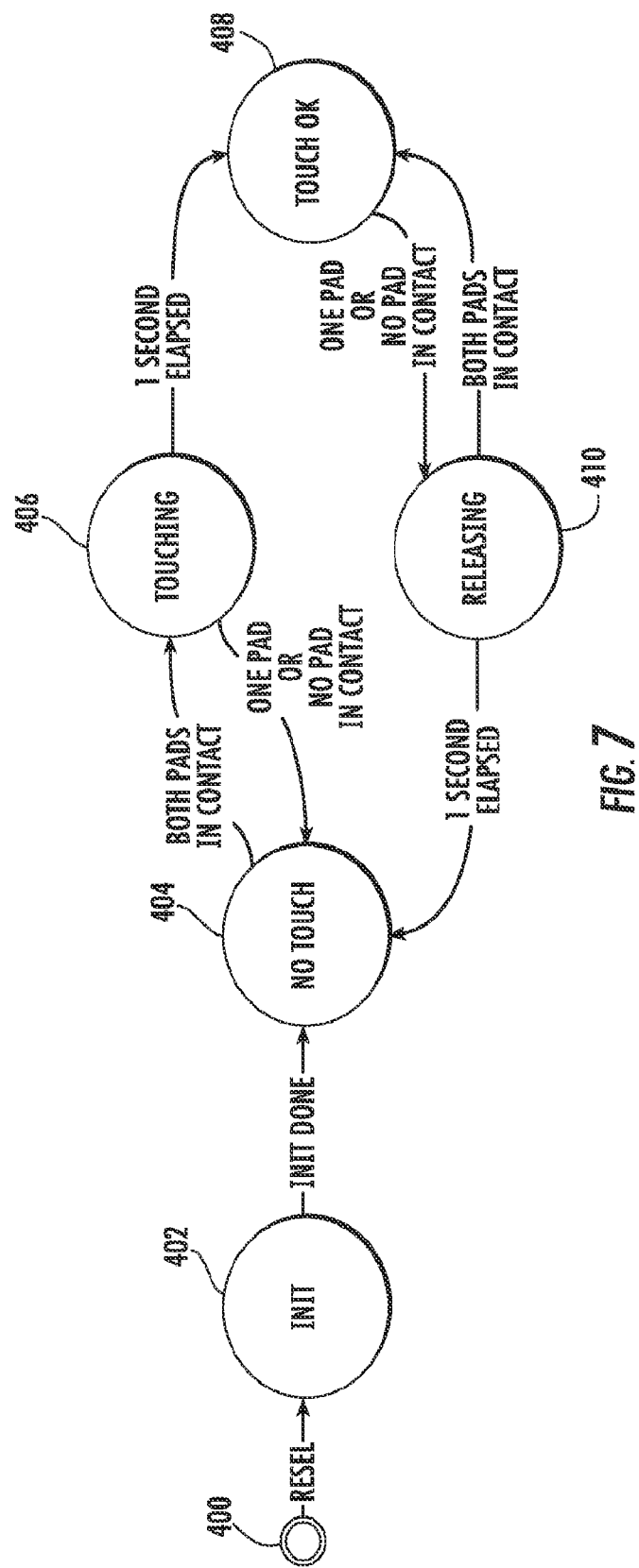
FIG. 7 is a state diagram illustrating the decision logic for controlling skin sensor 380 with the microprocessor 350 of the autoinjector 300, according to an embodiment of the present disclosure.

FIG. 7 is a state diagram illustrating the decision logic for controlling skin sensor 380 with the microprocessor 350 of the autoinjector 300, according to an embodiment of the present disclosure. The process starts at 400 which represents a reset of the autoinjector. The logic then flows to state 402 which represents the initialization of the skin sensor after the reset of the autoinjector. Once initialized, the logic flows to state 404 which represents a "no-touch" state where none or only one of electrodes of the sensor touch skin. If both electrodes touch skin for less than a certain threshold time period (e.g., one second), the logic flows to state 406 which represents a "touching" state. If one or neither one of the electrodes touches skin, the logic flows back to state 404. If, however, both electrodes touch skin for a period of time equal to the threshold time period, the logic flows to state 408 which represents a "touch OK" state. If one electrode or no electrodes contact skin, the logic flows to a "releasing" state 410. If both electrodes touch skin, the logic flows back to "touch OK" state 408. If one or no electrodes contact skin for more than the threshold time period (e.g., more than one second), the logic flows back to "no touch" state 404.

Figure 8:
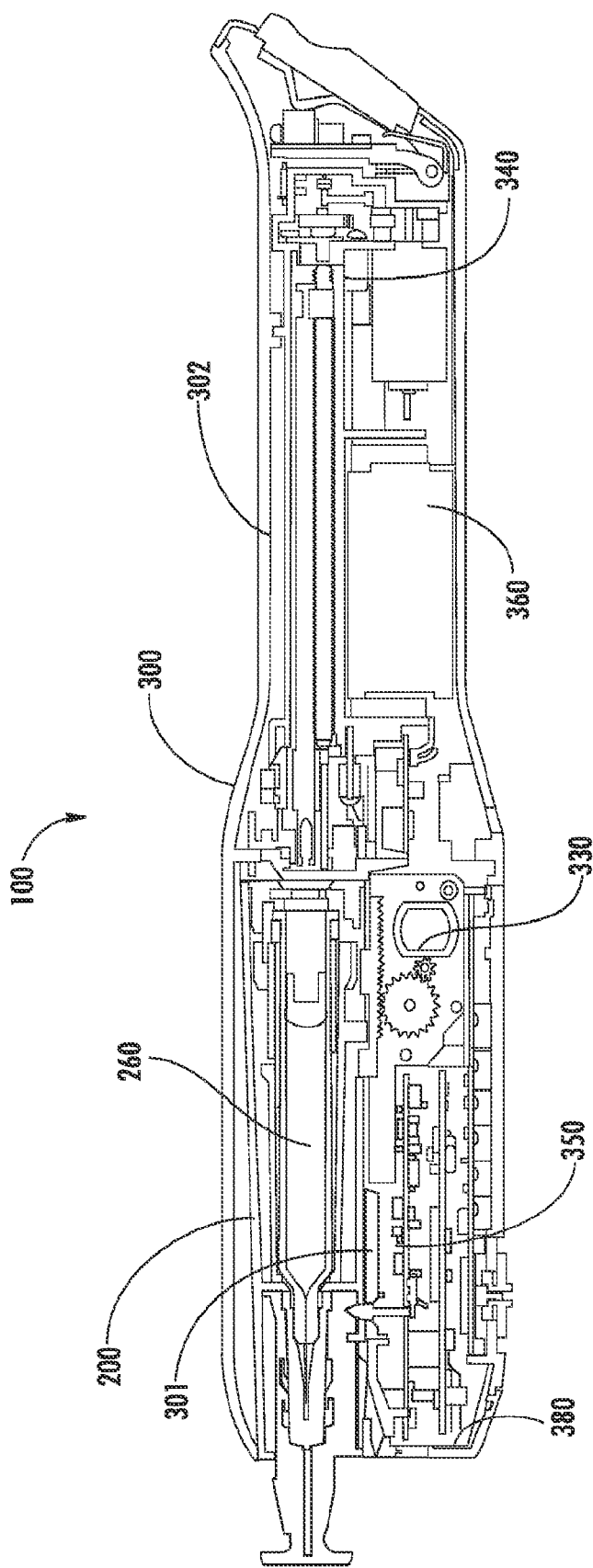
FIG. 8 is a sectional side view of the autoinjector apparatus 100 illustrating the autoinjector 300 and the cassette 200, wherein the autoinjector 300 may comprise the chassis 301, a casing 302, a motorized insertion drive 330, a motorized extrusion drive 340, a microprocessor 350, a battery 360; and wherein the cassette comprises the syringe 260.

FIG. 8 illustrates a sectional side view of the autoinjector apparatus 100. comprising the autoinjector 300 and the cassette 200 installed therein. The casing 302 of the autoinjector 300 may house a chassis 301 for receiving the cassette 200 that contains the syringe 260, a motorized insertion drive 330, a motorized extrusion drive 340, a microprocessor 350 (described earlier), a battery 360 for powering the drives 330, 340 and the microprocessor 350, and the skin sensor 380 (described earlier).

The microprocessor 350 may be programmed with certain instructions that executed by the microprocessor 350 enable it to control and monitor the various operations and functions of the autoinjector 300. For example, but not limitation, the microprocessor may be programmed with instructions for controlling the motorized insertion and extrusion drives 330, 340 such that it controls and monitors each step of the injection cycle and process flow, thereby automating needle insertion, drug extrusion, and needle retraction and ensuring accurate, consistent, and reliable operation of the autoinjector 300 and pharmaceutical product administration. The microprocessor may also be programmed with instructions for controlling the audible and visual feedbacks to the user. An automated power-on self-test checks the operation of the autoinjector 300 and remaining battery charge.

Figure 9A:
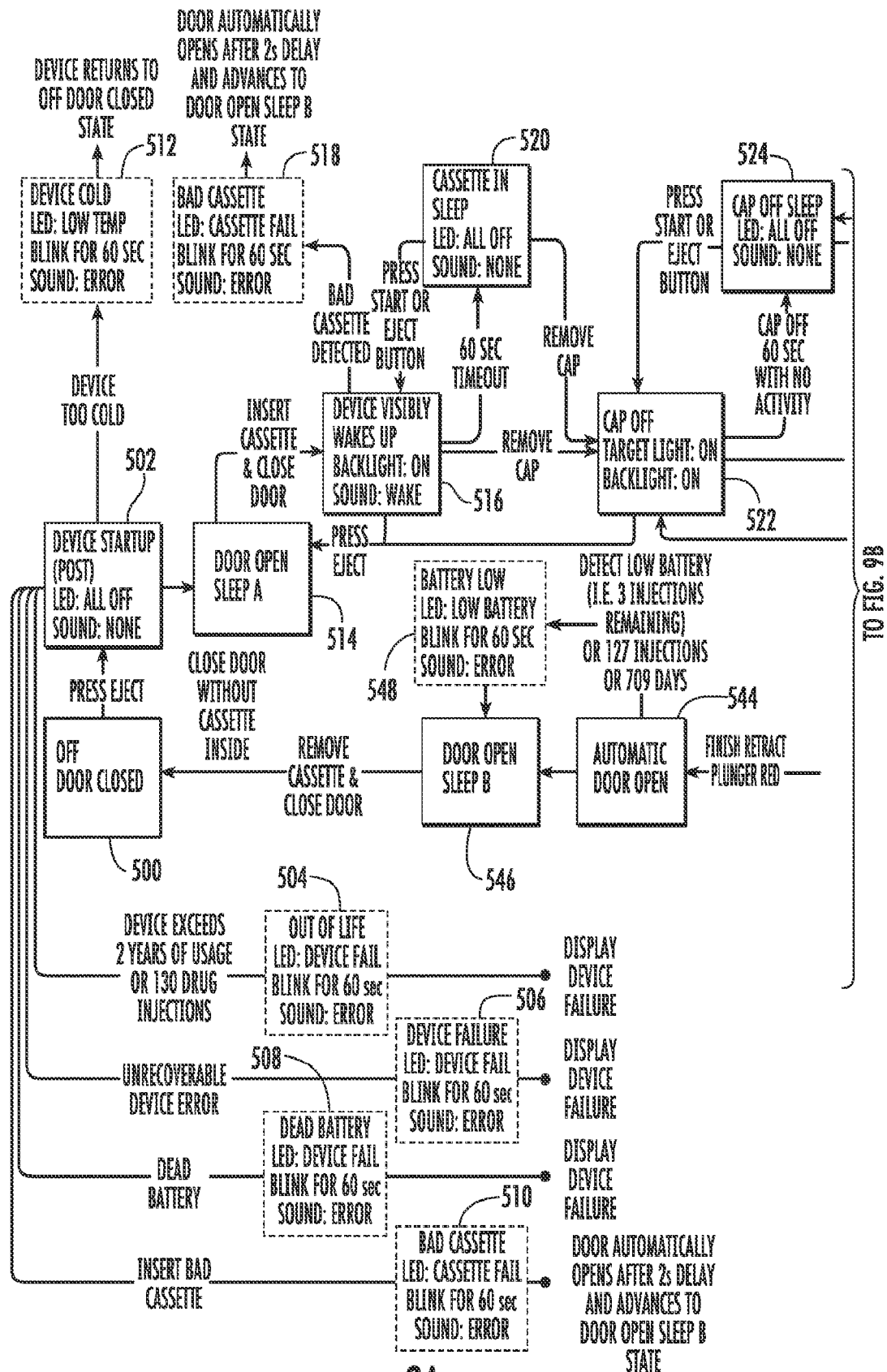
FIG. 9A is a flow chart illustrating the decision logic for controlling the various functions of the autoinjector with the microprocessor, according to an exemplary embodiment of the present disclosure.
Figure 9B:
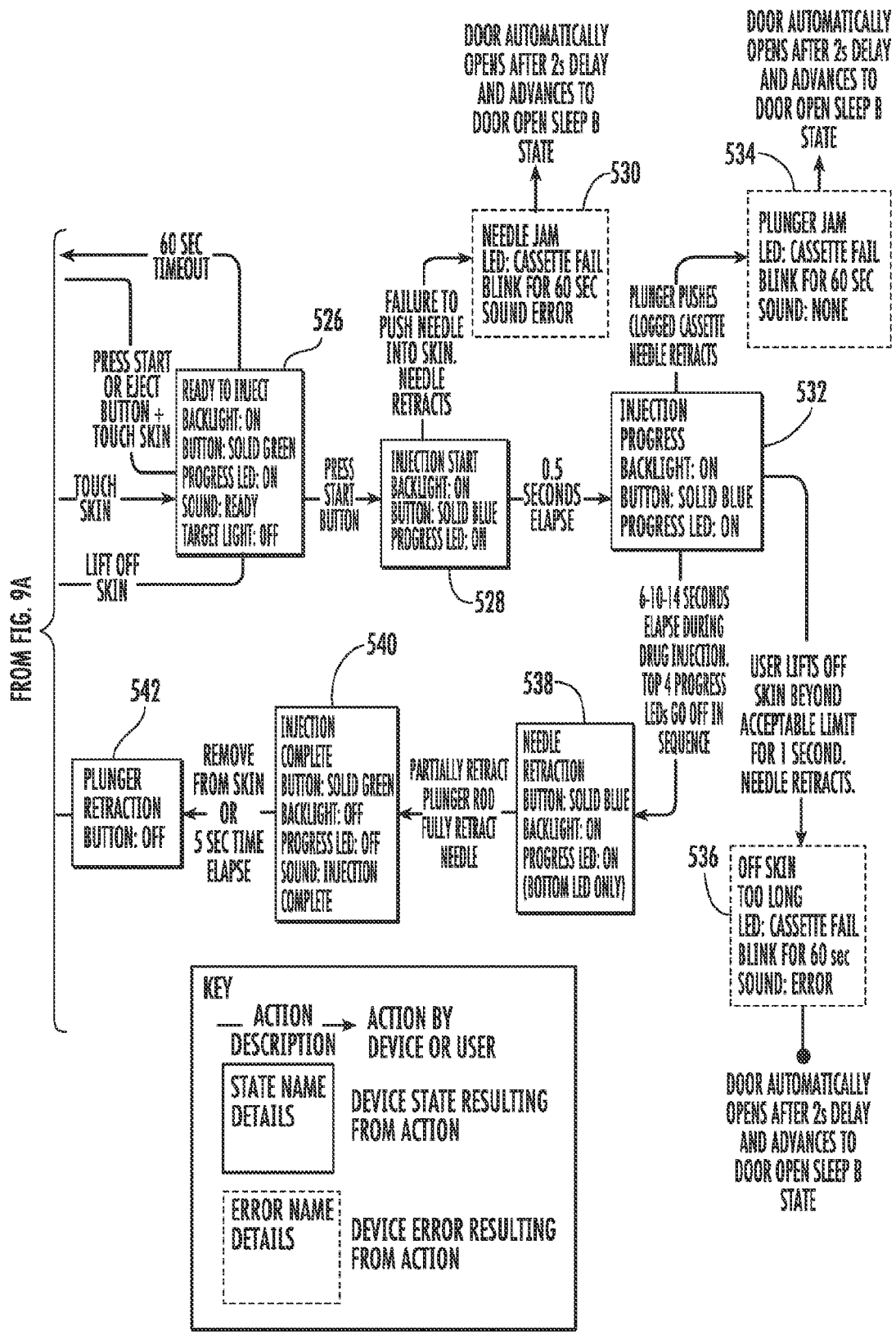
FIG. 9B is a flow chart illustrating the decision logic for controlling the various functions of the autoinjector with the microprocessor, according to an exemplary embodiment of the present disclosure.
Figure 13:
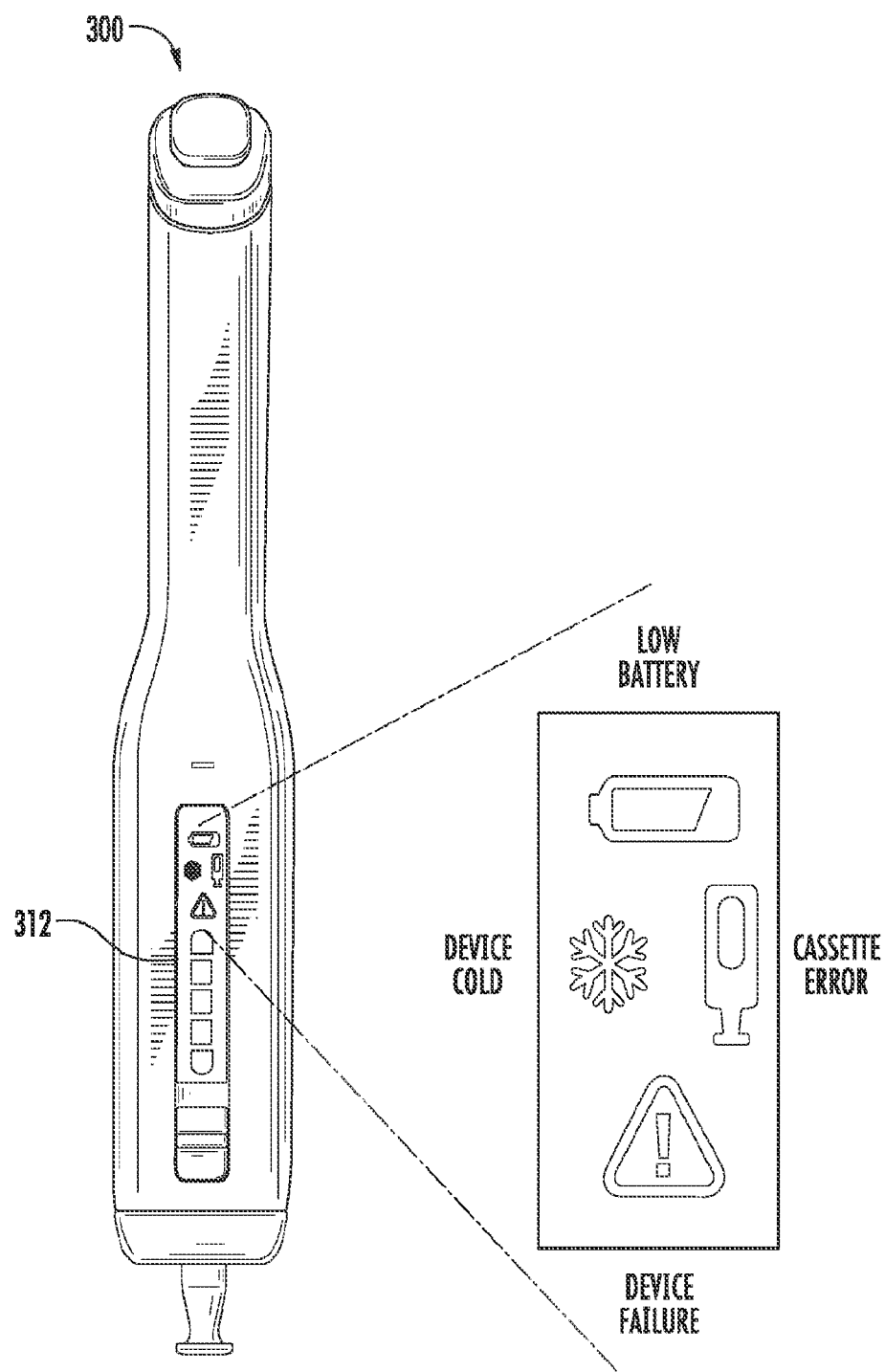
FIG. 13 is a front elevational view of an exemplary embodiment of the autoinjector 300 which illustrates various exemplary icons displayed by the user interface 312.

FIG. 9 is a flow chart illustrating the decision logic for controlling the various functions of the autoinjector 300 with the microprocessor 350, according to an exemplary embodiment of the present disclosure. The microprocessor logic of the autoinjector commences in block 500 with the autoinjector is in an "off, (cassette) door closed" state. If the user presses the eject button, the microprocessor may place the autoinjector in a "device startup" state in block 502 unless the microprocessor determines the following error conditions have occurred: 1) that the autoinjector is "out of life," i.e., autoinjector usage has exceeded a predetermined time period (e.g., two (2) years), or has exceeded a predetermined number of injections (e.g., 130 injections); 2) an unrecoverable device error has occurred; 3) the autoinjector's battery is dead; 4) a defective cassette has been inserted into the autoinjector; or 5) the autoinjector is below a predetermined temperature. If any of the error conditions 1-3 have occurred, visual and audio error messages or alerts corresponding to blocks 504, 506, and 508 may be implemented by the microprocessor, e.g., the user interface may fast blink a "device failure" icon (FIG. 13) for a predetermined time period (e.g., 60 seconds), and the audio speaker may generate a certain sound that indicates a device error. If the error condition 4 has occurred, visual and audio error messages or alerts corresponding to block 510 may be implemented by the microprocessor, e.g., the user interface may blink a "cassette failure" icon (FIG. 13) for a predetermined time period (e.g., 60 seconds) and the audio speaker may generate the device error sound. The microprocessor may then open the cassette door after a predetermined time period (e.g., two (2) seconds) and place the autoinjector into a "door open, sleep B" state in block 546. If the cassette is removed and the cassette door is closed, the microprocessor may place the autoinjector in the "off, door closed" state of block 500. If the error condition 5 has occurred, visual and audio error messages or alerts corresponding to block 512 may be implemented by the microprocessor, e.g., the user interface may blink a "low temp" icon (FIG. 13) for a predetermined time period (e.g., 60 seconds) and the speaker may generate the device error sound. The microprocessor may then place the autoinjector back in the "off, door closed" state of block 500.

Referring still to FIG. 9, if no errors conditions are detected, the microprocessor may place the autoinjector in the "device startup" state in block 502, where it may cause the LEDs of the user interface to remain off and no sound to be generated by the audio speaker. The microprocessor may then open the cassette door, which places the autoinjector into a "door open, sleep state A" in block 514. If a cassette is inserted and the cassette door closed, the microprocessor may cause the autoinjector to enter a "device visibly wakes up" state in block 516, where it turns on the backlight and generates sound with the audio speaker that indicates that the autoinjector is awake. If a bad cassette is detected by the microprocessor, it may generate visual and audible error alerts in block 518, e.g., the user interface may blink a "cassette failure" icon (FIG. 13) for a predetermined time period (e.g., 60 seconds) and the audio speaker may generate the device error sound. The microprocessor may then open the cassette door after a predetermined time period (e.g., two (2) seconds) and place the autoinjector into the "door open, sleep B" state of block 546 so that the cassette can be removed. If the cassette door is subsequently closed, the microprocessor may place the autoinjector into the "off, door close" state of block 500. If the eject button is pressed, the microprocessor may place the autoinjector into the "door open, sleep A" state of block 514. Once the autoinjector is in the "device visibly wakes up" state of block 516, removal of the shield remover of the cassette may cause the microprocessor to place the autoinjector in a "cap off" state of block 522, wherein it turns on the target light and continues to keep the backlight on. If, however, the shield remover is not removed after the autoinjector has entered the "device visibly wakes up" state of block 516 within a predetermined time period (e.g., 60 seconds), the microprocessor may place the autoinjector in a "cassette in, sleep" state in block 520, where it turns off the LEDs and turns off the speaker (no sound). If the start or eject button is then pressed, the microprocessor may place the autoinjector back into the "device visibly wakes up" state of block 516. If, however, the shield remover is removed (after entering the "cassette in, sleep" state of block 520), the microprocessor may place the autoinjector in the "cap off" state of block 522, as previously described.

Figure 12:
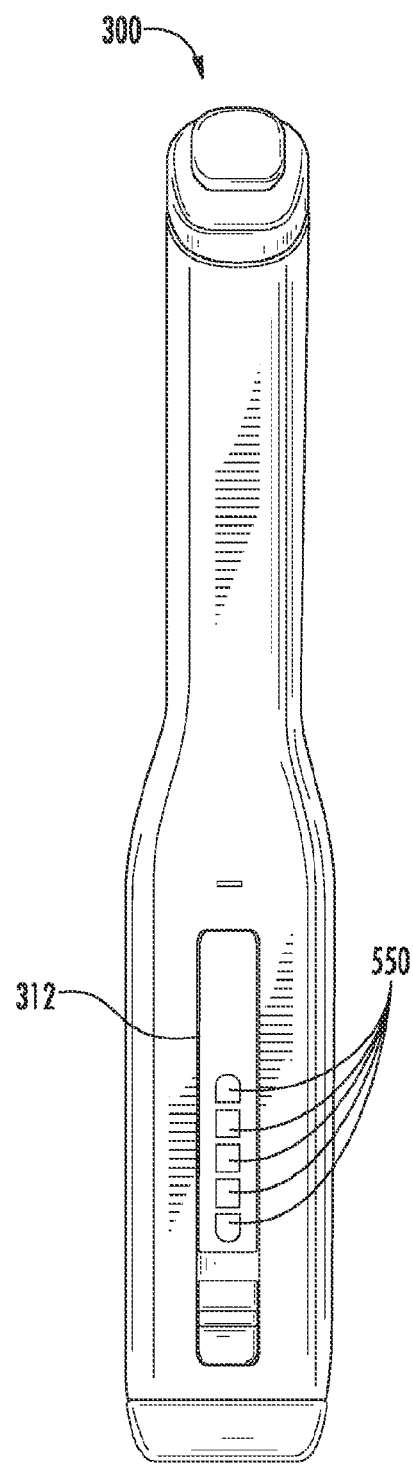
FIG. 12 is a front elevational view of an exemplary embodiment of the autoinjector 300 which illustrates progress LEDs 550 of the user interface 312.

Referring still to FIG. 9, once the target light is turned on in the "cap off" state of block 522, touching the proximal end wall of the autoinjector to skin at the injection site so that the skin sensor senses contact with skin, may cause the microprocessor to may place the autoinjector into a "ready to inject" state in block 526, where it continuously illuminates the start button in a first predetermined color (e.g., green), turns on all progress LEDs 550 of the user interface (FIG. 12), generates a sound with the speaker that indicates that the injector is ready to start and injection cycle, turns off the target light, keeps on the backlight so that the user can view the progress of the injection in the syringe. If the skin sensor does not sense contact with skin within a predetermined time period (e.g., 60 seconds) after entering the "read to inject" state of block 526, the microprocessor may place the autoinjector in a "cap off sleep" state in block 524, where it turns off the progress LEDs 550 (FIG. 12) and the audio speaker. If the start or eject button is subsequently pressed, the microprocessor may place the autoinjector into the "cap off" state in block 522, as previously described. If, however, the start or eject button is subsequently pressed and the skin sensor senses contact with skin, the microprocessor may place the autoinjector in to the "ready to inject" state of block 526, as previously described. If the autoinjector is then lifted off the skin, the microprocessor may place the autoinjector back in the "cap on" state of block 522.

Referring again to FIG. 9, with the autoinjector in the "ready to inject" state of block 526, pressing the start button causes the microprocessor to place the autoinjector into an "injection start" state in block 528, where it changes the continuous illumination of start button to a second predetermined color (e.g., blue) and keeps the backlight and the progress LED on. If the microprocessor detects that the injection needle is not pushed into the skin, it may retract the needle and visually and audibly alert a needle jam in block 530, e.g., the user interface may blink "cassette fail" icon (FIG. 13) for a predetermined time period (e.g., 60 seconds) and the speaker may generate the error sound. The microprocessor may then open the cassette door after a predetermined time period and place the autoinjector in the "door open, sleep B" state of block 546. If, however, the injection needle pushes into the skin, and after a predetermine time period has elapsed (e.g., 0.5 seconds), the microprocessor may place the autoinjector in an "injection progress" state in block 532, where the start button may remain continuously illuminated in the second predetermined color and the backlight and the progress LED may remain on. If the plunger subsequently pushes a clogged cassette, the microprocessor may retract the injection needle and visibly and audibly signal in block 534 a plunger jam, i.e., the user interface may blink a "cassette fail" icon (FIG. 13) for a predetermined time period (e.g., 60 seconds) and the speaker may generate the error sound. The microprocessor may then open the cassette door after a predetermined time period and place the autoinjector into the "door open, sleep B" state of block 546. If, instead, the autoinjector is lifted off the skin beyond an acceptable limit for a predetermined time period (e.g., 1 second), the microprocessor may retract the injection needle and visibly and audibly signal in block 536 an "off skin too long" alert, e.g., the user interface may blink a "cassette fail" icon (FIG. 13) for a predetermined time period (e.g., 60 seconds) and the speaker may generate the error sound.

Returning to block 532 of FIG. 9, as selected drug injection time period elapses the progress LEDs 550 (FIG. 12) may be sequentially turned off by the microprocessor to indicate the progression of the injection cycle. Once the injection cycle has completed, the microprocessor may retract the injection needle thereby placing the autoinjector into a "needle retraction" state in block 538, where it continuously illuminates the start button in the second predetermined color, maintains the backlight in the on state and maintains only one of the progress LEDs 550 (FIG. 12) in the on state. The microprocessor may then partially retract the plunger rod and fully retract the injection needle thereby placing the autoinjector in an "injection complete" state and indicate in block 540, where it may change the illumination color of the start button back to the first predetermined color, turn off the backlight and last progress LED 550 (FIG. 12), and generate a sound with the audio speaker that indicates that the injection is complete. If the autoinjector is removed from the skin for a predetermine time period (e.g., 5 second) elapses, the microprocessor may place the autoinjector in a "plunger retraction" state in block 542, and may terminate the illumination of the start button. The microprocessor may then retract the plunger rod and automatically open the cassette door in block 544 which places the autoinjector in the "door open, sleep B" state of block 546. Removal of the spent cassette can now be made and the cassette door closed, which places the autoinjector in the "off, door closed" state of block 500. If the microprocessor detects a low battery in the "automatic door open" state of block 544, (which may indicate that a certain number of injections remain, that a certain number of injections have been made, or that a certain number of days of usage has passed) the microprocessor may cause the autoinjector to visibly and audibly signal a "battery low" error alert by blinking the "low battery" icon (FIG. 13) with the user interface and generating the error sound with the audio speaker.

Figure 10A:
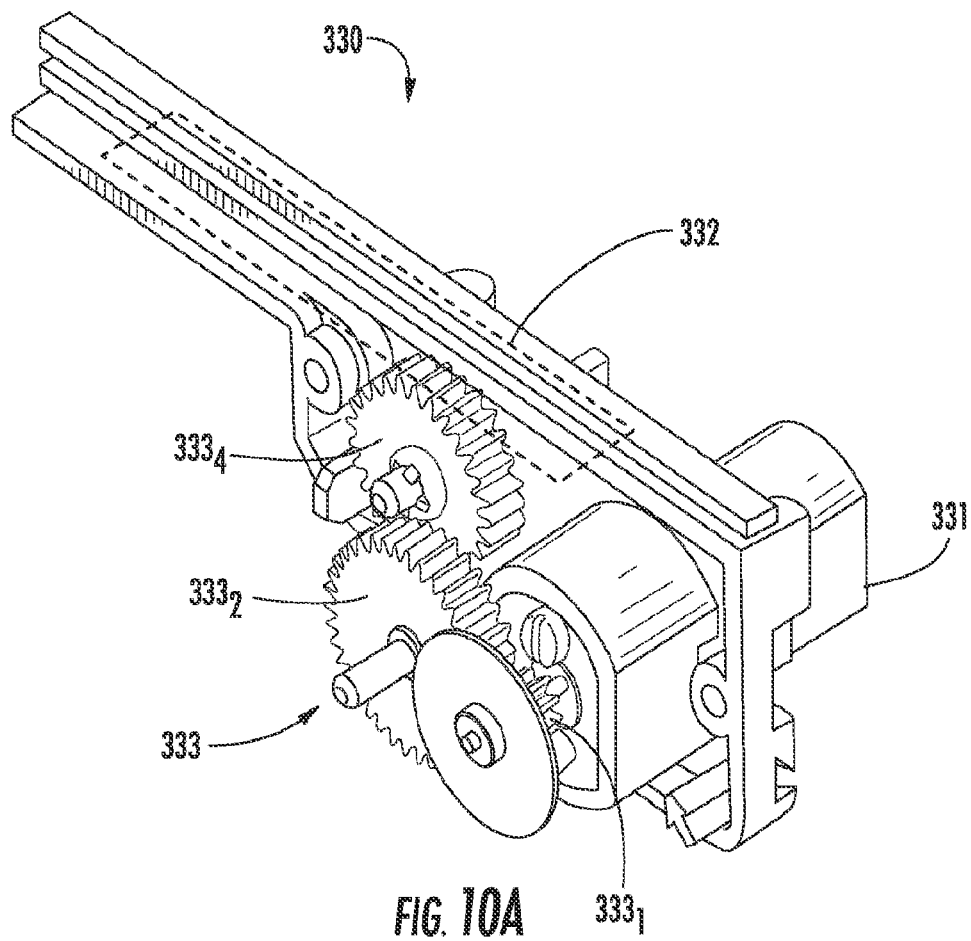
FIG. 10A is a top down perspective side view of an exemplary embodiment of the motorized insertion drive 330 which may comprise an insertion drive motor 331, a drive link or rack 332, an insertion drive gear train 333 including a plurality of gears 3331, 3332, 3333, 3334, a top rack surface 332T, a bottom rack surface 332B, spaced-apart first and second protrusions, 3321 and 3322, and rack teeth 334.
Figure 10B:
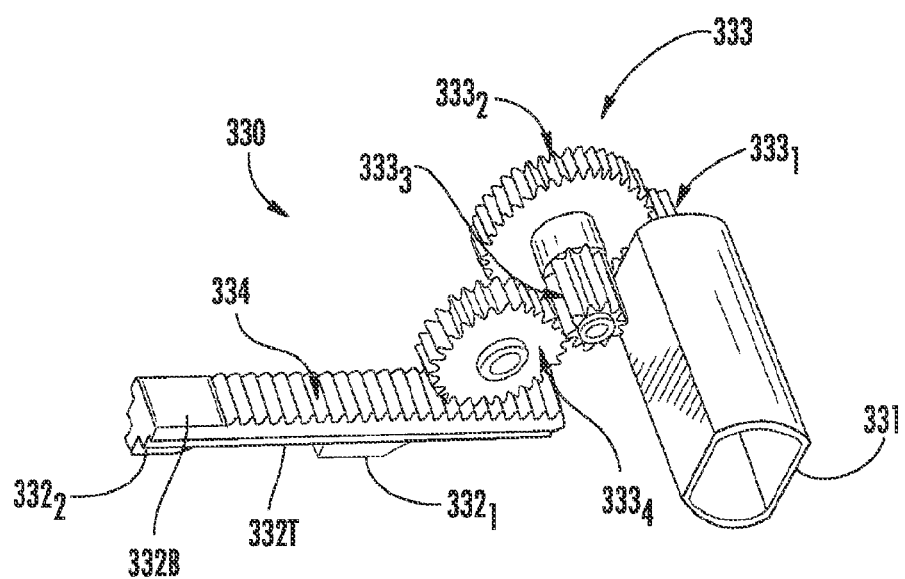
FIG. 10B is a bottom up perspective view, of an exemplary embodiment of the motorized insertion drive 330 which may comprise an insertion drive motor 331, a drive link or rack 332, an insertion drive gear train 333 including a plurality of gears 3331, 3332, 3333, 3334, a top rack surface 332T, a bottom rack surface 332B, spaced-apart first and second protrusions, 3321 and 3322, and rack teeth 334.

Referring again to FIG. 8, the motorized insertion drive 330 performs a needle insertion cycle and a needle retraction cycle. FIGS. 10A and 10B respectively illustrate a top down perspective side view and a bottom up perspective side view of an embodiment of the motorized insertion drive 330. The insertion drive 300 may comprise an insertion drive motor 331, a drive link or rack 332, and an insertion drive gear train 333 including a plurality of gears $333_1$, $333_2$, $333_3$, $333_4$, for transmitting the rotary motion of the insertion drive motor 331 to drive the rack 332. The rack 332 may include a top surface 332T and a bottom surface 332B. The top surface 332T of the rack 332 may include spaced-apart first and second protrusions, $332_1$ and $332_2$, respectively. The bottom surface 332B of the rack 332 may include rack teeth 334. The rack teeth 334 of the rack engage gear $333_4$ of the gear train 333. During a needle insertion cycle, the first protrusion $332_1$ of the rack 332 unlatches the inner sleeve pin 268 of the inner sleeve 220 of the cassette 200 from the latch 218 of the outer cassette housing 210 (FIG. 3B) and then engages and then pushes the inner sleeve pin 268 to drive the inner sleeve 220 containing the syringe 260 forward within the outer housing of the cassette 200 from the home position to the needle extended position where the injection needle 265 of the syringe 260 extends out from the cassette 200 and is inserted into the skin at the injection site. During a needle retraction cycle, the second protrusion $332_2$ of the rack 332 engages and then pulls the inner sleeve pin 268 to drive the inner sleeve 220 containing the syringe 260 backward within the outer housing of the cassette 200 into the home position again, thereby withdrawing the injection needle 265 of the syringe 260 from the skin at the injection site and retracting it back into the cassette 200 (after drug extrusion) where the needle is shielded and locked within the cassette 200 for safe handling and disposal. The needle insertion positioning and timing are monitored and controlled by the microprocessor 350 of the autoinjector. If an error occurs, the error will be indicated on the user interface 312 (FIG. 6A) along with audible alert from the speaker. The insertion drive 330 enables the autoinjector apparatus 100 to deliver the pharmaceutical product subcutaneously (SC) with a predetermined needle injection depth. This needle-depth parameter is accomplished when the insertion drive 330 moves the inner sleeve 220/syringe 260 forward to a mechanical hard stop within the outer housing 210 of the cassette 200. The mechanical hard stop limits the travel of the syringe 260 in the direction of the patient's skin, ensuring needle depth to the desired predetermined specification. Monitoring the movement of the motor 331 enables detection of incomplete needle insertion, which will trigger needle retraction and termination of the injection cycle, accompanied by audible and visual alerts.

Figure 11A:
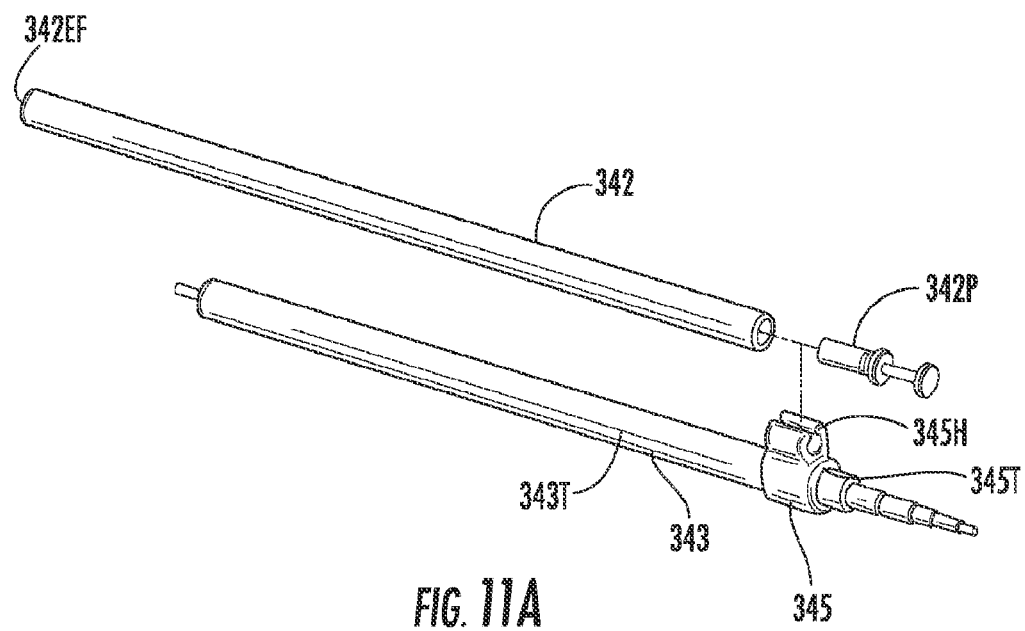
FIG. 11A is an exploded perspective side view of a plunger rod 342, a lead screw 343, and a nut 345 of an exemplary embodiment of the motorized extrusion drive illustrating a pusher 342P of the plunger rod 342, an end face 342EF of the plunger rod 342, an internal screw thread 345T of the nut 345, an external screw thread 343T of the lead screw 343, and a holder 345H of the nut 345.
Figure 11B:
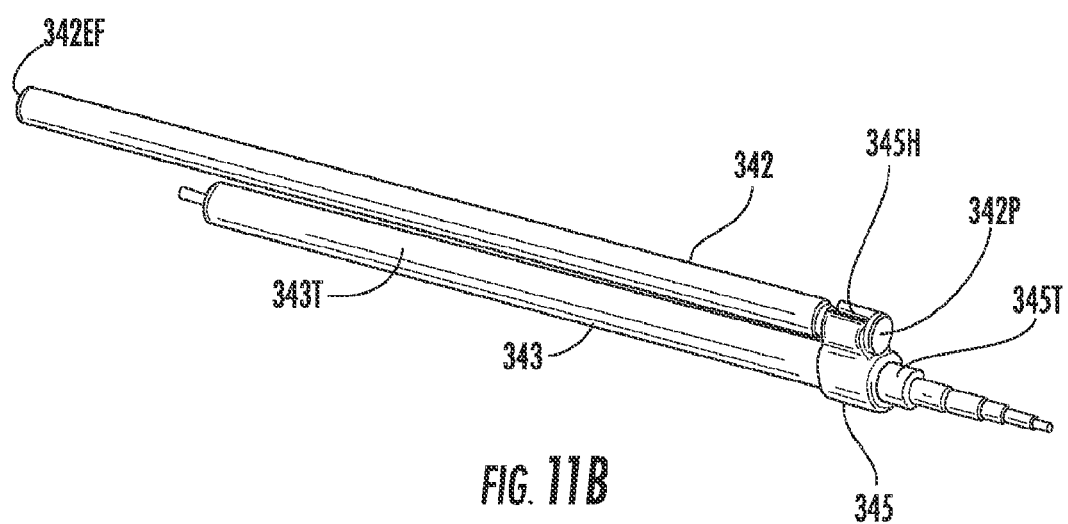
FIG. 11B is an assembled perspective side view of the plunger rod 342, the lead screw 343, and the nut 345 of FIG. 11B, illustrating the pusher 342P of the plunger rod 342, the end face 342EF of the plunger rod 342, the internal screw thread 345T of the nut 345, the external screw thread 343T of the lead screw 343, and the holder 345H of the nut 345.
Figure 11C:
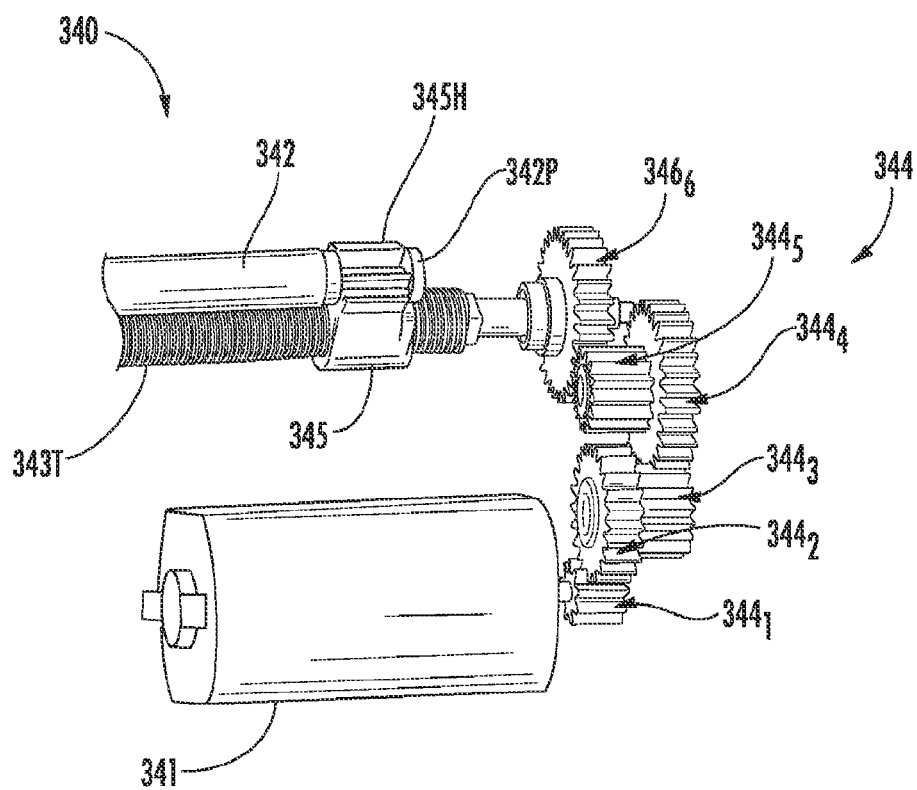
FIG. 11C is a perspective view of a portion of the motorized extrusion drive 340, illustrating an extrusion drive motor 341, the plunger rod 342, the lead screw 343, an extrusion drive gear train 344, the pusher 342P, the nut 345, the external screw thread 343T of the lead screw 343, the holder 345H of the nut 345, and a plurality of gears 3441, 3442, 3443, 3444, 3445, 3446 of the extrusion drive gear train.

The motorized extrusion drive 340 illustrated in FIG. 8, performs the drug extrusion cycle where the pharmaceutical product is emptied from the syringe 260. FIGS. 11A-11B are perspective side views illustrating an embodiment of the motorized extrusion drive 340. FIG. 11A illustrates an exploded perspective side view of an embodiment of a plunger rod/drive screw arrangement of the motorized extrusion drive 340. FIG. 11B illustrates an assembled perspective side view of the plunger rod/drive screw arrangement illustrated in FIG. 11A. FIG. 11C illustrates a perspective view of an embodiment of a gear train of the motorized insertion drive 330. The extrusion drive 340 may comprise an extrusion drive motor 341, a plunger rod 342, a lead screw 343, and an extrusion drive gear train 344. The plunger rod 342 is driven by the extrusion drive motor 341 through the lead screw 343 and the extrusion drive gear train 344. As illustrated in FIGS. 11A and B, the plunger rod 342 may include a pusher 342P and the lead screw 343 may include a nut 345. The nut 345 mechanically couples the plunger rod 342 to the lead screw 343. The nut 345 may include an internal screw thread 345T that threadedly engages an external screw thread 343T of the lead screw 343. The nut 35 may also include a holder 345H that fixedly holds the pusher 342P of the plunger rod 342. As illustrated in FIG. 11C, the extrusion drive gear train 344 may include a plurality of gears 3441, 3442, 3443, 3444, 3445, 3446. The gears 3441 and 3446 of the extrusion drive gear train 344 are coupled to the extrusion drive motor 341 and the lead screw 343, respectively, thereby allowing the extrusion drive gear train 344 to transmit the rotary motion of the insertion drive motor 331 to drive the lead screw 343. As the lead screw 343 rotates, the nut 345 (which is threadedly engaged with the lead screw 343) moves forward or backward (depending upon the lead screw's direction of rotation) along the lead screw 343, which in turn, drives the plunger rod 342 forward and backward in the autoinjector 300. Forward movement of the plunger rod 342 causes an end face 342EF of the plunger rod 342 to enter the cassette 200 and subsequently the syringe barrel 261 of the syringe 260. The plunger rod 343 then engages the plunger-stopper 264 of the syringe 260 and pushes it to the end of the syringe barrel 261 in order to expel the predetermined dose of the pharmaceutical product from the syringe 260 during a drug extrusion cycle. The position of the components of extrusion drive 340, as well as time related to drug extrusion, may be monitored by the microprocessor 350. If an error occurs, the error can be indicated on the user interface 312 along with an audible alert. The microprocessor 350 may be capable of storing different factory-set drug delivery profiles (stroke, speed, acceleration). A plurality of unique drug delivery profiles may be associated with specific cassette configurations. The cassette identification arrangement on the outer housing 210 of the cassette 200 enable the autoinjector 300 to identify the proper drug delivery profile specific for the loaded pharmaceutical product. Upon insertion and recognition of a valid cassette 200, available preset drug extrusion speed ranges may be automatically registered by the autoinjector 300. Available speed ranges are dependent upon the syringe fill volume and pharmaceutical product characteristics, such as viscosity.

The user may select the desired drug extrusion speed (defined as the time to empty the pharmaceutical product of the syringe 260) from a plurality of different options for a particular pharmaceutical product using the speed selector switch 316. Upon initiation of the drug extrusion cycle, the stroke of the plunger rod 342 may be controlled and monitored to ensure the plunger-stopper 264 reaches the end of the syringe barrel 261, which ensures complete dose administration. If an error occurs during the extrusion process (e.g., failure of the plunger rod to achieve a complete stroke), the autoinjector 300 may immediately terminate drug extrusion, retract the needle back into the cassette 200, and provide audible and visual alerts.

The injection cycles may be indicated by both audible and visual signals. Lights on the autoinjector 300 may turn off in sequence from top to bottom during the injection cycle to indicate to the user the progress of the injection. Upon completion of the injection cycle, the autoinjector 300 retracts the syringe needle back into the disposable cassette 200, and then opens the cassette door 308 automatically, allowing removal of the cassette 200 by the user. The opening of the cassette door 308 may also be an indicator to the user that the injection cycle is complete.

In the event that an error occurs during the injection cycle, the autoinjector 300 may be equipped with various audible and visual signals to alert the user (operator or patient) to the error and to prompt appropriate actions.

The battery 360 illustrated in FIG. 8, may be a non-replaceable, non-rechargeable battery. The battery 360 should be capable of providing sufficient power for adequate shelf-life and service life to meet the drug delivery requirements. A power-on self test is automatically performed upon waking the autoinjector 300 to ensure sufficient battery power is available for a successful injection cycle. The user interface 312 of the autoinjector 300 may provide visual and audible alerts if a problem occurs with the battery 360 before injection. The microprocessor 350 may be programmed to disable the autoinjector 300 at the end of the defined service life.

The syringe 260 of the cassette 200 may be prefilled with a pharmaceutical product, such as an erythropoiesis stimulating agent (ESA), which may be in a liquid or a lyophilized form. An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins comprise erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins comprise, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (comprising EMP1/Hematide), and mimetic antibodies. Exemplary erythropoiesis stimulating proteins comprise erythropoietin, darbepoetin, erythropoietin agonist variants, and peptides or antibodies that bind and activate erythropoietin receptor.

The term erythropoiesis stimulating protein comprises without limitation Epogen® (epoetin alfa), Aranesp® (darbepoetin alfa), Dynepo® (epoetin delta), Mircera® (methyoxy polyethylene glycol-epoetin beta), Hematide™ (peginesatide), MRK-2578, INS-22, Retacrit® (epoetin zeta), Neorecormon® (epoetin beta), Silapo™ (epoetin zeta), Binocrit® (epoetin alfa), epoetin alfa Hexal, Abseamed™ (epoetin alfa), Ratioepo™ (epoetin theta), Eporatio™ (epoetin theta), Biopoin™ (epoetin theta), epoetin alfa, epoetin beta, epoetin zeta, epoetin theta, and epoetin delta.

The term erythropoiesis stimulating protein further comprises the molecules or variants or analogs as disclosed in the following patents or patent applications: U.S. Pat. Nos. 4,703,008; 5,441,868; 5,547,933; 5,618,698; 5,621,080; 5,756,349; 5,767,078; 5,773,569; 5,830,851; 5,856,298; 5,955,422; 5,986,047; 6,030,086; 6,310,078; 6,391,633; 6,583,272; 6,586,398; 6,900,292; 6,750,369; 7,030,226; 7,084,245; and 7,271,689; U.S. Publ. Nos. 2002/0155998; 2003/0077753; 2003/0082749; 2003/0143202; 2003/0215444; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0040858; 2006/0088906; and 2006/0111279; and PCT Publ. Nos. WO 91/05867; WO 95/05465; WO 96/40772; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; WO 2006/29094; and WO 2007/136752.

Alternatively, the syringe 260 of the cassette 200 may also be prefilled with other products. Examples of other pharmaceutical products that may be used may comprise, but are not limited to, therapeutics such as a biological (e.g., Enbrel® (etanercept, TNF-receptor/Fc fusion protein, TNF blocker), anti-TNF antibodies such as adalimumab, infliximab, certolizumab pegol, and golimumab; anti-IL-12 antibodies such as ustekinumab, other Fc fusions such as CTL4A:Fc also known as abacept; Neulasta0 (pegylated filgastrim, pegylated G-CSF, pegylated hu-met-G-CSF), Neupogen® (filgrastim, G-CSF, hu-met-G-CSF), Nplate® (romiplostim), Vectibix® (panitumumab), Sensipar® (cinacalcet), and Xgeva® and Prolia® (each denosamab, AMG 162); as well as other small molecule drugs, a therapeutic antibodies, a polypeptides, proteins or other chemicals, such as an iron (e.g., ferumoxytol, iron dextrans, ferric glyconate, and iron sucrose). The therapeutic may be in liquid form, or reconstituted from lyophilized form.

Among particular illustrative proteins that can be used in the syringe 260 of the cassette 200 are antibodies, peptibodies, pegylated proteins, polypeptides, and related proteins (comprising fusions, fragments, analogs, variants or derivatives thereof) for example, proteins that specifically bind to: OPGL; TL-4 receptor; interleukin 1-receptor 1 ("IL1-R1"); angiopoietin-2 (Ang2); NGF; CD22; IGF-1; B-7 related protein 1 (B7RP1); IL-15; IL-17 Receptor A: IFN gamma; TALL-1; parathyroid hormone ("PTH"); thrombopoietin receptor ("TPO-R"); hepatocyte growth factor ("HGF"); TRAIL-R2; Activin A; TGF-beta; amyloid-beta; c-Kit; a4137: and IL-23 or one of its subunits; and other therapeutic proteins.

The syringe 260 of the cassette 200 may also be prefilled with OPGL specific antibodies, peptibodies, and related proteins, and the like (also referred to as RANKL specific antibodies, peptibodies and the like), comprising fully humanized and human OPGL specific antibodies, particularly fully humanized monoclonal antibodies, comprising but not limited to the antibodies described in PCT Publ. No. WO 03/002713, including OPGL specific antibodies and antibody related proteins, particularly those having the sequences set forth therein, particularly, but not limited to, those denoted therein: 9H7; 18B2; 2D8; 2E11; 16E1; and 22B3, comprising the OPGL specific antibodies having either the light chain of SEQ ID NO: 2 therein as set forth in FIG. 2 therein and/or the heavy chain of SEQ ID NO:4 therein, as set forth in FIG. 4 therein.

The syringe 260 of the cassette 200 may also be prefilled with myostatin binding proteins, peptibodies, and related proteins, and the like, comprising myostatin specific peptibodies, particularly those described in US Publ. No. 2004/0181033 and PCT Publ. No. WO 2004/058988, particularly in parts pertinent to myostatin specific peptibodies, comprising but not limited to peptibodies of the mTN8-19 family, comprising those of SEQ ID NOS: 305-351, comprising TN8-19-1 through TN8-19-40, TN8-19 con1 and TN8-19 con2; peptibodies of the mL2 family of SEQ ID NOS: 357-383 therein; the mL15 family of SEQ ID NOS: 384-409; the mL17 family of SEQ ID NOS: 410-438 therein; the mL20 family of SEQ ID NOS: 439-446 therein; the mL21 family of SEQ ID NOS: 447-452 therein; the mL24 family of SEQ ID NOS: 453-454 therein; and those of SEQ ID NOS: 615-631 therein.

The syringe 260 of the cassette 200 may also be prefilled with IL-4 receptor specific antibodies, peptibodies, and related proteins, and the like, particularly those that inhibit activities mediated by binding of TL-4 and/or TL-1 3 to the receptor, comprising those described in PCT Publ. No. WO 2005/047331 or PCT Appl. No. PCT/US2004/03742 and in US Publ. No. 2005/112694, particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1.

The syringe 260 of the cassette 200 may also be prefilled with IL1-R1 specific antibodies, peptibodies, and related proteins, and the like, comprising but not limited to those described in U.S. Publ. No. 2004/097712A1, including in parts pertinent to IL1-R1 specific binding proteins, monoclonal antibodies in particular, especially, without limitation, those designated therein: 15CA, 26F5, 27F2, 24E12, and 10H7.

The syringe 260 of the cassette 200 also be prefilled with Ang2 specific antibodies, peptibodies, and related proteins, and the like, comprising but not limited to those described in PCT Publ. No. WO 03/057134 and U.S. Publ No. 2003/0229023, particularly in parts pertinent to Ang2 specific antibodies and peptibodies and the like, especially those of sequences described therein and comprising but not limited to: L1(N); L1(N) WT; L1(N) 1K WT; 2×L1(N); 2×L1(N) WT; Con4 (N), Con4 (N) 1K WT, 2×Con4 (N) 1K; L1C; L1C 1K; 2×L1C; Con4C; Con4C 1K; 2×Con4C 1K; Con4-L1 (N); Con4-L1C; TN-12-9 (N); C17 (N); TN8-8(N); TN8-14 (N); Con 1 (N), also comprising anti-Ang 2 antibodies and formulations such as those described in PCT Publ. No. WO 2003/030833 particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; Ab1A1; Ab1F; Ab1K, Ab1P; and Ab1P, in their various permutations as described therein.

The syringe 260 of the cassette 200 may also be prefilled with NGF specific antibodies, peptibodies, and related proteins, and the like comprising, in particular, but not limited to those described in US Publ. No. 2005/0074821 and U.S. Pat. No. 6,919,426, particularly as to NGF-specific antibodies and related proteins in this regard, comprising in particular, but not limited to, the NGF-specific antibodies therein designated 4D4, 4G6, 6H9, 7H2, 14D10 and 14D11.

The syringe 260 of the cassette 200 may also be prefilled with CD22 specific antibodies, peptibodies, and related proteins, and the like, such as those described in U.S. Pat. No. 5,789,554, particularly as to CD22 specific antibodies and related proteins, particularly human CD22 specific antibodies, such as but not limited to humanized and fully human antibodies, comprising but not limited to humanized and fully human monoclonal antibodies, particularly comprising but not limited to human CD22 specific IgG antibodies, such as, for instance, a dimer of a human-mouse monoclonal hLL2 gamma-chain disulfide linked to a human-mouse monoclonal hLL2 kappa-chain, comprising, but limited to, for example, the human CD22 specific fully humanized antibody in Epratuzumab, CAS registry number 501423-23-0;

The syringe 260 of the cassette 200 may also be prefilled with IGF-1 receptor specific antibodies, peptibodies, and related proteins, and the like, such as those described in PCT Publ. No. WO 06/069202, particularly as to TGF-1 receptor specific antibodies and related proteins, comprising but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof.

Also among non-limiting examples of anti-IGF-1R antibodies for use in the methods and compositions of the present invention are each and all of those described in: (i) US Publ. No. 2006/0040358 (published Feb. 23, 2006), 2005/0008642 (published Jan. 13, 2005), 2004/0228859 (published Nov. 18, 2004), comprising but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein; (ii) PCT Publ. No. WO 06/138729 (published Dec. 28, 2006) and WO 05/016970 (published Feb. 24, 2005), and Lu et al., 2004, J Biol. Chem. 279:2856-65, comprising but not limited to antibodies 2F8, A12, and IMC-A12 as described therein; (iii) PCT Publ. No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003); (iv) US Publ. No. 2005/0084906 (published Apr. 21, 2005), comprising but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein; (v) US Publ. Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al., 2003, Cancer Res. 63:5073-83, comprising but not limited to antibody EM164, resurfaced EM164, humanized EM164, huEM164 v1.0, huEM164 v1.1, huEM164 v1.2, and huEM164 v1.3 as described therein; (vi) U.S. Pat. No. 7,037,498 (issued May 2, 2006), US Publ. Nos. 2005/0244408 (published Nov. 30, 2005) and 2004/0086503 (published May 6, 2004), and Cohen, et al., 2005, Clinical Cancer Res. 11:2063-73, e.g., antibody CP-751,871, comprising but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein; (vii) US Publ. Nos. 2005/0136063 (published Jun. 23, 2005) and 2004/0018191 (published Jan. 29, 2004), comprising but not limited to antibody 19D12 and an antibody comprising a heavy chain encoded by a polynucleotide in plasmid 15H12/19D12 HCA (y4), deposited at the ATCC under number PTA-5214, and a light chain encoded by a polynucleotide in plasmid 15H12/19D12 LCF (c), deposited at the ATCC under number PTA-5220, as described therein; and (viii) US Publ. No. 2004/0202655 (published Oct. 14, 2004), comprising but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; particularly as to the aforementioned antibodies, peptibodies, and related proteins and the like that target IGF-1 receptors.

The syringe 260 of the cassette 200 may also be prefilled with B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, TCOS, on activated T cells in particular, especially, in all of the foregoing regards, those disclosed in U.S. Publ. No. 2008/0166352 and PCT Publ. No. WO 07/011941, particularly as to such antibodies and related proteins, comprising but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein).

The syringe 260 of the cassette 200 may also be prefilled with IL-15 specific antibodies, peptibodies, and related proteins, and the like, such as, in particular, humanized monoclonal antibodies, particularly antibodies such as those disclosed in U.S. Publ. Nos. 2003/0138421; 2003/023586; and 2004/0071702; and U.S. Pat. No. 7,153,507, particularly as to IL-15 specific antibodies and related proteins, comprising peptibodies, comprising particularly, for instance, but not limited to, HuMax IL-15 antibodies and related proteins, such as, for instance, 146B7.

The syringe 260 of the cassette 200 may also be prefilled with pharmaceutical compositions comprising antagonistic human monoclonal antibodies against human IL-17 Receptor A. The characterization, cloning, and preparation of IL-17 Receptor A are described in U.S. Pat. No. 6,072,033, issued Jun. 6, 2000. The amino acid sequence of the human IL-17RA is shown in SEQ ID NO:10 of U.S. Pat. No. 6,072,033 (GenBank accession number NM 014339). Such antibodies may comprise those disclosed in WO 2008/054603, or the antibodies claimed in U.S. Pat. No. 7,767,206, issued Aug. 3, 2010, and in U.S. Ser. No. 11/906,094.

The syringe 260 of the cassette 200 may also be prefilled with IFN gamma specific antibodies, peptibodies, and related proteins and the like, especially human IFN gamma specific antibodies, particularly fully human anti-IFN gamma antibodies, such as, for instance, those described in US Publ. No. 2005/0004353, particularly as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, as disclosed in the foregoing US Publication and in Thakur et al., Mol. Immunol. 36:1107-1115 (1999). Specific antibodies comprise those having the heavy chain of SEQ ID NO: 17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing US Publication. A specific antibody contemplated is antibody 1119 as disclosed in foregoing US Publication and having a complete heavy chain of SEQ ID NO:17 as disclosed therein and having a complete light chain of SEQ ID NO:18 as disclosed therein.

The syringe 260 of the cassette 200 may also be prefilled with TALL-1 specific antibodies, peptibodies, and related proteins, and the like, and other TALL specific binding proteins, such as those described in U.S. Publ. Nos. 2003/0195156 and 2006/0135431, particularly as to TALL-1 binding proteins, particularly the molecules of Tables 4 and 5B therein.

The syringe 260 of the cassette 200 may also be prefilled with PTH specific antibodies, peptibodies, and related proteins, and the like, such as those described in U.S. Pat. No. 6,756,480, particularly in parts pertinent to proteins that bind PTH.

The syringe 260 of the cassette 200 may also be prefilled with TPO-R specific antibodies, peptibodies, and related proteins, and the like, such as those described in U.S. Pat. No. 6,835,809, particularly in parts pertinent to proteins that bind TPO-R.

The syringe 260 of the cassette 200 may also be prefilled with HGF specific antibodies, peptibodies, and related proteins, and the like, comprising those that target the HGF/SF:cMet axis (HGF/SF:c-Met), such as the fully human monoclonal antibodies that neutralize hepatocyte growth factor/scatter (HGF/SF) described in US Publ. No. 2005/0118643 and PCT Publ. No. WO 2005/017107, huL2G7 described in U.S. Pat. No. 7,220,410 and OA-5d5 described in U.S. Pat. Nos. 5,686,292 and 6,468,529 and in PCT Publ. No. WO 96/38557, particularly in parts pertinent to proteins that bind HGF.

The syringe 260 of the cassette 200 may also be prefilled with TRAIL-R2 specific antibodies, peptibodies, related proteins and the like, such as those described in U.S. Pat. No. 7,521,048, particularly in parts pertinent to proteins that bind TRAIL-R2.

The syringe 260 of the cassette 200 may also be prefilled with Activin A specific antibodies, peptibodies, related proteins, and the like, comprising but not limited to those described in US Publ. No. 2009/0234106, particularly in parts pertinent to proteins that bind Activin A.

The syringe 260 of the cassette 200 may also be prefilled with TGF-beta specific antibodies, peptibodies, related proteins, and the like, comprising but not limited to those described in U.S. Pat. No. 6,803,453 and US Publ. No. 2007/0110747, particularly in parts pertinent to proteins that bind TGF-beta.

The syringe 260 of the cassette 200 may also be prefilled with amyloid-beta protein specific antibodies, peptibodies, related proteins, and the like, comprising but not limited to those described in PCT Publ. No. WO 2006/081171, particularly in parts pertinent to proteins that bind amyloid-beta proteins. One antibody contemplated is an antibody having a heavy chain variable region comprising SEQ ID NO: 8 and a light chain variable region having SEQ ID NO: 6 as disclosed in the International Publication.

The syringe 260 of the cassette 200 may also be prefilled with c-Kit specific antibodies, peptibodies, related proteins, and the like, comprising but not limited to those described in Publ. No. 2007/0253951, particularly in parts pertinent to proteins that bind c-Kit and/or other stem cell factor receptors.

The syringe 260 of the cassette 200 may also be prefilled with OX4OL specific antibodies, peptibodies, related proteins, and the like, comprising but not limited to those described in U.S. application Ser. No. 11/068,289, particularly in parts pertinent to proteins that bind OX4OL and/or other ligands of the OX040 receptor.

The syringe 260 of the cassette 200 may also be prefilled with other exemplary proteins comprising but are not limited to Activase® (Alteplase, tPA); Aranesp® (Darbepoetin alfa), Epogen® (Epoetin alfa, or erythropoietin); Avonex® (Interferon beta-1a); Bexxar® (Tositumomab, anti-CD22 monoclonal antibody); Betaseron® (Interferon-beta); Campath® (Alemtuzumab, anti-CD52 monoclonal antibody); Dynepo® (Epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (Epoetin alfa); Erbitux® (Cetuximab, anti-EGFR/HER1/c-ErbB-1); Genotropin® (Somatropin, Human Growth Hormone); Herceptin® (Trastuzumab, anti-HER2/neu (erbB2) receptor mAb); Humatrope® (Somatropin, Human Growth Hormone); Humira® (Adalimumab); Insulin in Solution; Infergen® (Interferon Alfacon-1); Natrecor® (nesiritide; recombinant human B-type natriuretic peptide (hBNP); Kineret® (Anakinra), Leukine® (Sargamostim, rhuGM-CSF); LymphoCide® (Epratuzumab, anti-CD22 mAb); Lymphostat B® (Belimumab, anti-BlyS mAb); Metalyse® (Tenecteplase, t-PA analog); Mircera® (methoxy polyethylene glycol-epoetin beta); Mylotarg® (Gemtuzumab ozogamicin); Raptiva® (efalizumab); Cimzia® (certolizumab pegol, CDP 870); Soliris™ (Eculizumab); Pexelizumab (Anti-05 Complement); MEDI-524 (Numax®); Lucentis® (Ranibizumab); 17-1A (Edrecolomab, Panorex®); Trabio® (lerdelimumab); TheraCim hR3 (Nimotuzumab); Omnitarg (Pertuzumab, 2C4); Osidem® (IDM-1); OvaRex® (B43.13); Nuvion® (visilizumab); Cantuzumab mertansine (huC242-DM1); NeoRecormon® (Epoetin beta); Neumega® (Oprelvekin, Human Interleukin-11); Neulasta® (Pegylated filgastrim, pegylated G-CSF, pegylated hu-Met-G-CSF); Neupogen® (Filgrastim, G-CSF, hu-MetG-CSF); Orthoclone OKT3® (Muromonab-CD3, anti-CD3 monoclonal antibody), Procrit® (Epoetin alfa); Remicade® (Infliximab, anti-TNFa monoclonal antibody), Reopro® (Abciximab, anti-GP 1Ib/Ilia receptor monoclonal antibody), Actemra® (anti-IL6 Receptor mAb), Avastin® (Bevacizumab), HuMax-CD4 (zanolimumab), Rituxan® (Rituximab, anti-CD20 mAb); Tarceva® (Erlotinib); Roferon-A®-(Interferon alfa-2a); Simulect® (Basiliximab); Prexige® (lumiracoxib); Synagis® (Palivizumab); 146B7-CHO (anti-IL15 antibody, see U.S. Pat. No. 7,153,507); Tysabri® (Natalizumab, anti-a4integrin mAb); Valortim® (MDX-1303, anti-*B. anthracis* Protective Antigen mAb); ABthrax™; Vectibix® (Panitumumab); Xolair® (Omalizumab), ETI211 (anti-MRSA mAb), IL-1 Trap (the Fc portion of human IgG1 and the extracellular domains of both IL-1 receptor components (the Type I receptor and receptor accessory protein)), VEGF Trap (Ig domains of VEGFR1 fused to IgG1 Fc), Zenapax® (Daclizumab); Zenapax® (Daclizumab, anti-IL-2Ra mAb), Zevalin® (Ibritumomab tiuxetan), Zetia (ezetimibe), Atacicept (TACT-Ig), anti-CD80 monoclonal antibody (mAb) (galiximab), anti-CD23 mAb (lumiliximab). BR2-Fc (huBR3/huFc fusion protein, soluble BAFF antagonist); CNTO 148 (Golimumab, anti-TNFα mAb); HGS-ETR1 (Mapatumumab; human anti-TRATL Receptor-1 mAb); HuMax-CD20 (Ocrelizumab, anti-CD20 human mAb); HuMax-EGFR (zalutumumab); M200 (Volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (N1-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFB mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

The syringe 260 of the cassette 200 may also be prefilled with antibodies comprising, but not limited to, those that recognize any one or a combination of proteins comprising, but not limited to, the above-mentioned proteins and/or the following antigens: CD2, CD3, CD4, CD8, CD11a, CD14, CD18, CD20, CD22, CD23, CD25, CD33, CD40, CD44, CD52, CD80 (B7.1), CD86 (B7.2), CD147, TL-1α, IL-1β, TL-2, IL-3, TL-7, TL-4, TL-5, TL-8, TL-10, TL-2 receptor, TL-4 receptor, IL-6 receptor, IL-13 receptor, IL-18 receptor subunits, FGL2, PDGF-β and analogs thereof (see U.S. Pat. Nos. 5,272,064 and 5,149,792), VEGF, TGF, TGF-β2, TGF-β1, EGF receptor (see U.S. Pat. No. 6,235,883) VEGF receptor, hepatocyte growth factor, osteoprotegerin ligand, interferon gamma, B lymphocyte stimulator (BlyS, also known as BAFF, THANK, TALL-1, and zTNF4; see Do and Chen-Kiang (2002), Cytokine Growth Factor Rev. 13(1): 19-25), C5 complement, TgE, tumor antigen CA125, tumor antigen MUC1, PEM antigen, LCG (which is a gene product that is expressed in association with lung cancer), HER-2, a tumor-associated glycoprotein TAG-72, the SK-1 antigen, tumor-associated epitopes that are present in elevated levels in the sera of patients with colon and/or pancreatic cancer, cancer-associated epitopes or proteins expressed on breast, colon, squamous cell, prostate, pancreatic, lung, and/or kidney cancer cells and/or on melanoma, glioma, or neuroblastoma cells, the necrotic core of a tumor, integrin alpha 4 beta 7, the integrin VLA-4, B2 integrins, TRAIL receptors 1, 2, 3, and 4, RANK, RANK ligand, TNF-α, the adhesion molecule VAP-1, epithelial cell adhesion molecule (Ep-CAM), intercellular adhesion molecule-3 (ICAM-3), leukointegrin adhesin, the platelet glycoprotein gp TIb/TITa, cardiac myosin heavy chain, parathyroid hormone, rNAPc2 (which is an inhibitor of factor VIIa-tissue factor), MHC I, carcinoembryonic antigen (CEA), alpha-fetoprotein (AFP), tumor necrosis factor (TNF), CTLA-4 (which is a cytotoxic T lymphocyte-associated antigen), Fc-γ-1 receptor, HLA-DR 10 beta, HLA-DR antigen, L-selectin, Respiratory Syncitial Virus, human immunodeficiency virus (HIV), hepatitis B virus (HBV), *Streptococcus mutans*, and *Staphlycoccus aureus*.

Additional examples of known antibodies that may be contained in the syringe 260 of the cassette 200 can comprise but are not limited to adalimumab, bevacizumab, infliximab, abciximab, alemtuzumab, bapineuzumab, basiliximab, belimumab, briakinumab, canakinumab, certolizumab pegol, cetuximab, conatumumab, denosumab, eculizumab, gemtuzumab ozogamicin, golimumab, ibritumomab tiuxetan, labetuzumab, mapatumumab, matuzumab, mepolizumab, motavizumab, muromonab-CD3, natalizumab, nimotuzumab, ofatumumab, omalizumab, oregovomab, palivizumab, panitumumab, pemtumomab, pertuzumab, ranibizumab, rituximab, rovelizumab, tocilizumab, tositumomab, trastuzumab, ustekinumab, zalutumumab, and zanolimumab.

Although the autoinjector apparatus has been described in terms of exemplary embodiments, it is not limited thereto. Rather, the appended claims should be construed broadly, to comprise other variants and embodiments of the autoinjector apparatus, which may be made by those skilled in the art without departing from the scope and range of equivalents of the apparatus and its elements.

What is claimed is:

1. A single-use cassette for use with an autoinjector, the cassette comprising:
    a housing;
    an inner sleeve disposed in the housing and movable between first and second positions along a longitudinal axis, the inner sleeve comprising one or more side walls defining an interior, and at least one receptacle having a rearward opening, the at least one receptacle separate from and disposed adjacent to the interior;
    a syringe disposed in the interior of the inner sleeve; and
    lock cap for securing the syringe in the inner sleeve, the lock cap including an elastomeric bumper, the lock cap affixed to a distal end of the inner sleeve with the elastomeric bumper contacting a distal end of the syringe, wherein the lock cap comprises at least one arm member extending generally parallel to the longitudinal axis for inserting into the at least one receptacle.

2. The cassette of claim 1, wherein the at least one arm member of the lock cap comprises a barb arrangement for gripping an inner surface of the receptacle of the inner sleeve.

3. The cassette of claim 1, wherein the cassette further comprises a shield remover extending through an opening in a proximal end of the housing for removing a needle shield from the syringe, wherein the shield remover comprises a spring-biased tab, the tab disposed within an aperture defined in a wall of the housing.

4. The cassette of claim 3, wherein the shield remover comprises an elongated body having a proximal end and a distal end, the distal end comprising at least one flexible tongue that expands outwardly when the shield remover is removed from the cassette to prevent the shield remover from being reinserted into the cassette.

5. The cassette of claim 1, further comprising a therapeutic product in the syringe.

6. The cassette of claim 5, wherein the therapeutic product is Epogen®, Aranesp®, Enbrel® Neulasta®, Neupogen®, Nplate®, Vectibix®, Sensipar®, Xgeva®, Prolia®, an antibody to IL-17 Receptor A, antagonist of angiopoietin-2, a TNF blocker or inhibitor, etanercept, adalimumab, certolizumab, golimumab or infliximab.

7. The cassette of claim 1, further comprising a cassette identification arrangement on a surface of the housing to enable the auto injector to identify the cassette.

8. The cassette of claim 7, wherein the cassette identification arrangement comprises at least one projection.

9. An apparatus for injection of a therapeutic product, the apparatus comprising:
    an auto injector; and
    a single-use cassette for use with the injector, the cassette comprising:
        a housing;
        an inner sleeve disposed in the housing and movable between first and second positions along a longitudinal axis, the inner sleeve comprising one or more sidewalls defining an interior, and at least one receptacle having a rearward opening, the at least one receptacle separate from and disposed adjacent to the interior;
        a syringe disposed in the inner sleeve; and
        a lock cap for securing the syringe in the inner sleeve, the lock cap including an elastomeric bumper, the lock cap affixed to a distal end of the inner sleeve with the elastomeric bumper contacting a distal end of the syringe, wherein the lock cap comprises at least one arm member extending generally parallel to the longitudinal axis and inserted into the at least one receptacle.

10. The apparatus of claim 9, wherein the at least one arm member of the lock cap comprises a barb arrangement for gripping an inner surface of the receptacle of the inner sleeve.

11. The apparatus of claim 9, wherein the cassette further comprises a shield remover extending through an opening in a proximal end of the housing for removing a needle shield from the syringe, wherein the shield remover comprises a spring-biased tab, the tab disposed within an aperture defined in a wall of the housing to prevent removal of the shield remover from the cassette.

12. The apparatus of claim 11, wherein the autoinjector comprises a pin for pushing the tab out of the aperture defined in the wall of the housing when the cassette is placed in the injector to thereby allow the shield remover to be removed from the cassette.

13. The apparatus of claim 11, wherein the shield remover comprises an elongated body having a proximal end and a distal end, the distal end comprising at least one flexible tongue that expands outwardly when the shield remover is removed from the cassette to prevent the shield remover from being reinserted into the cassette.

14. The apparatus of claim 9, further comprising a therapeutic product in the syringe.

15. The apparatus of claim 14, wherein the therapeutic product is Epogen®, Aranesp®, Enbrel® Neulasta®, Neupogen®, Nplate®, Vectibix®, Sensipar®, Xgeva®, Prolia®, an antibody to IL-17 Receptor A, an antagonist to angiopoietin-2, a TNF blocker or inhibitor, etanercept, adalimumab, certolizumab, golimumab, or infliximab.

16. The apparatus of claim 9, further comprising a cassette identification arrangement on a surface of the housing to enable the auto injector to identify the cassette.

17. The apparatus of claim 16, wherein the cassette identification arrangement comprises at least one projection.

18. The apparatus of claim 16, wherein the autoinjector comprises a detector for reading the cassette identification arrangement to identify the cassette.

19. The apparatus of claim 9, wherein the at least one receptacle of the inner sleeve comprises at least two receptacles and the at least one arm member of the lock cap comprises at least two arm members inserted into the at least two receptacles.

20. A single-use cassette for use with an autoinjector, the cassette comprising:
    a housing;
    an inner sleeve disposed in the housing and movable between first and second positions along a longitudinal axis, the inner sleeve comprising one or more side walls defining an interior;
    a syringe disposed in the interior of the inner sleeve; and lock cap for securing the syringe in the inner sleeve, the lock cap including an elastomeric bumper, the lock cap affixed to a distal end of the inner sleeve with the elastomeric bumper contacting a distal end of the syringe, wherein the distal end of the inner sleeve comprises at least one receptacle adjacent to the interior of the inner sleeve having a rearward opening and the lock cap comprises at least one arm member extending generally parallel to the longitudinal axis for inserting into the at least one receptacle;

wherein the at least one receptacle of the inner sleeve comprises at least two receptacles and the at least one arm member of the lock cap comprises at least two arm members for inserting into the at least two receptacles.

* * * * *